(12) United States Patent
Bhatt et al.

(10) Patent No.: US 10,214,580 B2
(45) Date of Patent: *Feb. 26, 2019

(54) CONSTRUCTS AND LIBRARIES COMPRISING ANTIBODY SURROGATE LIGHT CHAIN SEQUENCES

(71) Applicant: I2 PHARMACEUTICALS, INC., Boulder, CO (US)

(72) Inventors: Ramesh Bhatt, Belmont, CA (US); Lawrence Horowitz, Atherton, CA (US); Li Xu, Cupertino, CA (US)

(73) Assignee: I2 PHARMACEUTICALS, INC., Boulder, CO (US)

( * ) Notice: Subject to any disclaimer, the term of this patent is extended or adjusted under 35 U.S.C. 154(b) by 628 days.

This patent is subject to a terminal disclaimer.

(21) Appl. No.: 14/047,301

(22) Filed: Oct. 7, 2013

(65) Prior Publication Data
US 2014/0228544 A1 Aug. 14, 2014

Related U.S. Application Data

(63) Continuation of application No. 13/371,347, filed on Feb. 10, 2012, now abandoned, which is a continuation of application No. 12/056,151, filed on Mar. 26, 2008, now Pat. No. 8,114,967.

(60) Provisional application No. 60/920,568, filed on Mar. 27, 2007.

(51) Int. Cl.
| C07K 16/10 | (2006.01) |
| C07K 16/00 | (2006.01) |
| C07K 14/705 | (2006.01) |
| C07K 16/18 | (2006.01) |
| C07K 16/22 | (2006.01) |
| C07K 16/24 | (2006.01) |
| C40B 40/10 | (2006.01) |

(52) U.S. Cl.
CPC ............ *C07K 16/00* (2013.01); *C07K 16/005* (2013.01); *C07K 16/1018* (2013.01); *C07K 16/18* (2013.01); *C07K 16/22* (2013.01); *C07K 16/241* (2013.01); *C40B 40/10* (2013.01); C07K 2317/34 (2013.01); C07K 2317/52 (2013.01); C07K 2317/56 (2013.01); C07K 2317/622 (2013.01); C07K 2319/00 (2013.01)

(58) Field of Classification Search
None
See application file for complete search history.

(56) References Cited

U.S. PATENT DOCUMENTS

| 4,256,746 A | 3/1981 | Miyashita et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,439,196 A | 3/1984 | Higuchi |
| 4,447,224 A | 5/1984 | De Cant et al. |
| 4,447,233 A | 5/1984 | Mayfield |
| 4,450,254 A | 5/1984 | Isley et al. |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,563,304 A | 1/1986 | Carlsson et al. |
| 4,596,556 A | 6/1986 | Morrow et al. |
| 4,683,192 A | 7/1987 | Nishiyama |
| 4,683,202 A | 7/1987 | Mullis |
| 4,790,824 A | 12/1988 | Morrow et al. |
| 4,800,159 A | 1/1989 | Mullis et al. |
| 4,816,567 A | 3/1989 | Cabilly et al. |
| 4,941,880 A | 7/1990 | Burns |
| 4,965,188 A | 10/1990 | Mullis et al. |
| 5,064,413 A | 11/1991 | McKinnon et al. |
| 5,182,205 A | 1/1993 | Bauer et al. |
| 5,208,020 A | 5/1993 | Chari et al. |
| 5,312,335 A | 5/1994 | Mc Kinnon, Jr. et al. |
| 5,374,548 A | 12/1994 | Caras |
| 5,399,163 A | 3/1995 | Peterson et al. |
| 5,399,331 A | 3/1995 | Loughrey et al. |
| 5,416,016 A | 5/1995 | Low et al. |
| 5,416,064 A | 5/1995 | Chari et al. |
| 5,383,851 A | 6/1995 | Mc Kinnon, Jr. et al. |

(Continued)

FOREIGN PATENT DOCUMENTS

| EP | 0269127 | 6/1998 |
| EP | 1396500 A1 | 3/2004 |

(Continued)

OTHER PUBLICATIONS

Xu (Journal of Molecular Biology, vol. 397, p. 352-360, 2010).*
Paul, Fundamental Immunology, 3rd Edition, 1993, pp. 292-295.*
Bendig M. M. (Methods: A Companion to Methods in Enzymology, 1995; 8:83-93).*
Portolano (The Journal of Immunology, vol. 150, No. 3, p. 880-887, 1993).*
Foreman (Molecule Cancer Therapeutics, vol. 11, No. 7, p. 1411-1420, 2012).*
Bankovich et al. "Structural insight into pre-B cell receptor function", Science 316: 291-294, Apr. 2007.

(Continued)

*Primary Examiner* — Michael Allen
(74) *Attorney, Agent, or Firm* — Cooley LLP

(57) ABSTRACT

The invention concerns constructs and libraries comprising antibody surrogate light chain sequences. In particular, the invention concerns constructs comprising VpreB sequences, optionally partnered with another polypeptide, such as, for example, antibody heavy chain variable domain sequences, and libraries containing the same.

2 Claims, 31 Drawing Sheets

Specification includes a Sequence Listing.

(56) References Cited

U.S. PATENT DOCUMENTS

| | | | |
|---|---|---|---|
| 5,427,908 | A | 6/1995 | Dower et al. |
| 5,474,765 | A | 12/1995 | Thorpe |
| 5,475,982 | A | 12/1995 | Laude-Bousquet |
| 5,480,968 | A | 1/1996 | Kraus et al. |
| 5,585,499 | A | 12/1996 | Chari et al. |
| 5,622,929 | A | 4/1997 | Willner et al. |
| 5,641,869 | A | 6/1997 | Vandlen et al. |
| 5,762,918 | A | 6/1998 | Thorpe |
| 5,824,805 | A | 10/1998 | King et al. |
| 5,846,545 | A | 12/1998 | Chari et al. |
| 6,333,410 | B1 | 12/2001 | Chari et al. |
| 6,337,070 | B1 | 1/2002 | Yoshinobu et al. |
| 6,441,163 | B1 | 8/2002 | Chari et al. |
| 6,716,821 | B2 | 4/2004 | Zhao et al. |
| 6,720,409 | B2 | 4/2004 | Okuno et al. |
| 7,276,497 | B2 | 10/2007 | Chari et al. |
| 7,473,796 | B2 | 1/2009 | Chari et al. |
| 7,612,181 | B2 | 11/2009 | Wu et al. |
| 8,114,967 | B2 | 2/2012 | Bhatt et al. |
| 8,198,417 | B2 | 6/2012 | Steeves et al. |
| 9,169,318 | B2 | 10/2015 | Howowitz et al. |
| 2002/0054882 | A1 | 5/2002 | Yoshinobu et al. |
| 2003/0198637 | A1 | 10/2003 | Tong et al. |
| 2003/0215453 | A1 | 11/2003 | Dedera et al. |
| 2005/0169933 | A1 | 8/2005 | Steeves et al. |
| 2005/0238649 | A1 | 10/2005 | Doronina et al. |
| 2006/0024317 | A1 | 2/2006 | Boyd et al. |
| 2006/0074008 | A1 | 4/2006 | Senter et al. |
| 2006/0147997 | A1 | 7/2006 | Ramakrishnan |
| 2007/0004909 | A1 | 1/2007 | Johnson et al. |
| 2007/0191314 | A1 | 8/2007 | Klucker et al. |
| 2008/0014205 | A1 | 1/2008 | Horowitz et al. |
| 2008/0124345 | A1 | 5/2008 | Rothe |
| 2009/0082213 | A1 | 3/2009 | Horowitz et al. |
| 2009/0098164 | A1* | 4/2009 | Bhatt ............ A61K 47/48776 424/246.1 |
| 2009/0226455 | A1 | 9/2009 | Filvaroff |
| 2009/0274713 | A1 | 11/2009 | Chari et al. |
| 2010/0004139 | A1 | 1/2010 | Bhatt et al. |
| 2010/0040635 | A1 | 2/2010 | Horowitz et al. |
| 2010/0062950 | A1 | 3/2010 | Bhatt et al. |
| 2010/0210034 | A1 | 8/2010 | Bates |
| 2010/0255010 | A1 | 10/2010 | Fuh |
| 2010/0297174 | A1 | 11/2010 | Garcia-Sastre et al. |
| 2011/0256154 | A1 | 10/2011 | Vincent et al. |
| 2012/0123098 | A1 | 5/2012 | Bhatt et al. |
| 2012/0128671 | A1 | 5/2012 | Howowitz et al. |
| 2012/0156217 | A1 | 6/2012 | Setiady et al. |
| 2012/0202713 | A1 | 8/2012 | Bhatt et al. |
| 2012/0294853 | A1 | 11/2012 | McDonagh et al. |
| 2014/0308287 | A1 | 10/2014 | Bhatt et al. |
| 2015/0004162 | A1 | 1/2015 | Kashyap et al. |
| 2015/0011736 | A1 | 1/2015 | Horowitz et al. |
| 2015/0045540 | A1 | 2/2015 | Howowitz et al. |
| 2016/0096882 | A1 | 4/2016 | Howowitz et al. |
| 2016/0354486 | A1 | 12/2016 | Horowitz et al. |

FOREIGN PATENT DOCUMENTS

| | | |
|---|---|---|
| JP | 2011-516423 A | 5/2011 |
| WO | WO 1984/000687 A1 | 3/1984 |
| WO | WO 1997/016208 A1 | 5/1997 |
| WO | WO 2000/073349 A1 | 12/2000 |
| WO | WO 2001/035993 A2 | 5/2001 |
| WO | WO 2001/060402 A2 | 8/2001 |
| WO | WO 2002/030463 A2 | 4/2002 |
| WO | WO 2002/096457 A2 | 12/2002 |
| WO | WO 2004/003019 A2 | 1/2004 |
| WO | WO 2004/010957 A2 | 2/2004 |
| WO | WO 2007/077028 A2 | 7/2007 |
| WO | WO 2007/134327 A2 | 11/2007 |
| WO | WO 2008/028946 A2 | 3/2008 |
| WO | WO 2008/089073 A2 | 7/2008 |
| WO | WO 2008/100624 A2 | 8/2008 |
| WO | WO2008/118970 * | 10/2008 |
| WO | WO 2008/153236 A1 | 12/2008 |
| WO | WO 2009/021754 A2 | 2/2009 |
| WO | WO 2009/079259 A2 | 6/2009 |
| WO | WO 2009/121004 A2 | 10/2009 |
| WO | WO 2009/134976 A1 | 11/2009 |
| WO | WO 2010/006286 A2 | 1/2010 |
| WO | WO 2010/132604 A2 | 11/2010 |
| WO | WO 2010/151808 A1 | 12/2010 |
| WO | WO 2011/071957 A1 | 6/2011 |
| WO | WO 2011/112955 A1 | 9/2011 |
| WO | WO 2011/143307 A1 | 11/2011 |
| WO | WO 2011/153431 A2 | 12/2011 |
| WO | WO 2013/003652 A1 | 1/2013 |
| WO | WO 2013/016714 A1 | 1/2013 |
| WO | WO 2013/096828 A1 | 6/2013 |
| WO | WO 2013/109994 A1 | 7/2013 |

OTHER PUBLICATIONS

Collins et al. "A genome annotation-driven approach to cloning the human ORFeome", Genome Biology 5(10)R84, Epub Sep. 30, 2004.

Database UniProt (online) Immunoglobulin lambda-like polypeptide 1, XP002498605 (1990).

Gauthier et al. "U-surrogate light chain physicochemical interactions of the human preB cell receptor:implications for VH repertoire selection and cell signaling at the preB cell stage", J. Immunology 162:41-50, 1999.

Hagiwara, S. "Transgenic expression of VpreB-3 under the control of the immunoglobulin heavy chain enhancer and SV40 promoter", The Kobe Journal of Medical Sciences 42(1): 43-49, Feb. 1996.

Hirabayashi et al. Kinetic analysis of the interactions of recombinant human VpreBand Ig V domain, J Immunology 155(3): 1218-1228, 1995.

Hollis et al. "Immunoglobulin lambda light-chain-related genes 14.1 and 16.1 are expressed in pre-B cells and may encode the human immunoglobulin omega light-chain protein", Proc. Natl. Acad. Sci. USA 86(14):5552-5556, 1989.

Hollis et al. (PIR database, 1996, accession No. A33911, accessed on Sep. 12, 2012, Score Alignment 3 pages.

Karasuyama et al. "The proteins encoded by the VpreB and _5 pre-B cell-specific genes can associate with each other and with heavy chain", J of Experimental Medicine 172: 969-972, 1990.

Karasuyama et al. "Surrogate light chain in B cell development", Adv. Immunol. 63:1-41, 1996.

Kudo et al. (PIR database, 1987 accession No. A26166, accessed on Jul. 19, 2010 Score Alignment, 4 pages.

Lanig et al. "Three dimentional modeling of a pre B-cell receptor", Molecular Immunology 40(17): 1263-1272, 2004.

Melchers et al. "The surrogate light chain in B-cell development", Immunology Today 14(2):60-68, Feb. 1993.

Melchers et al. "Fit for life in the immune system? Surrogate L chain tests H chains that test L chains", Proc. Natl. Acad. Sci. USA 96:2571-2573, Mar. 1999.

Minegishi et al. "Novel mechanisms control the folding and assembly of 5/14.1 and VpreB to produce an intact surrogate light chain". PNAS 96:3041-3046. 1999.

Xu et al. "Combinatorial surrobody libraries", PNAS 105(31):10756-10761, 2008.

Ada, G.L. and Jones, P.D. "The Immune response to influenza infection", Current topics in Microbiology and Immunology (1986); 128: 1-54.

Adams, Camellia W., et al. "Humanization of a recombinant monoclonal antibody to produce a therapeutic HER dimerization inhibitor, pertuzumab." Cancer Immunology, Immunotherapy (2006); 55.6: 717-727.

Ashkenazi, A., Directing cancer cells to self-destruct with proapoptotic receptor agonists, Nat. Rev. Drug Discov. (2008); 7: 1001-1012.

Bowie, James U., et al. "Deciphering the message in protein sequences: tolerance to amino acid substitutions." Science (1990); 247.4948: 1306-1310.

(56) References Cited

OTHER PUBLICATIONS

Brummell, David A., et al. "Probing the combining site of an anti-carbohydrate antibody by saturation-mutagenesis: role of the heavy-chain CDR3 residues." Biochemistry (1993); 32.4: 1180-1187.
Burks et al, "In vitro scanning saturation mutagenesis of an antibody binding pocket", PNAS 94: 412-417, (1997).
Carlsson et al., "Protein Thiolation and Reversible Protein-Protein Conjugation", Biochem. J., 173:723-737 (1978).
Casset et al. "A peptide mimetic of an anti-CD4 monoclonal antibody by rational design", Biochemical and Biophysical Research Communications (2003); 307: 198-205.
Chen et al. "Selection and analysis of an optimized anti-VEGF antibody: Crystal structure of an affinity-matured Fabin complex with Antigen", Journal of Molecular Biology (1999); 293: 865-881.
Chumsae, et al: "Comparison of methionine oxidation in thermal stability and chemically stressed samples of a fully human monoclonal antibody", Journal of Chromatography (2007); 850: 285-294.
Colman, "Effects of amino acid sequence changes on antibody-antigen interactions", Research in Immunol. (1994); 145: 33-36.
Colman et al., "Structure of the catalytic and antigenic sites in influenza virus neuraminidase", Nature (1983); 303: 41-44.
Couch and Kasel, "Immunity to influenza in man", Annual Reviews in Microbiology (1983); 37.1: 529-549.
Daniel, Claude, et al. "Mapping of linear antigenic sites on the S glycoprotein of a neurotropic murine coronavirus with synthetic peptides: a combination of nine prediction algorithms fails to identify relevant epitopes and peptide immunogenicity is drastically influenced by the nature of the protein carrier." Virology (1994); 202.2: 540-549.
Davies and Riechmann, "Affinity improvement of single antibody VH domains: residues in all three hyper variable regions affect antigen binding", Immunotechnology (1996); 2.3: 169-179.
De Pascalis et al. "Grafting of "Abbreviated" complementarity-determining regions containing specificity-determining residues essential for ligand contact to engineer a less immunogenic humanized monoclonal antibody", The Journal of Immunology (2002); 169: 3076-3084.
Dubowchik and Walker, "Receptor-mediated and enzyme-dependent targeting of cytotoxic anticancer drugs", Pharm. Therapeutics 83:67-123 (1999).
Extended European Search Report for European Application No. EP 13177665.0, dated Jan. 16, 2014, 14 pages.
Francés et al. "A surrogate 15 kDa JC kappa protein is expressed in combination with mu heavy chain by human B cell precursors", EMBO Journal (1994); 13: 5937-5943.
Franklin, Matthew C., et al. "Insights into ErbB signaling from the structure of the ErbB2-pertuzumab complex." Cancer Cell (2004); 5.4: 317-328.
Friedman et al. "Engineering and characterization of a bispecific HER2 × EGFR-binding affibody molecule", Biotechnology and Applied Biochemistry (2009); 54(2): 121-131.
Gocník, et al., "Antibodies specific to the HA2 glycopolypeptide of influenza. A virus haemagglutinin with fusion-inhibition activity contribute to the protection of mice against lethal infection", Journal of General Virology (2007); 88(Part 3): 951-955.
Goudsmit, Japp, "Discovery of a unique set of human monoclonal antibodies active against H5N1." Presentation at 5th International Bird Flu Summit, Sep. 27, 2007, URL link http://investors.crucell.com/C/132631/present 2007 v2.html, 35 pages.
Goudsmit, Japp, "New Directions in Fighting Flu." Presentation at Symposium for 10th Anniversary of Inflexal V, Apr. 26, 2007, 38 pages.
Govorkova, et al., "Immunization with reverse-genetics-produced H5N1 influenza vaccine protects ferrets against homologous and heterologous challenge." Journal of Infectious Diseases (2006); 194.2: 159-167.
Greenspan and Di Cera "Defining epitopes: It's not as easy as it seems." Nature Biotechnology (1999); 17(10): 936-937.
Güssow and Seemann. "[5] Humanization of monoclonal antibodies." Methods in Enzymology (1991); 203: 99-121.
Hanson, et al., "Passive immunoprophylaxis and therapy with humanized monoclonal antibody specific for influenza A H5 hemagglutinin in mice", Respiratory Research (2006); 7: 126, pp. 1-10.
Hashida et al., "More Useful Maleimide Compounds for the Conjugation of Fab' to Horseradish Peroxidase through Thiol Groups in the Hinge", J. Applied Biochem., 56-63 (1984).
Hollis, Gregory F., et al. "Immunoglobulin lambda light-chain-related genes 14.1 and 16.1 are expressed in pre-B cells and may encode the human immunoglobulin omega light-chain protein." Proceedings of the National Academy of Sciences (1989); 86.14: 5552-5556.
Holm et al. "Functional mapping and single chain construction of the anti-cytokeratin 8 monoclonal antibody TSI." Molecular Immunology (2007); 44.6: 1075-1084.
Holt, et al., "Domain antibodies: proteins for therapy", Trends in Biotechnology (2003); 21.11: 484-490.
Horváth, et al. "A Hemagglutinin-Based Multipeptide Construct Elicits Enhanced Protective Immune Response in Mice Against Influenza A Virus Infection", Immunology Letters (1998); 60.2: 127-136.
International Search Report and Written Opinion for International Application No. PCT/US2008/058283, dated Oct. 30, 2008, 11 pages.
International Preliminary Report on Patentability for International Application No. PCT/US2008/058283, dated Sep. 29, 2009, 7 pages.
International Search Report and Written Opinion for International Application No. PCT/US2009/038636, dated Feb. 8, 2010, 21 pages.
International Preliminary Report on Patentability for International Application No. PCT/US2009/038636, dated Sep. 28, 2010, 13 pages.
International Search Report and Written Opinion for International Application No. PCT/US2010/034604, dated Jan. 26, 2011, 21 pages.
International Preliminary Report on Patentability for International Application No. PCT/US2010/034604, dated Nov. 15, 2011, 13 pages.
International Search Report and Written Opinion for International Application No. PCT/US2012/044746, dated Dec. 4, 2012, 10 pages.
International Preliminary Report on Patentability for International Application No. PCT/US2012/044746, dated Jan. 7, 2014, 6 pages.
International Search Report and the Written Opinion for International Application No. PCT/US2012/048730, dated Nov. 6, 2012, 15 pages.
International Preliminary Report on Patentability for International Application No. PCT/US2012/048730, dated Jan. 28, 2014, 7 pages.
International Search Report and the Written Opinion for International Application No. PCT/US2012/071352, dated May 14, 2013, 15 pages.
International Preliminary Report on Patentability for International Application No. PCT/US2012/071352, dated Jun. 24, 2014, 9 pages.
International Search Report and the Written Opinion for International Application No. PCT/US2013/022308, dated Mar. 8, 2013, 9 pages.
International Preliminary Report on Patentability for International Application No. PCT/US2013/022308, dated Jul. 22, 2014, 5 pages.
Jang et al, "The structural basis for DNA binding by an anti-DNA autoantibody", Molecular immunology (1998); 35.18: 1207-1217.
Johnson et al., "Anti-Tumor Activity of CC49-Doxorubicin Immunoconjugates", Anticancer Res. 15:1387-93 (1995).
Kaneko et al., "New Hydrazone Derivatives of Adriamycin and Their Immunoconjugates—a Correlation between Acid Stability and Cytotoxicity", Bioconjugate Chem. 2:133-41 (1991).
Kashap, et al. "Combinatorial, antibody libraries from survivors of the Turkish H5NI avian influenza outbreak reveal virus neutralization strategies", Proceedings of the National Academy of Sciences (2008); 105(16): 5986-5991.

(56) References Cited

OTHER PUBLICATIONS

Kobayashi et al, "Tryptophan H33 plays an important role in pyrimidine (6-4) pyrimidone photoproduct binding by a high-affinity antibody", Protein Engineering (1999); 12.10: 879-884.

Kong, et al., "Successful treatment of avian influenza with convalescent plasma", Hong Kong Med. Journal (2006); 12(6): 489.

Kumar et al, "Molecular Cloning and Expression of the Fabs of Human Autoantibodies in *Escherichia coli*. Determination of the heavy or light chain contribution to the anti-DNA/-Cardiolipin activity of the Fab", J. Biol. Chem. (2000); 275: 35129-35136.

Lamminmaki and Kankare. "Expanding the conformational diversity by random insertions to CDRH2 results in improved anti-estradiol antibodies", J. Mol. Biol., 291: 589-602, (1999).

Lau et al., "Conjugation of Doxorubicin to Monoclonal Anti-carcinoembryonic Antigen Antibody via Novel Thiol-directed Cross-linking Reagents", Bioorg-Med-Chem. 3(10):1299-1304 (1995).

Lau et al., "Novel Doxorubicin-Monoclonal Anti-carcinoembryonic Antigen Antibody Immunoconjugate Activity in vitro", Bioorg-Med-Chem. 3(10): 1305-12 (1995).

Law, et al., "Broadly neutralizing antibodies protect against hepatitis C virus quasispecies challenge", Nature Medicine (2008); 14(1): 25-27.

Lee, et al. "Generation of Bivalent and Bispecific Kringle Single Domains by Loop Grafting as Potent Agonists against Death Receptors 4 and 5." Journal of Molecular Biology (2011); 411(1): 201-219.

Lee, et al., High-affinity human antibodies from phage-displayed synthetic Fab libraries with a single framework scaffold, J. Mol. Biol., 340: 1073-1093, (2004).

Lerner, et al., "Manufacturing immunity to disease in a test tube: the magic bullet realized", Angewandte Chemie International Edition (2006); 45.48: 8106-8125.

Lerner, et. al., "Rare antibodies from combinatorial libraries suggests an S.O.S. component of the human immunological repertoire", Molecular BioSystems (2011); 7.4: 1004-1012.

Lippincott-Schwartz. "Antibodies as Cell Biological Tools." Current Protocols in Cell Biology (2002); 16.0.1-16.0.2.

Liu et al., "New Procedures for Preparation and Isolation of Conjugates of Proteins and a Synthetic Copolymer of D-Amino Acids and Immunochemical Characterization of Such Conjugatest", Biochem., 18:690-697 (1979).

Lu, et al., "Passive immunotherapy for influenza A H5NI virus infection with equine hyperimmune globulin F(ab')2 in mice", Respiratory Research (2006); 7: 43, pp. 1-7.

Luke, et al., "Meta-analysis: Convalescent blood products for Spanish influenza pneumonia: A future H5N1 treatment", Annals of Internal Medicine (2006); 145.8: 599-609.

MacCallum, et al. "Antibody-antigen interactions: contact analysis and binding site topography." Journal of Molecular Biology (1996); 262.5: 732-745.

Mariuzza, et al. "The structural basis of antigen-antibody recognition." Annual Review of Biophysics and Biophysical Chemistry (1987); 16.1: 139-159.

Mårtensson, Inga-Lill, et al. "The pre-B cell receptor checkpoint." FEBS Letters (2010); 584.12: 2572-2579.

Mateu, et al. "Non-additive effects of multiple amino acid substitutions on antigen-antibody recognition." European Journal of Immunology (1992); 22: 1385-1389.

McKeller, Morgan R., and Martinez-Valdez, Hector. "The κ-like pre-B receptor: Surplus biology or a missing link?." Seminars in Immunology (2006); 18(1): 40-43.

Morris, Glenn E. "Epitope Mapping of Protein Antigens by Competition ELISA" In: "The Protein Protocols Handbook", Jan. 1, 1996, (Jan. 1, 1996), Humana Press, Totowa, NJ, XP055007939, ISBN: 978-1-60-327259-9, pp. 595-600, DOI: 10.1007/978-1-60327-259-9_96.

Milutinovic, Snezana, et al. "Development of a novel SurrobodyTM that simultaneously activates both death receptors DR4 and DR5 and induces cancer cell death with high potency." Cancer Research (2013); 73.8 Supplement: 4318-4318.

Neville, Jr. et al., "Enhancement of Immunotoxin Efficacy by Acid-cleavable Cross-linking Agents Utilizing Diphtheria Toxin and Toxin Mutants*", Biol. Chem. 264:14653-14661 (1989).

Okuno, et al., "A common neutralizing epitope conserved between the hemagglutinins of influenza A virus H1 and H2 strains." Journal of Virology (1993); 67.5: 2552-2558.

Oner, et al. "Avian influenza A (H5N1) infection in eastern Turkey in 2006." New England Journal of Medicine (2006); 355.21: 2179-2185.

Palese, P. and Shaw, M.L. "Orthomyxoviridae: The viruses and their replication", Fields Virology (2007); 2: 1647-1689.

Pan, et al., "Methionine oxidation in human IgG2 Fc decreases binding affinities to protein A and FcRn", Protein Science (2009); 18.2: 424-433.

Rangel et al. "Assembly of the kappa preB receptor requires a V kappa-like protein encoded by a germline transcript", Journal of Biological Chemistry (2005); 280.18: 17807-17814.

Robinson et al., "Targeting ErbB2 and ErbB3 with a blspecific single-chain Fv enhances targeting 39 selectivity and induces a therapeutic effect in vitro", British Journal of Cancer (2008); 99.9: 1415-1425.

Rudikoff et al. "Single amino acid substitution altering antigen-binding specificity", Proceedings of the National Academy of Sciences (1982); 79.6: 1979-1983.

Simmons, et al., "Prophylactic and therapeutic efficacy of human monoclonal antibodies against H5NI influenza", PLOS Medicine (2007); 4(5): 928-936.

Smirnov, et al., "Prevention and treatment of bronchopneumonia in mice caused by mouse-adapted variant of avian H5N2 influenza A virus using monoclonal antibody against conserved epitope in the HA stem region", Archives of Virology (2000); 145.8: 1733-1741.

Smirnov, et al., "An epitope shared by the hemagglutinins of HI, H2, H5 and H6 subtypes of influenza A virus", Acta Virologica (1999); 43.4: 237-244.

Smith-Gill et al, "Contributions of immunoglobulin heavy and light chains to antibody specificity for lysozyme and two haptens", The Journal of Immunology (1987); 139.12: 4135-4144.

Song et al. "Light chain of natural antibody plays a dominant role in protein antigen binding", Biochemical and Biophysical Research Communications (2000); 268.2: 390-394.

Thompson et al. "A pro-B-cell stage characterized by germline Ig transcription without surrogate light chain expression." Immunogenetics (1998); 48(5): 305-311.

Thorpe et al., "New Coupling Agents for the Synthesis of Immunotoxins Containing a Hindered Disulfide Bond with Improved Stability in Vivo", Cancer Res. 47:5924-5931 (1987).

Throsby, et al., "Heterosubtypic neutralizing monoclonal antibodies cross-protective against H5NI recovered from human IgM memory B cells", PLoS ONE (2008); 3.12:: e3942, pp. 1-15.

Vajdos et al. "Comprehensive functional maps of the antigen-binding site of an Anti-ErbB2 antibody obtained with shotam scanning mutagenesis", Journal of Molecular Biology (2002); 320. 2: 415-428.

Vermot-Desroches, C. et al. "Characterization of monoclonal antibodies directed against trail or trail receptors." Cellular Immunology (2005); 236.1: 86-91.

Wawrzynczak et al., "In Immunoconjugates: Antibody Conjugates in Radioimagery and Therapy of Cancer," (C.W. Vogel ed., Oxford U. Press (1987).

Ward et al, "Binding activities of a repertoire of single immunoglobulin variable domains secreted from *Escherichia coli*", Nature (1989); 341.6242: 544-546.

Wiley and Skehel. "The structure and function of the hemagglutinin membrane glycoprotein of influenza virus." Ann. Rev. Biochem. (1987); 56:365-394.

Wu et al. "Humanization of a Murine monoclonal antibody by simultaneous optimization of framework and CDR residues", Journal of Molecular Biology (1999); 294.1: 151-162.

Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide", Eur. J. Biochem., 101:395-399 (1979).

(56) References Cited

OTHER PUBLICATIONS

Yuste, L., "Activation of ErbB2 by Overexpression or by Transmembrane Neuregulin Results in Differential Signaling and Sensitivity to Herceptin", Cancer Research (2005); 65.15: 6801-6810.

Zhou, et al., "Treatment with convalescent plasma for influenza A (H5NI) infection", New England Journal of Medicine (2007); 357.14: 1450-1451.

Graduate School of Infection Control Diseases, et al. "Analysis on epitopes of neutralizing antibodies against a highly pathogenic avian influenza H5N1 and preparation of scFv." BMB2007 (30th Meeting of the Molecular Biology Society of Japan/80th Meeting of the Japanese Biochemical Society Joint Meeting) Lecture Abstracts, 2007, p. 851, #4P-1098 (and English translation), 3 pages.
Milutinovic, Snezana, et al. "Dual Agonist Surrobody Simultaneously Activates Death Receptors DR4 and DR5 to Induce Cancer Cell Death." Molecular Cancer Therapeutics (2016); 15.1: 114-124, 11 pages.
Johnson, George, and Wu, Tai Te. "The Kabat database and a bioinformatics example." Antibody Engineering: Methods and Protocols (2004); 248: 11-25.

* cited by examiner

Figure 1

Surrogate Light Chain Alignment with Variable and Constant Lambda Light Chains

```
                             1                                                    CDR1                      65
NM_007128 VPREB1     (1)  MSWAPVLLMLFVYCTGCGPQPVLHQPPAMSSALGTTIRLTCTLRNDHD-IGVYSVYWYQQRPGHP
           Vl1_1b    (1)  ---------------GSQSVLTQPPSVSAAPGQKVTISCSGSSSNI--GNNYVSWYQQLPGTA
CAA01962 Lambda5     (1)  ------------MKLRVGQTLGTIPRQCEVLLLLLIGLVDGVHHILSPSSAERSRA 66         CDR2                                      CDR3            130
NM_007128 VPREB1    (65)  PRFLLRYFSQSDKSQGPQVPPRFSGSKDVARNRGYLISELQPEDEAMYYCAMGARSSEKERER
           Vl1_1b   (47)  PKLLIYDNNK----RPSGIPDRFSGS--KSGTSATLGITGLQTGDEADYYCGTWDSSLSAVVFGG
CAA01962 Lambda5    (46)  VGPGASVGSN---------------------RPSLWALPGRLLFQIIPRGAGPRCSPHRLPSKPQFWYFGG
Vlambda constant     (1)  ----------------------------------------------------------G 131                                                              195
NM_007128 VPREB1   (130)  EWEEEMEPTAARTRVP------------------------------------
CAA01962 Lambda5    (98)  GTQLTILGQPKSDPLVTLFLPSLKNLQPTRPHVVCLVSEFYPGTLVVDWKVDGVPVTQGVETTQP
Vlambda constant     (2)  GTKLTVLRQPKAAPSVTLFPPSSEELQANKATIVCLISDFYPGAVTVAWKADGSPVKAGVETTTP 196                                          242
Vlambda constant    (67)  SKQSNNKYAASSYLSLTPEQWKSHKSYSCQVTHEGSTVEKTVAPTECS
CAA01962 Lambda5   (163)  SKQTNNKYMVSSYLTLISDQWMPHSRYSCRVTHEGNTVEKSVSPAECS
```

- *VPREB1 shares some sequence similarity to classic lambda light chain variable regions*
- *Lambda 5 shares similarity to Vlambda constant regions and Framework region 4*
- *Surrogate light chain has regions that are analogous to CDR regions*

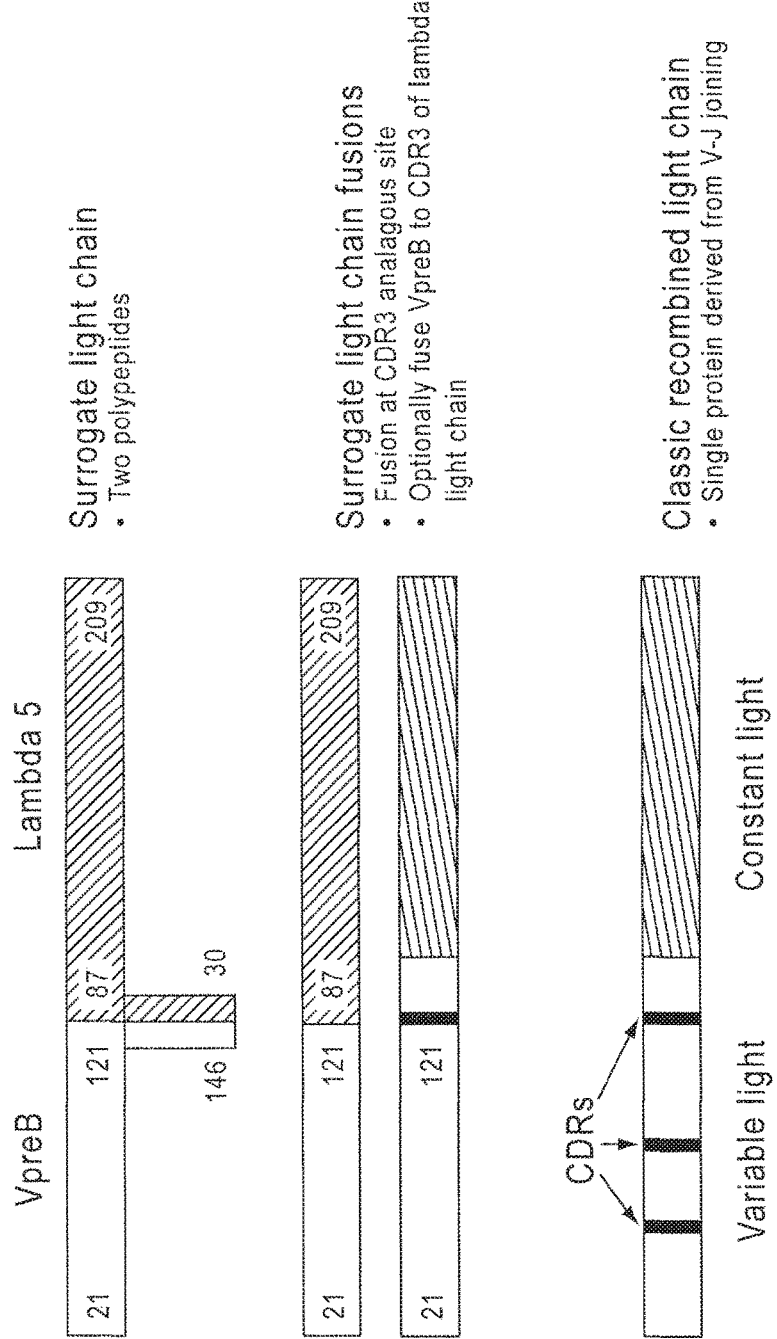

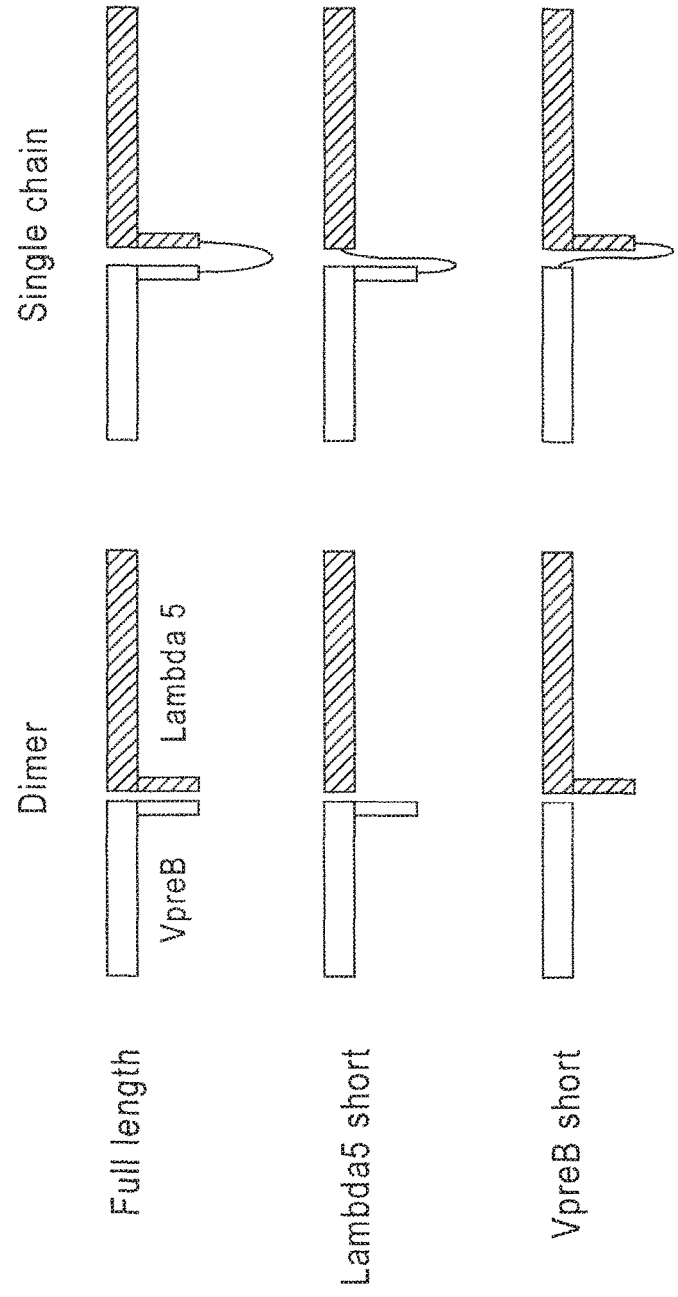

Incorporating Combinatorial Functional Diversity into Surrogate Light Chain Constructs

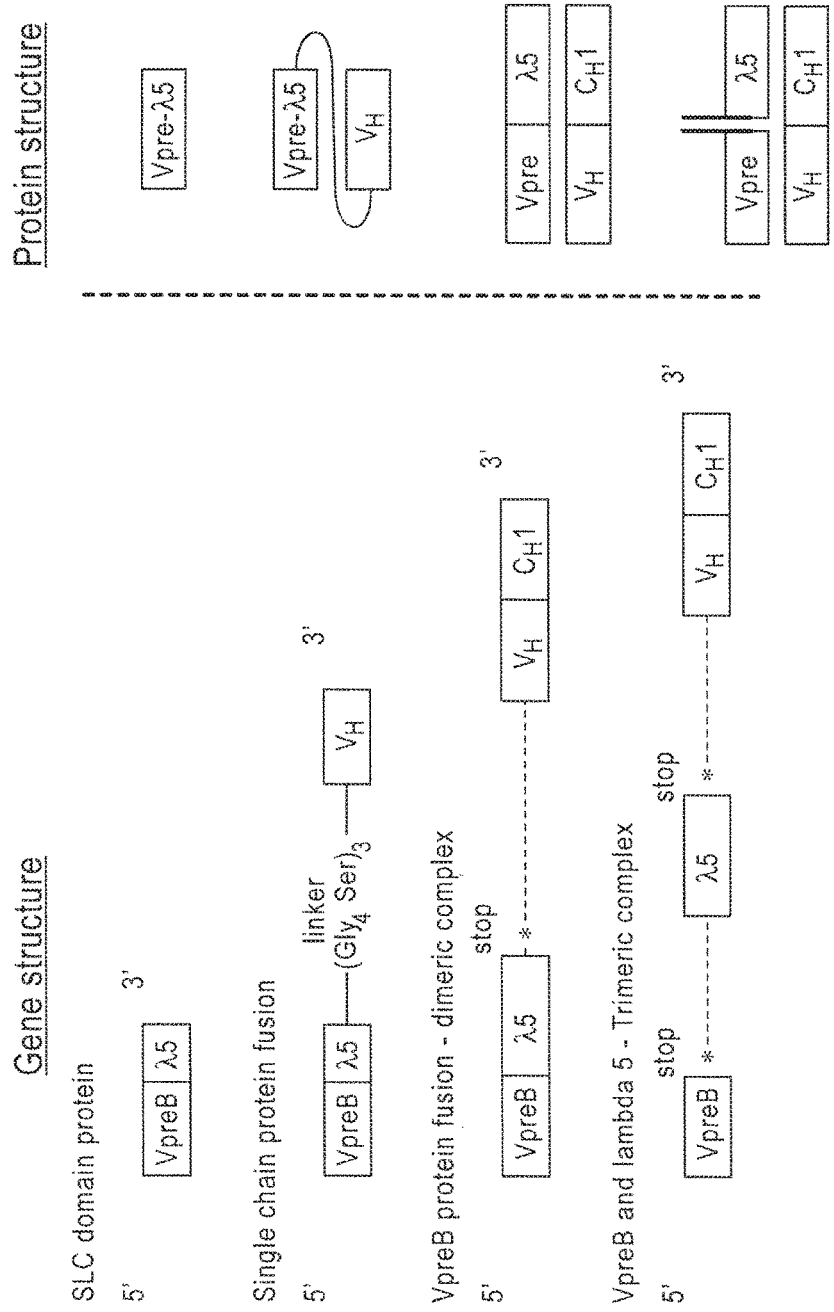

Figure 6

SLC Alignment with VL5 Genes

```
                          1                                                    45
NM_007128 hu VPREB1   (1)  MSWAPVLLMLFVYCTGCGP QVLHQP S LGT I  LTC L N
                 5b   (1)  ------------------- QAVLQPS HS SG V LTCMLS
                 5c   (1)  ------------------- QAVLQPA  S   G SLTC L
                 5e   (1)  ------------------- QVLQP  SS GE LTC LP 46                                                   90
NM_007128 hu VPREB1  (46)  DHD GV S WYQQ PGHPP LLRYFSQS KS QGPQVP PRFSGS
                 5b  (27)  FS GD W RWYQQ PGNPP LL Y S SNK QG VP RFSGS
                 5c  (27)  G R W YQQ PG PPQ LLRYKS S KQQG VP RFSGS
                 5e  (27)  D G N WYQQ PG PF LLY S K QG VP RFSGS 91                                                  135
NM_007128 hu VPREB1  (91)  DV RNRGYLS TS ELQ PEDEA MYYCA GAR E KEERERWEEEM
                 5b  (72)  NE G R S LQ EDEA YYC      N  KT -------
                 5c  (72)  D G I S LQ EDEA YYC          N  -------
                 5e  (72)  D NTG L S LQ EDEA YYC         P N  -------

136      146
NM_007128 hu VPREB1 (136) EPTAARTRVP -
                 5b (106) ----------
                 5c (105) ----------
                 5e (105) ----------
```

VPreB1 shares only 56% - 62% (amino acids 2-97) to VL lambda5 germlines

Figure 7

SLC Alignment with Constant Lambda

```
                        1                                                          50
                        1                                                          50
CAA01962 Lambda5    (1) MKLRVGQTLGTIPRQCEVLLLLLLGLVDGVHHILSPSSAERSRAVGPGA
Lambda constant     (1) --------------------------------------------------

51                                                         100
CAA01962 Lambda5   (51) SVGSNRPSLWALPGRLLFQIIPRGAGPRCSPHRLPSKPQFWVFGG        GTQL
Lambda constant     (1) --------------------------------------------------   GTKL 101                                                         150
CAA01962 Lambda5  (101) T  LGQPK  DPLVTLFLPSLKNLQPT  PH  VCL  S  FYPGT  VVDWKVDGV
Lambda constant     (5) T  LRQPK  APSVTLFPPSSEELQAN    AT  VCL  S  FYPGA  TVAWKADGS 151                                                         200
CAA01962 Lambda5  (151) PVTQGVETTQPSKQ  NNKY MVSSYL  LIS  QWMPHSRYSCRVTHEGNTVE
Lambda constant    (55) PVKAGVETTTPSKQ  NNKY AASSYL  LTP  QWKSHKSYSCQVTHEGSTVE 201  213
CAA01962 Lambda5  (201) K  V  PAECS
Lambda constant   (105) K  V  PTECS
```

Lambda5 shares only 62% (amino acids 97-209) to a constant lambda region

Figure 8

SLC Alignment with Constant Kappa

```
                           1                                                    50
CAA01962 Lambda5     (1)   MKLRVGQTLGTIPRQCEVLILLLLLGLVDGVHHILSPSSAERSRAVGPGA
Kappa constant       (1)   --------------------------------------------------
                           51                                                  100
CAA01962 Lambda5    (51)   SVGSNRPSLWALPGRLLFQIIPRGAGPRCSPHRLPSKPQFWYVFGGGTQL
Kappa constant       (1)   --------------------------------------------------
                           101                                                 150
CAA01962 Lambda5   (101)   TILGQPK DPLVT FLPSIK LQPTRPH VVCL SEFYP GTLVVDWKVDGV
Kappa constant       (1)   ----RTV APSVF FPPSDE LKSGTAS VVCL NNFYP REAKVQWKVDNA
                           151                                                 200
CAA01962 Lambda5   (151)   PV QG-VE TQPSKQTNNK YM SSYLTL ISDQ MPHSRY CRVTHEGN--
Kappa constant      (47)   LQ GNSQE VTEQDSKDST YS SSTLTL SKAD EKHKVY CEVTHQGLSS
                           201        215
CAA01962 Lambda5   (198)   TVEKSVSP EC
Kappa constant      (97)   PVTKSFNR EC
```

Lambda5 shares only 35% (amino acids 105-209) to a constant kappa region

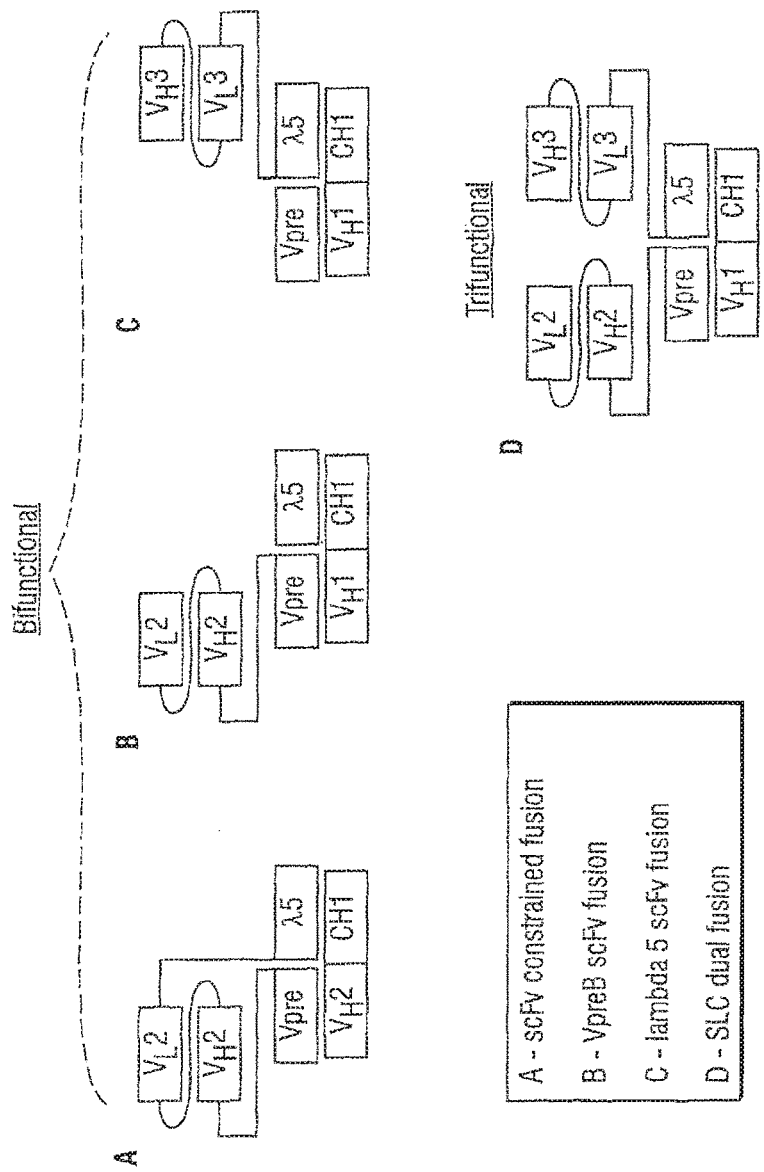

FIG. 10A

```
MSWAPVLLML FVYCTGCGPQ PVLHQPPAMS SALGTTIRLT CTLRNDHDIG
MSWAPVLLML FVYCTGCGPQ PVLHQPPAMS SALGTTIRLT CTLRNDHDIG
VYSVYWYQQR PGHPPRFLLR YFSQSDKSQG PQVPPRFSGS KDVARNRGYL
SISELQPEDE AMYYCAMGAR SSEKEERERE WEEEMEPTAA RTRVP
(human VpreB1; CAG30495; 145 amino acids; SEQ ID NO: 1)
```

```
MAWTSVLLML LAHLTGCGPQ PMVHQPPSAS SSLGATIRLS CTLSNDHNIG
IYSIYWYQQR PGHPPRFLLR YFSHSDKHQG PDIPPRFSGS KDTARNLGYL
SISELQPEDE AVYYCAVGLR SHEKKRMERE WEGEKSYTDL GS
(mouse VpreB2; P13373; 142 amino acids; SEQ ID NO: 2)
```

```
MAWTSVLLML LAHLTGKGTL GVQGFLAPPV ALLCPSDGHA SIFSGCGPQP
MVHQPPSASS SLGATIRLSC TLSNDHNIGI YSIYWYQQRP GHPPRFLLRY
FSHSDKHQGP DIPPRFSGSK DTARNLGYLS ISELQPEDEA VYYCAVGLRS
HEKKRMEREW EGEKSYTDLG S
(mouse VpreB2 splice variant; CAA01964; 171 amino acids; SEQ ID NO: 3)
```

```
MACRCLSFLL MGTFLSVSQT VLAQLDALLV FPGQVAQLSC TLSPQHVTIR
DYGVSWYQQR AGSAPRYLLY YRSEEDHHRP ADIPDRFSAA KDEAHNACVL
TISPVQPEDD ADYYCSVGYG FSP
(human VpreB3; CAG30496; 123 amino acids; SEQ ID NO: 4)
```

```
MKLRVGQTLG TIPRQCEVLL LLLLLGLVDG VHHILSPSSA ERSRAVGPGA
SVGSNRPSLW ALPGRLLFQI IPRGAGPRCS PHRLPSKPQF WYVFGGGTQL
TILGQPKSDP LVTLFLPSLK NLQPTRPHVV CLVSEFYPGT LVVDWKVDGV
PVTQGVETTQ PSKQTNNKYM VSSYLTLISD QWMPHSRYSC RVTHEGNTVE
KSVSPAECS
(human lambda 5; CAA01962; 209 amino acids; SEQ ID NO: 5)
```

```
MRPGTGQGGL EAPGEPGPNL RQRWPLLLLG LAVVTHGLLR PTAASQSRAL
GPGAPGGSSR SSLRSRWGRF LLQRGSWTGP RCWPRGFQSK HNSVTHVFGS
GTQLTVLSQP KATPSVTLFP PSSEELQANK ATLVCLMNDF YPGILTVTWK
ADGTPITQGV EMTTPSKQSN NKYAASSYLS LTPEQWRSRR SYSCQVMHEG
STVEKTVAPA ECS
(human lambda 5-like protein; NP_064455; 213 amino acids; SEQ ID NO: 6)
```

FIG. 10B

Lambda5dT
MRPGTGQGGLEAPGEPGPNLRQRWPLLLLGLAVVTHGSVTHVFGSGTQLTVLSQ
PKATPSVTLFPPSSEELQANKATLVCLMNDFYPGILTVTWKADGTPITQGVEMT
TPSKQSNNKYAASSYLSLTPEQWRSRRSYSCQVMHEGSTVEKTVAPAECS
(SEQ ID NO: 7)

VpreB1d
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPE
DEAMYYCAMGA (SEQ ID NO: 8)

B11 HC-HIS+ (neutralizing anti-influenza heavy chain)
METDTLLLWVLLLWVPGSTGDAQMQLQESGPGLVKPSETLSLTCTVSGYSFDSG
YYWGWLRQPPGKGLEWIGSIYHSRNTYYNPSLKSRVTISVDTSKNQFSLQLSSV
TAADTAVYYCARGTWYSSNLRYWFDPWGKGTLVRVSSASTKGPSVFPLAPSSKS
TSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGHHHHHH
(SEQ ID NO: 9 )

VpreB1-Lambda5 (Fusion1)
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPE
DEAMYYCAMGARSSVTHVFGSGTQLTVLSQPKATPSVTLFPPSSEELQANKATL
VCLMNDFYPGILTVTWKADGTPITQGVEMTTPSKQSNNKYAASSYLSLTPEQWR
SRRSYSCQVMHEGSTVEKTVAPAECA (SEQ ID NO: 10)

VpreB1-CL (Fusion2)
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKSVARNGYLSISELQPED
EAMYYCAMGARSSVTHVFGSGTQLTVLGQPKAAPSVTLFPPSSXELQANKATLV
CLISDFYPGAVTVAWKADSSPVKAGVETTTPSKQSNNKYAASSYLSLTPEQWKS
HRSYSCQVTHEGSTVEKTVAPAECS (SEQ ID NO: 11)

geneIII VpreB1-Lambda5-E tag Fusion (Fusion 1)
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGARSSVTHVFGSGTQLTVLSQPKATPSVTLFPPSSEELQANKAT
LVCLMNDFYPGILTVTWKADGTPITQGVEMTTPSKQSNNKYAASSYLSLTPEQW
RSRRSYSCQVMHEGSTVEKTVAPAECSGAPVPYPDPLEPR (SEQ ID NO: 12)

FIG. 10C geneIII VpreB1-C1-E tag Fusion (Fusion 2)
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGARSSVTHVFGSGTQLTVLRQPKAAPSVTLFPPSSEELQANKAT
LVCLISDFYPGAVTVAWKADGSPVKAGVETTTPSKQSNNKYAASSYLSLTPEQW
KSHKSYSCQVTHEGSTVEKTVAPTECSGAPVPYPDPLEPR  (SEQ ID NO: 13)

pe1B F5 HC gamma-His+ (non-neutralizing anti-influrnza heavy chain)
MKYLLPTAAAGLLLLAAQPAMAQVQLQESGGGLVQPGGSLRLSCAASGFPSSYV
MIWVRQVPGKGLEWVSAIGGSGGSTYYADSVKGRFTISRDNSKNTLYLQMNSLR
ADDTAVYYCVLSPKSYYDNSGIYFDFWGKGTLVRVSSASTKGPSVFPLAPSSLS
TSGGTAALGLVKDYFPEPVTVSWNSGALTSGVHTFPAVLQSSGLYSLSSVVTVP
SSSLGTQTYICNVNHKPSNTKVDKRVEPKSCAAAHHHHHHGEQKLISEEDL
(SEQ ID NO: 14)

pe1B F5 HC mu-His+ (non-neutralizing anti-influrnza IgM heavy chain)
MKYLLPTAAAGLLLLAAQPAMAQVQLQESGGGLVQPGGSLRLSCAASGFPFSSY
VMIWVRQVPGKGLEWVSAIGGSGGSTYYADSVKGRFTISRDNSKNTLYLQMNSL
RADDTAVYYCVLSPKSYYDNSGIYFDFWGKGTLVRVSSGSASAPTLFPLVSCEN
SPSDTSSVAVGCLAQDFLPDSITFSWKYKNNSDISSTRGFPSVLRGGKYAATSQ
VLLPSKDVMQGTDEHVVCKVQHPNGNKEKNVPLPVAAAHHHHHHGEQKLISEED
L  (SEQ ID NO: 15)

GAPVPYPDPLEPR  (SEQ ID NO: 16)

GEQKLISLEEDL  (SEQ ID NO: 17)

geneIII leader VpreB1-E tag full length
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGARSSEKEEREREWEEEMEPTAARTRVPGAPVPYPDPLEPR
(SEQ ID NO: 18)

geneIII leader VpreB1dT
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGA  (SEQ ID NO: 19)

geneIII leader VpreB1dT-E tag
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGAGAPVPYPDPLEPR  (SEQ ID NO: 20)

FIG. 10D

OmpA leader-Lambda5
MKKTAIAIAVALAGFATVAQAALLRPTAASQSRALGPGAPGGSSRSSLRSRWGR
FLLQRGSWTGPRCWPRGFQSKHNSVTHVFGSGTQLTVLSQPKATPSVTLFPPSS
EELQANKATLVCLMNDFYPGILTVTWKADGTPITQGVEMTTPSKQSNNKYAASS
YLSLTPEQWRSRRSYSCQVMHEGSTVEKTVAPAECS (SEQ ID NO: 21)

OmpA leader-Lambda5dT
MKKTAIAIAVALAGFATVAQAASVTHVFGSGTQLTVLSQPKATPSVTLFPPSSE
ELQANKATLVCLMNDFYPGILTVTWKADGTPITQGVEMTTPSKQSNNKYAASSY
LSLTPEQWRSRRSYSCQVMHEGSTVEKTVAPAECS (SEQ ID NO: 22)

GLP-1 VpreB1 full length
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPE
DEAMYYCAMGARSSEKEEREREWEEEMEPTAARTRVPHAEGTFTSDVSSYLEGQ
AAKEFIAWLVKGR (SEQ ID NO: 23)

GLP-1 VpreB1dT
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPE
DEAMYYCAMGAHAEGTFTSDVSSYLEGQAAKEFIAWLVKGR (SEQ ID NO: 24)

GLP-1 Lambda5 full length
MRPGTGQGGLEAPGEPGPNLRQRWPLLLLHAEGTFTSDVSSYLEGQAAKEFIAW
LVKGRGLAVVTHGLLRPTAASQSRALGPGAPGGSSRSSLRSRWGRFLLQRGSWT
GPRCWPRGFQSKHNSVTHVFGSGTQLTVLSQPKATPSVTLFPPSSEELQANKAT
LVCLMNDFYPGILTVTWKADGTPITQGVEMTTPSKQSNNKYAASSYLSLTPEQW
RSRRSYSCQVMHEGSTVEKTVAPAECS (SEQ ID NO: 25)

GLP-1 Lambda5dT
MRPGTGQGGLEAPGEPGPNLRQRWPLLLLGHAEGTFTSDVSSYLEGQAAKEFIA
WLVKGRLAVVTHGSVTHVFGSGTQLTVLSQPKATPSVTLFPPSSEELQANKATL
VCLMNDFYPGILTVTWKADGTPITQGVEMTTPSKQSNNKYAASSYLSLTPEQWR
SRRSYSCQVMHEGSTVEKTVAPAECS (SEQ ID NO: 26)

Detection of Surrogate Light Chains and Complexed Heavy Chains

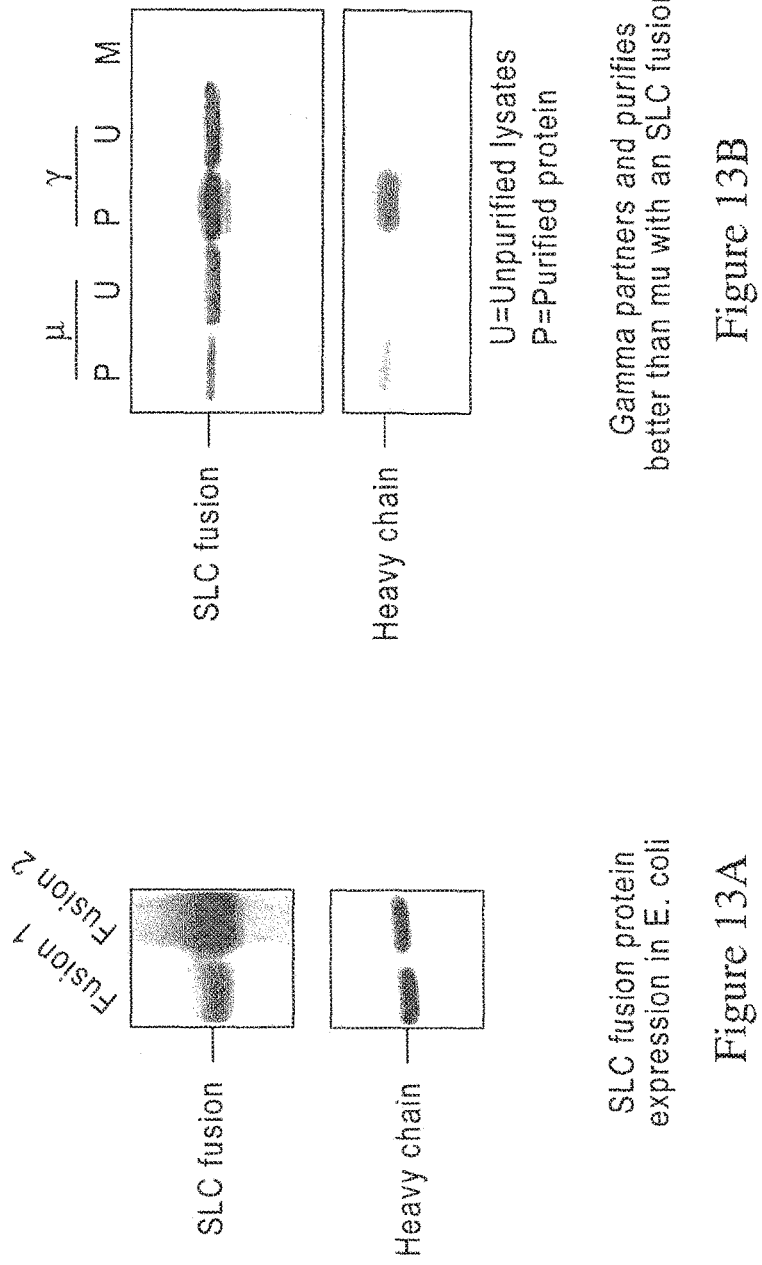

Phage surrobody capture ELISA via anti-phage detection

*Phage expressing either surrogate light chain fusions are immobilized via stable complexes with heavy chain fragments fused to m13 gene III*

Figure 16A

Supernatants of Mammalian Expressed Surrobody SLC Variants Contain Stable Complexes that Bind Viral Target Trimer antigen binding / Heavy chain detection

Figure 16B

VpreB1 detection

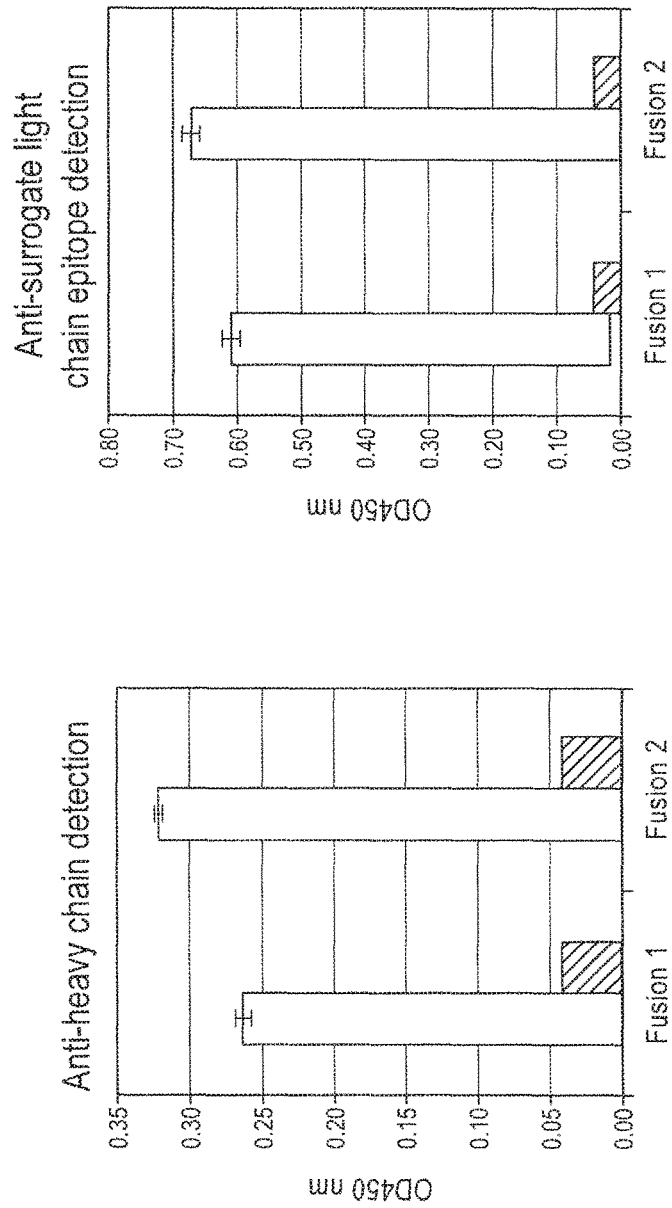

Figure 18

Surrobody SLC Fusion Phage Paired with Neutralizing Heavy Chain Readily Binds H5 HA Antigen

Figure 19

Surrobody variant pahge paired with neutralizing heavy chain binds antigen

Figure 20

| Number of transformants | Library | Round of panning (fold enrichment) | Percent positive clones |
|---|---|---|---|
| $3.84 \times 10^7$ | Fusion 1 - Influenza | 1 (5x) | 79% |
| | Fusion 1 - Influenza | 2 (97x) | 95% |
| $7.80 \times 10^7$ | Fusion 2 - Influenza | 1 (20x) | 95% |
| | Fusion 2 - Influenza | 2 (48x) | 99% |

FIG. 21A

Clonal analysis of Round 1 Fusion 1 library clones
Lysate ELISA_Rd1 Fusion 1-Flu (p421)

Clonal analysis of Round 1 Fusion 2 library clones
Lysate ELISA_Rd1 Fusion 2-Flu (p422)

☐ H5N1 virus coat/aE detect
▨ Uncoated/aE detect

CONSTRUCTS AND LIBRARIES COMPRISING ANTIBODY SURROGATE LIGHT CHAIN SEQUENCES

CROSS-REFERENCE TO RELATED APPLICATIONS

This application is a continuation of U.S. application Ser. No. 13/371,347, filed Feb. 10, 2012, now abandoned, which is a continuation of U.S. application Ser. No. 12/056,151, filed Mar. 26, 2008 and issued as U.S. Pat. No. 8,114,967, which claims the benefit of U.S. Provisional Application Ser. No. 60/920,568, filed Mar. 27, 2007, the entire disclosures of which are incorporated herein by reference.

DESCRIPTION OF THE TEXT FILE SUBMITTED ELECTRONICALLY

The contexts of the text file submitted electronically herewith are incorporated herein by reference in their entirety: A computer-readable format copy of the Sequence Listing (file name: i2PH-007_04US_Seqlist.txt, date recorded: Jan. 10, 2017, file size: 50.8 kb).

FIELD OF THE INVENTION

The present invention concerns constructs and libraries comprising antibody surrogate light chain sequences. In particular, the invention concerns constructs comprising VpreB sequences, optionally partnered with another polypeptide, such as, for example, antibody heavy chain variable domain sequences, and libraries containing the same.

BACKGROUND OF THE INVENTION

Antibody (Ig) molecules produced by B-lymphocytes are built of heavy (H) and light (L) chains. The amino acid sequences of the amino terminal domains of the H and L chains are variable ($V_H$ and $V_L$), especially at the three hypervariable regions (CDR1, CDR2, CDR3) that form the antigen combining site. The assembly of the H and L chains is stabilized by a disulfide bond between the constant region of the L chain ($C_L$) and the first constant region of the heavy chain (C.sub.H1) and by non-covalent interactions between the $V_H$ and $V_L$ domains.

In humans and many animals, such as mice, the genes encoding the antibody H and L chains are assembled by stepwise somatic rearrangements of gene fragments encoding parts of the V regions. Various stages of B lymphocyte development are characterized by the rearrangement status of the Ig gene loci (see, e.g. Melchers, F. & Rolink, A., B-Lymphocyte Development and Biology, Paul, W. E., ed., 1999, Lippincott, Philadephia).

Precursors of B cells (pre-B cells) have been identified in the bone marrow as lymphocytes that produce µ heavy chains but instead of the fully developed light chains express a set of B lineage-specific genes called VpreB(1-3) and λ5, respectively.

The main isoform of human VpreB1 (CAG30495) is a 145 aa-long polypeptide (SEQ ID NO: 1). It has an Ig V domain-like structure, but lacks the last β-strand (β7) of a typical V domain, and has a carboxyl terminal end that shows no sequence homologies to any other proteins. VpreB2 has several isoforms, including a 142-amino acid mouse VpreB2 polypeptide (P13373; SEQ ID NO: 2), and a 171-amino acid long splice variant of the mouse VPreB2 sequence (CAA019641 SEQ ID NO: 3). VpreB1 and VpreB2 sequences have been disclosed in EP 0 269 127 and U.S. Pat. No. 5,182,205; Collins et al., Genome Biol. 5(10):R84 (2004); and Hollins et al., Proc. Natl. Acad. Sci. USA 86(14):5552-5556 (1989). The main isoform of human VpreB3 (SEQ ID NO: 4) is a 123 amino acid long protein (CAG30496), disclosed in Collins et. al., Genome Biol. 5(10):R84 (2004).

VpreB(1-3) are non-covalently associated with another protein, λ5. The human λ5 is a 209-amino acid polypeptide (CAA01962; SEQ ID NO: 5), that carries an Ig C domain-like structure with strong homologies to antibody light chains and, towards its amino terminal end, two functionally distinct regions, one of which shows strong homology to the β7 strand of the Vλ domains. A human λ5-like protein has 213 amino acids (NP_064455; SEQ ID NO: 6) and shows about 84% sequence identity to the antibody λ light chain constant region.

For further details, see the following review papers: Karasuyama et al., Adv. Immunol. 63:1-41 (1996); Melchers et al., Immunology Today 14:60-68 (1993); and Melchers, Proc. Natl. Acad. Sci. USA 96:2571-2573 (1999).

The VpreB and λ5 polypeptides together form a non-covalently associated, Ig light chain-like structure, which is called the surrogate light chain or pseudo light chain. On the surface of early preB cells, the surrogate light chain is disulfide-linked to membrane-bound Ig µ heavy chain in association with a signal transducer CD79a/CD79b heterodimer to form a B cell receptor-like structure, the so-called preB cell receptor (preBCR).

SUMMARY OF THE INVENTION

In one aspect, the invention concerns polypeptides comprising a VpreB sequence or a λ5 sequence conjugated to a heterogeneous amino acid sequence, wherein the polypeptides are capable of binding to a target.

In a preferred embodiment, the polypeptide comprises a VpreB sequence, where VpreB may be any native VpreB, including human VpreB1 (SEQ ID NO: 1), mouse VpreB2 (SEQ ID NO: 2 and 3) and human VpreB3 (SEQ ID NO: 4), or a homologue thereof in another mammalian species, or a fragment or variant thereof, provided that the polypeptide retains the ability to bind to a target.

In a preferred embodiment, the heterogeneous amino acid sequence is a λ5 sequence, which may be any native λ5 sequence, or any fragment or variant thereof, including the native human λ5 sequence of SEQ ID NO: 5, the human λ5-like sequence of SEQ ID NO: 6, and fragments and variants thereof.

The VpreB sequence and the heterogeneous amino acid sequence, e.g. the λ5 sequence, may be directly fused to each other, or may be non-covalently associated. In the former case, the fusion preferably takes place at or around the CDR3 analogous regions of VpreB and λ5, respectively.

In another embodiment, the heterogeneous amino acid sequence is or comprises an antibody chain variable region sequence. In a particular embodiment, the antibody light chain variable region sequence is fused to the VpreB sequence at a site analogous to an antibody light chain CDR3 region. In another embodiment, the fusion is between the CDR3 region of an antibody light chain and the CDR3 analogous region of a VpreB. In all embodiments, the antibody light chain can be a λ chain or a κ chain.

In particular embodiments, the polypeptides herein, including, without limitation VpreB-λ5 conjugates (including fusions, other covalent linkage, and non-covalent associations), and VpreB-antibody light chain conjugates, may be further associated with a sequence comprising an antibody heavy chain variable region sequence, such as an antibody heavy chain variable region, or a complete antibody heavy chain, including a variable region.

When the polypeptide comprises a λ5 sequence, λ5 may be any native λ5, including human λ5 of SEQ ID NO: 5 and human λ5-like protein of SEQ ID NO: 6, or a homologue in another mammalian species, or any fragment or variant thereof, provided that the polypeptide retains the ability to bind to a target. In a particular embodiment, the heterogenous amino acid sequence conjugated to the λ5 sequence is a VpreB sequence.

In the polypeptide constructs of the present invention, the VpreB and λ5 sequences, if both present, may be conjugates by any means, including direct fusion, covalent linkage by a linker sequence (e.g. a peptide linker), and non-covalent association.

In a particular embodiment, a fusion of VpreB sequence and a λ5 sequence is conjugated town antibody heavy chain sequence by non-covalent association, to form a dimeric complex.

In another embodiment, a trimeric complex is formed by non-covalent association of a VpreB sequence, a λ5 sequence and an antibody heavy chain sequence. In certain embodiments, in these structures, which are also referred to as variant surrogate light chain structures or "SURROBODY™ variants," the characteristic tails (appendages) of one or both of the VpreB and λ5 portions may be (but do not have to be) retained. It is possible to attach additional functionalities to such appendages. In addition, in various embodiments, beneficial appendage fusions can be designed and made in order to improve various properties of the constructs, such as PK and/or potency.

In all embodiments, when an antibody heavy chain comprising variable region sequences present, the polypeptide of the present invention and the antibody heavy chain variable region sequences may bind to the same or to different targets.

In another aspect, the invention concerns a library of such polypeptides.

In yet another aspect, the invention concerns a library of such polypeptides associated with antibody heavy chains or fragments thereof comprising variable region sequences.

In a further aspect, the invention concerns a library comprising a collection of surrogate light chain sequences optionally associated with antibody heavy chain variable region sequences.

In all aspects, the library may be in the form of a display, such as, for example, a phage display, bacterial display, yeast display, ribosome display, mRNA display, DNA display, display on mammalian cells, spore display, viral display, display based on protein-DNA linkage, or microbead display.

The invention further concerns various uses of such polypeptides and libraries containing such polypeptides, for example, to design or select antibody-like molecules with desired binding specificities and/or binding affinities, which have important therapeutic applications.

BRIEF DESCRIPTION OF THE DRAWINGS

FIG. 1 shows the alignment of human VpreB1 (SEQ ID NO: 1) and human λ5 (SEQ ID NO: 5) with antibody λ chain variable (SEQ ID NO: 27) and constant regions (SEQ ID NO: 28). VpreB1 shares same sequence similarity to antibody λ chain variable regions, while λ5 shares some similarly to antibody λ chain constant regions and framework region 4. The boxed regions identify VpreB1 and λ5 sequences that are similar to antibody λ chain CDR1, CDR2 and CDR3 regions, respectively.

FIG. 2 is a schematic illustration of a surrogate light chain formed by VpreB and λ5 sequences, illustrative fusion polypeptides comprising surrogate light chain sequences, and an antibody light chain structure derived from V-J joining.

FIG. 3 is a schematic illustration of various surrogate light chain deletion and single chain constructs.

FIG. 5 shows the gene and protein structures of various illustrative surrogate light chain constructs including an SLC domain protein, a single chain fusion protein (comprising an SLC domain protein fused to a heavy chain variable domain by a (Gly$_4$Ser)$_3$ linker (SEQ ID NO: 35)), a VpreB protein fusion-dimeric complex, and a VpreB and lambda 5-trimeric complex.

FIG. 6 is the alignment of human VpreB1 (SEQ ID NO: 1, top sequence) with antibody λ5 light chain variable region germline sequences (SEQ ID NOs: 29 (second from top), 30 (second from bottom), and 31 (bottom sequence), respectively). Regions with the highest degree of sequence similarity are boxed. As shown in the figure, VpreB1 shows only 56%-62% (amino acids 2 to 97) sequence identity to the λ5 light chain variable region germline sequences.

FIG. 7 is the alignment of a λ5 sequence (SEQ ID NO: 5) with an antibody λ light chain constant region sequence (SEQ ID NO: 32). As shown in the figure, the aligned λ5sequence shows only 62% (amino acids 97 to 209) sequence identity to the corresponding antibody λ light chain constant region sequences.

FIG. 8 is the alignment of a λ5 sequence (SEQ ID NO: 5) with antibody κ light chain constant region sequence (SEQ ID NO: 33). As shown in the figure, the aligned λ5 sequence shows only 35% (amino acids 105 to 209) sequence identity to the corresponding antibody κ light chain constant region sequence.

FIG. 9A-FIG. 9D illustrate various representative ways of adding functionality to surrogate light chain (SLC) components.

FIGS. 10A-10D show the human VpreB1 sequence of SEQ ID NO: 1, the mouse VpreB2 sequences of SEQ ID NOS: 2 and 3; the human VpreB3 sequence of SEQ ID NO: 4, the human λ5 sequence of SEQ D NO: 5 and the human λ5-like protein sequence of SEQ ID NO: 6, and sequences of various constructs used in the examples.

FIG. 13A-FIG. 13B: SLC fusion proteins express and secrete well into the periplasm of E. coli and are best partnered with heavy chain CH1 from IgG1 rather than 1 gM. FIG. 13A: SCL fusion protein expression in E. coli. FIG. 13B: IgG1 gamma chain partners and purifies better than 1 gM μ chain with an SLC fusion.

FIG. 16A-FIG. 16B: Purified surrogate light chain constructs expressed in mammalian cells contain stable complexes that bind viral antigen.

FIG. 17A-FIG. 17B: Antigen binding with *E. coli* periplasmic lysates.

FIG. 18: Surrogate light chain fusion construct phage paired with neutralizing heavy chain readily binds H5 HA antigen.

FIG. 19: Surrogate light chain construct phage paired with neutralizing heavy chain binds antigen.

FIG. 20: Table summarizing the results of phage display experiments.

Figure 21B:
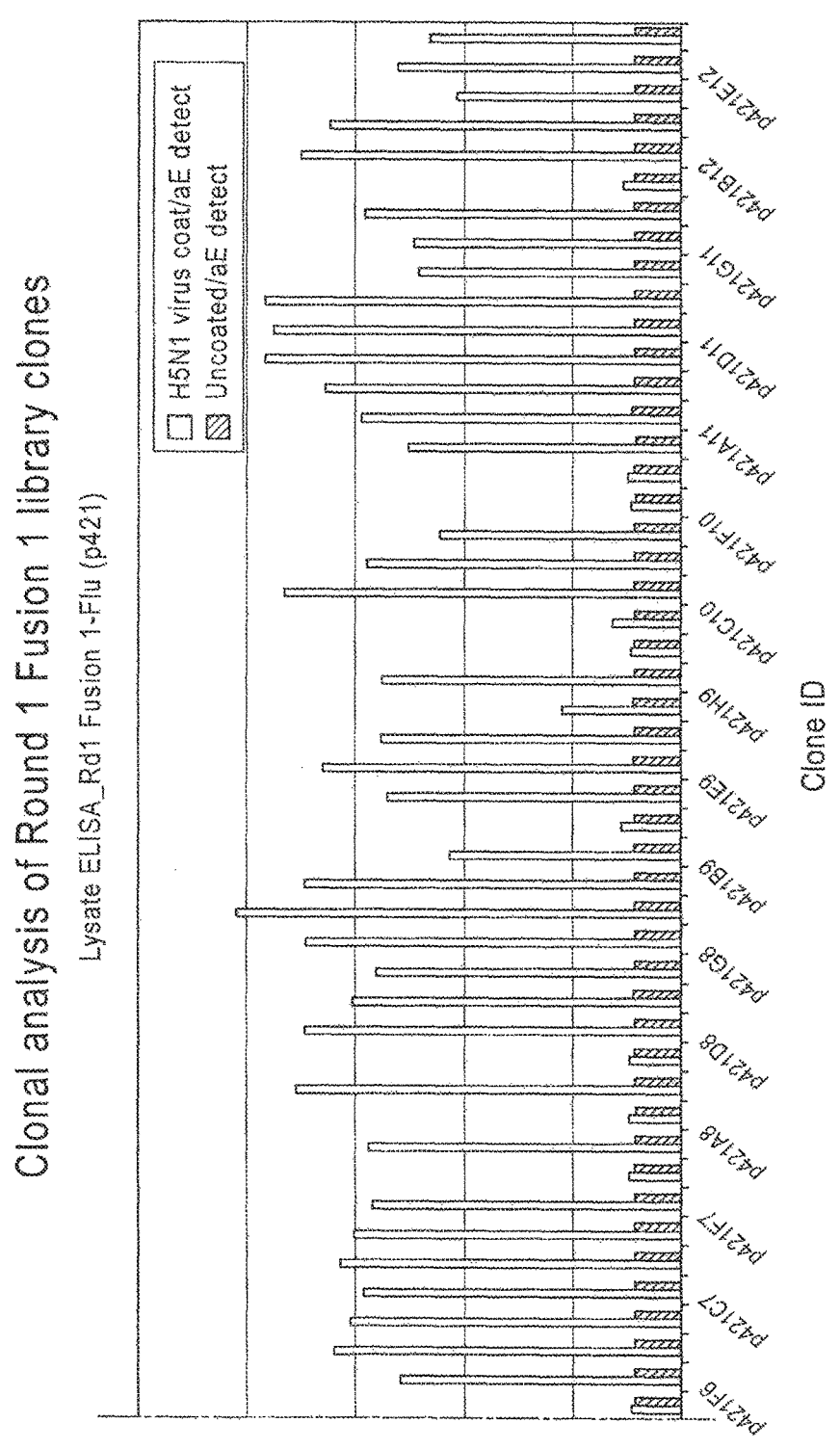
Figure 21D:
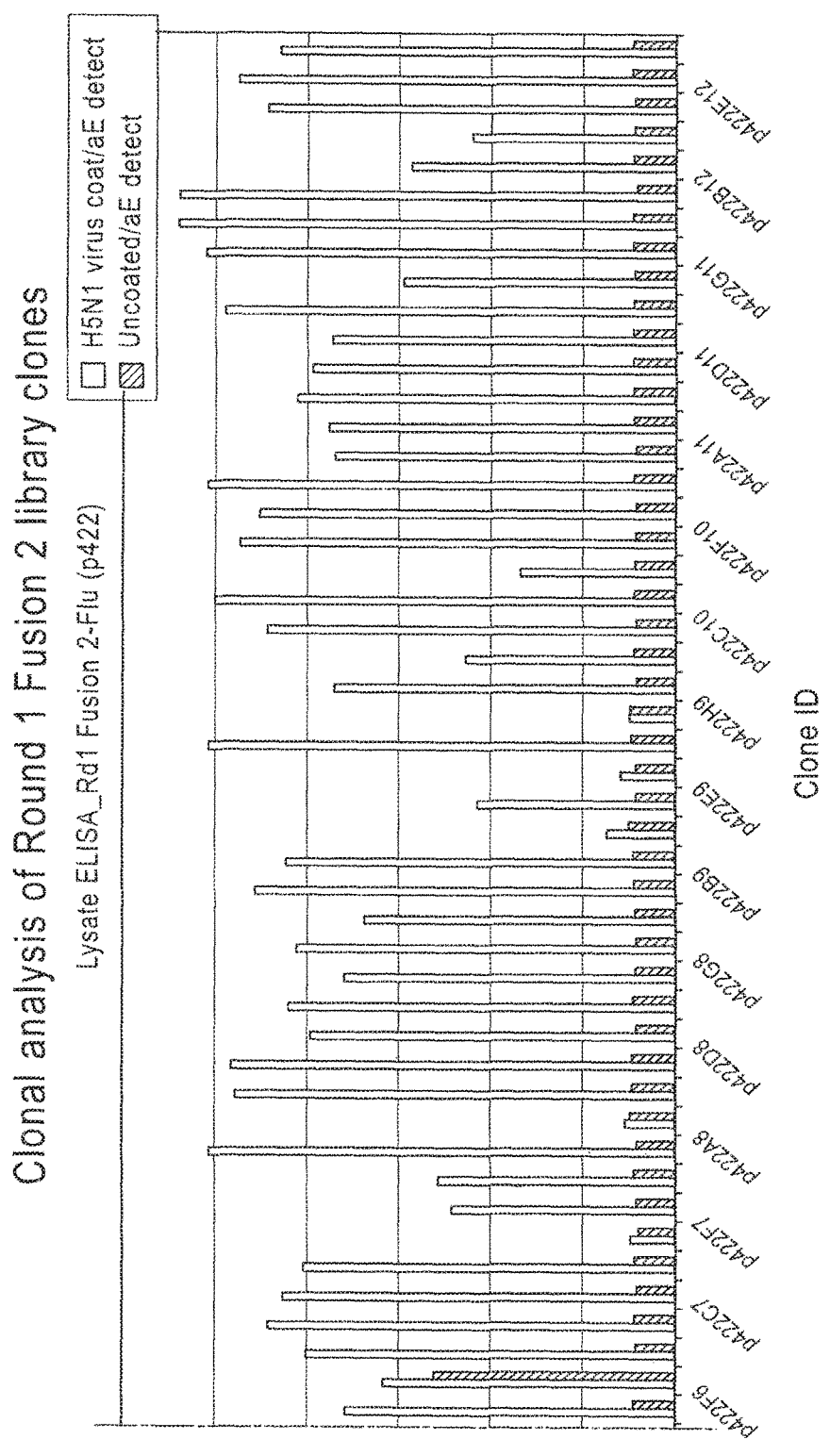
Figure 22B:
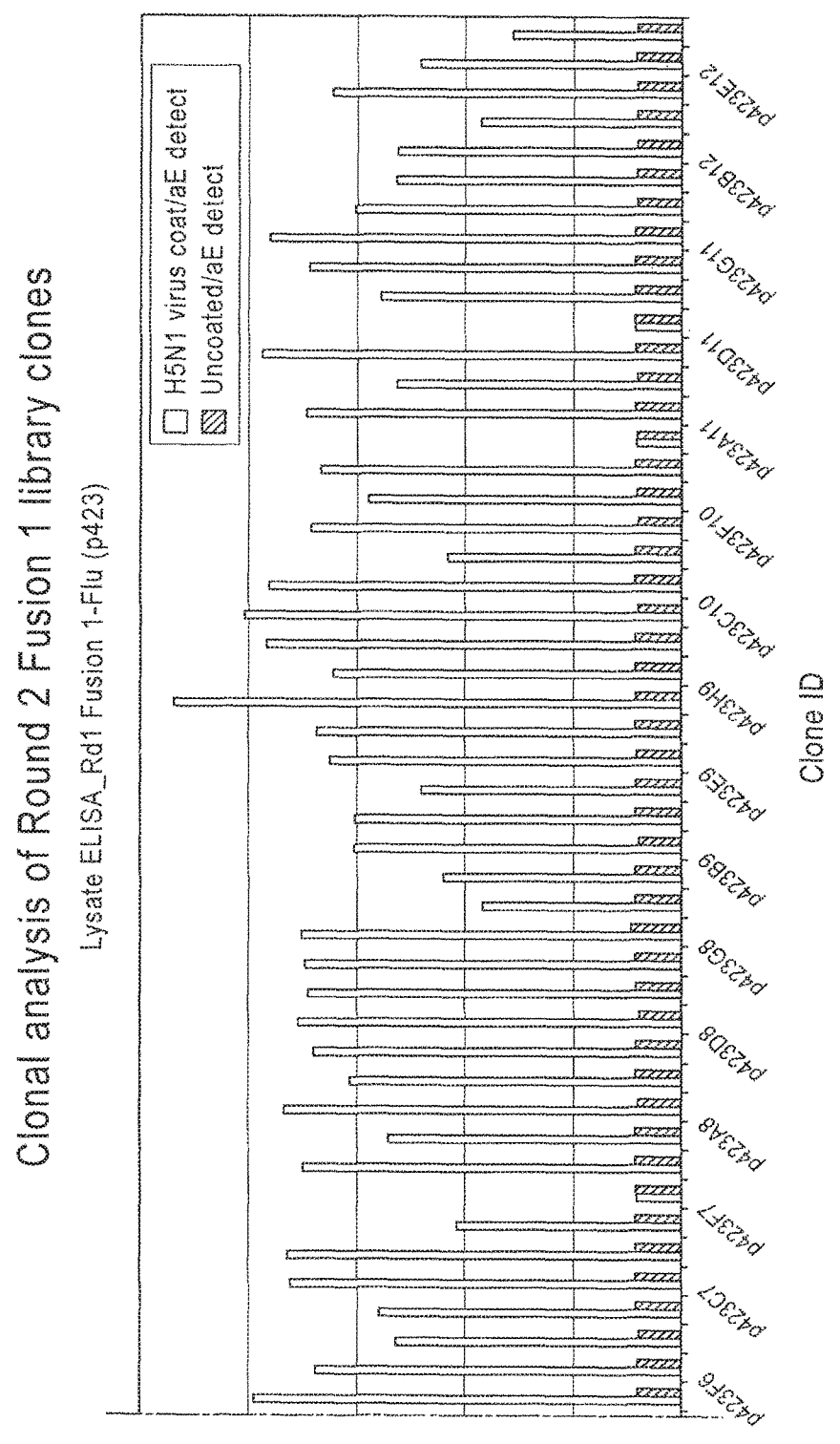

FIGS. 21A-21D and FIGS. 22A-22D: Results of clonal analysis of rounds 1 and 2 of surrogate light chain fusions 1 and 2.

DETAILED DESCRIPTION OF THE INVENTION

A. Definitions

Figure 4:
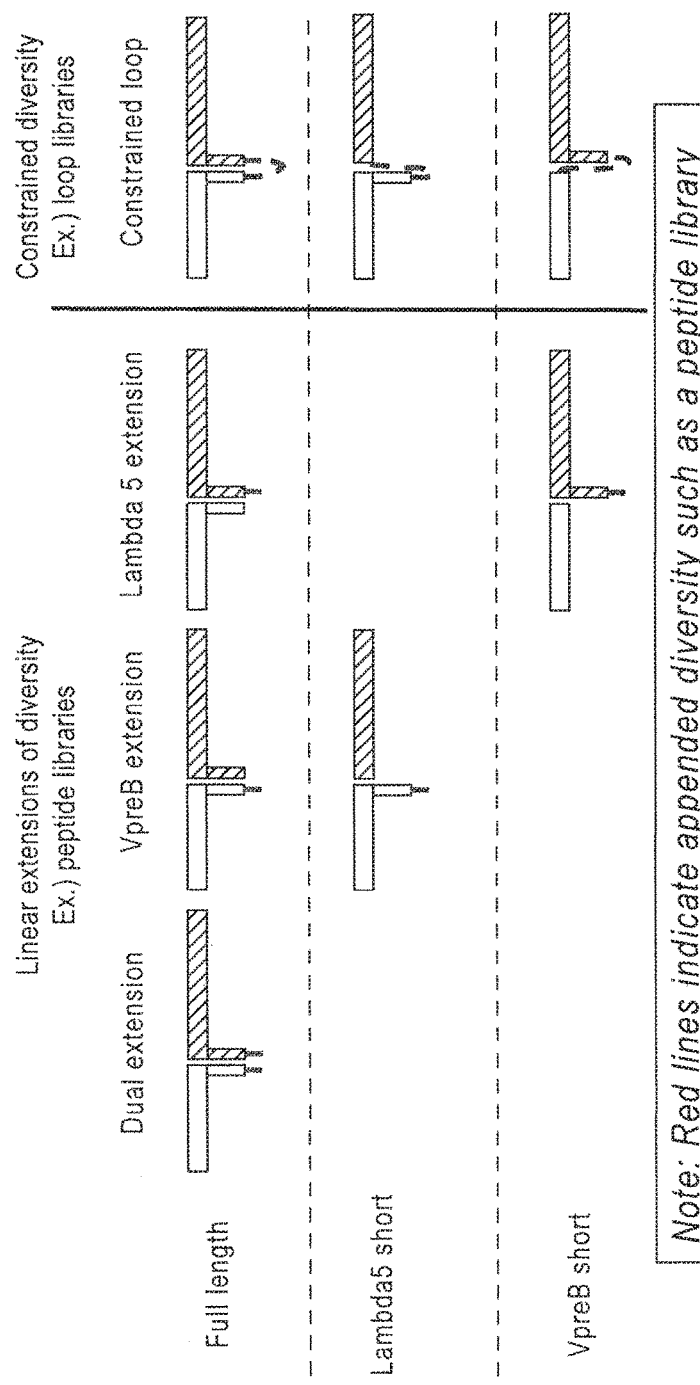
FIG. 4 schematically illustrates the incorporation of combinational functional diversity into surrogate light chain constructs.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "surrogate light chain," as used herein, refers to a dimer formed by the non-covalent association of a VpreB and a λ5 protein.

The term "VpreB" is used herein in the broadest sense and refers to any native sequence or variant VpreB polypeptide, specifically including, without limitation, human VpreB1 of SEQ ID NO: 1, mouse VpreB2 of SEQ ID NOS: 2 and 3, human VpreB3 of SEQ ID NO: 4 and isoforms, including splice variants and variants formed by posttranslational modifications, other mammalian homologues thereof, as well as variants of such native sequence polypeptides.

The term "λ5" is used herein in the broadest sense and refers to any native sequence or variant λ5 polypeptide, specifically including, without limitation, human λ5 of SEQ ID NO: 5, human λ5-like protein of SEQ ID NO: 6, and their isoforms, including splice variants and variants formed by posttranslational modifications, other mammalian homologous thereof, as well a variants of such native sequence polypeptides.

The terms "variant VpreB polypeptide" and "a variant of a VpreB polypeptide" are used interchangeably, and are defined herein as a polypeptide differing from a native sequence VpreB polypeptide at one or more amino acid positions as a result of an amino acid modification. The "variant VpreB polypeptide," as defined herein, will be different from a native antibody λ or κ light chain sequence, or a fragment thereof. The "variant VpreB polypeptide" will preferably retain at least about 65%, or at least about 70%, or at least about 75%, or at least about 80%, or at least about 85%, or at least about 90%, or at least about 95%, or at least about 98% sequence identity with a native sequence VpreB polypeptide. In another preferred embodiment, the "variant VpreB polypeptide" will be less then 95%, or less than 90%, or less then 85%, or less than 80%, or less than 75%, or less then 70%, or less than 65%, or less than 60% identical in its amino acid sequence to a native antibody λ or κ light chain sequence. Variant VpreB polypeptides specifically include, without limitation, VpreB polypeptides in which the non-Ig-like unique tail at the C-terminus of the VpreB sequence is partially or completely removed.

The terms "variant λ5 polypeptide" and "a variant of a λ5 polypeptide" are used interchangeably, and are defined herein as a polypeptide differing from a native sequence λ5 polypeptide at one or more amino acid positions as a result of an amino acid modification. The "variant λ5 polypeptide," as defined herein, will be different from a native antibody λ or κ light chain sequence, or a fragment thereof. The "variant λ5 polypeptide" will preferably retain at least about 65%, or at least about 70%, or at least about 75%, or at least about 80%, or at least about 85%, or at least about 90%, or at least about 95%, or at least about 98% sequence identity with a native sequence λ5 polypeptide. In another preferred embodiment, the "variant λ5 polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant λ5 polypeptides specifically include, without limitation, λ5 polypeptides in which the unique tail at the N-terminus of the λ5 sequence is partially or completely removed.

Percent amino acid sequence identity may be determined using the sequence comparison program NCBI-BLAST2 (Altschul et al., Nucleic Acids Res. 25:3389-3402 (1997)). The NCBI-BLAST2 sequence comparison program may be downloaded from website of the National Center for Biotechnology Information (NCBI) or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "VpreB sequence" is used herein to refer to the sequence of "VpreB," as hereinabove defined, or a fragment thereof.

The term "λ5 sequence" is used herein to refers to the sequence of "λ5," as hereinabove defined, or a fragment thereof.

The term "surrogate light chain sequence," as defined herein, means any polypeptide sequence that comprises a "VpreB sequence" and/or a "λ5 sequence," as hereinabove defined. The "surrogate light chain sequence," as defined herein, specifically includes, without limitation, the human VpreB1 sequence of SEQ ID NO 1, the mouse VpreB2 sequences of SEQ ID NOS: 2 and 3, and the human VpreB3 sequence of SEQ ID NO: 4, and their various isoforms, including splice variants and variants formed by posttranslational modifications, homologues thereof in other mammalian species, as well as fragments and variants thereof. The term "surrogate light chain sequence" additionally includes, without limitation, the human λ5 sequence of SEQ ID NO: 5, the human λ5-like sequence of SEQ ID NO: 6, and their isoforms, including splice variants and variants formed by posttranslational modifications, homologues thereof in other mammalian species, as well as fragments and variants thereof. The term "surrogate light chain sequence" additionally includes a sequence comprising both VpreB and λ5 sequences as hereinabove defined.

For the three-dimensional structure of die pre-B-cell receptor (preBCR), including the structure of the surrogate light chain (SCL) and its components see, e.g. Lanig et al., Mol. Immunol. 40(17): 1263-72 (2004).

The "surrogate light chain sequence" may be optionally conjugated to a heterogeneous amino acid sequence, or any other heterogeneous component, to form a "surrogate light chain construct" herein. Thus, the term, "surrogate light chain construct" is used in the broadest sense and includes any and all additional heterogeneous components, including a heterogeneous amino acid sequence, nucleic acid, and other molecules conjugated to a surrogate light chain sequence, wherein "conjugation" is defined below. A "surrogate light chain construct" is also referred herein as a "SURROBODY™," and the two terms are used interchangeably.

In the context of the polypeptides of the present invention, the term "heterogeneous amino acid sequence," relative to a first amino acid sequence, is used to refer to an amino acid sequence not naturally associated with the first amino acid sequence, at least not in the form it is present in the surrogate light chain constructs herein. Thus, a "heterogenous amino acid sequence" relative to a VpreB is any amino acid sequence not associated with native VpreB in its native environment, including, without limitation, λ5 sequences that are different from those λ5 sequences that, together with VpreB, form the surrogate light chain on developing B cells, such as amino acid sequence variants, e.g. truncated and/or derivatized λ5 sequences. A "heterogeneous amino acid sequence" relative to a VpreB also includes λ5 sequences covalently associated with, e.g. fused to, VpreB, including native sequence λ5, since in their native environment, the VpreB and λ5 sequences are not covalently associated, e.g. fused, to each other. Heterogeneous amino acid sequences also include, without limitation, antibody sequences, including antibody and heavy chain sequences and fragments thereof, such as, for example, antibody light and heavy chain variable region sequences, and antibody light and heavy chain constant region sequences.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the term "target" is a substance that interacts with a polypeptide herein. Targets, as defined herein, specifically include antigens with which the VpreB-containing constructs of the present invention interact. Preferably, interaction takes place by direct binding.

As used herein, the terms "peptide," "polypeptide" and "protein" all refer to a primary sequence of amino acids that are joined by covalent "peptide linkages." In general, a peptide consists of a few amino acids, typically from about 2 to about 50 amino acids, and is shorter than a protein. The term "polypeptide," as defined herein, encompasses peptides and proteins.

The term "amino acid" or "amino acid residue" typically refers to an amino acid having its art recognized definition such as an amino acid selected from the group consisting of alanine (Ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids may be used as desired. Thus, modified and unusual amino acids listed in 37 CFR 1.822 (b)(4) are specifically included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp, Asp, Glu), amides (Asp, Glu), and basic amino acids (Lys, Arg).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at" a specified position, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301 336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "mutagenesis" refers to, unless otherwise specified, any art recognized technique for altering a polynucleotide polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

In the context of the present invention, the term "antibody" (Ab) is used to refer to a native antibody from a classically recombined heavy chain derived from V(D)J gene recombination and a classically recombined light chain also derived from VJ gene recombination, or a fragment thereof.

A "native antibody" is heterotetrameric glycoprotein of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., J. Mol. Biol. 186:651 (1985); Novotny and Haber, Proc. Natl. Acad. Sci. U.S.A. 82:4592 (1985).

The term "variable" with reference to antibody chains is used to refer to portions of the antibody chains which differ extensively in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 30-36 (L1), 46-55 (L2) and 86-96 (L3) in the light chain variable domain and 30-35 (H1), 47-58 (H2) and 93-101 (H3) in the heavy chain variable domain; MacCallum et al., J Mol Biol. 262(5):732-45 (1996).

The term "framework region" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface.

Depending on the amino acid sequence of the constant domain of their heavy chains, antibodies can be assigned to different classes. There are five major classes of antibodies IgA, IgD, IgE, IgG, and IgM, and several of these may be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains. Any reference to an antibody light chain herein includes both κ and λ light chains.

"Antibody fragments" comprise a portion of a full length antibody, generally the antigen binding or a variable domain thereof. Examples of antibody fragments include, but are not limited to, Fab, Fab', F(ab')$_2$, scFv, and (scFv)$_2$ fragments.

As used herein the term "antibody binding region" refers to one or more portions of an immunoglobulin or antibody variable region capable of binding an antigen(s). Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody.

The term "epitope" as used herein, refers to a sequence of at least about 3 to 5, preferably at least about 5 to 10, or at least about 5 to 15 amino acids, and typically not more than about 500, or about 1,000 amino acids, which define a sequence that by itself, or as part of a larger sequence, binds to an antibody generated in response to such sequence. An epitope is not limited to a polypeptide having a sequence identical to the portion of the parent protein from which it is derived. Indeed, viral genomes are in a state of constant change and exhibit relatively high degrees of variability between isolates. Thus the term "epitope" encompasses sequences identical to the native sequence, as well as modifications, such as deletions, substitutions and/or insertions to the native sequence. Generally, such modifications are conservative in nature but non-conservative modifications are also contemplated. The term specifically includes "mimotopes," i.e. sequences that do not identify a continuous linear native sequence or do not necessarily occur in a native protein, but functionally mimic an epitope on a native protein. The term "epitope" specifically includes linear and conformational epitopes.

The term "vector" is used to refer to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors." The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

The term "filamentous phage" refers to a viral particle capable of displaying a heterogenous polypeptide on its surface, and includes, without limitation, fl, fd, Pfl, and M13. The filamentous phage may contain a selectable marker such as tetracycline (e.g., "fd-tet"). Various filamentous phage display systems are well known to those of skill in the art (see, e.g., Zacher et al. Gene 9: 127-140 (1980), Smith et al. Science 228: 1315-1317 (1985); and Parmley and Smith Gene 73: 305-318 (1988)).

The term "panning" is used to refer to the multiple rounds of screening process in identification and isolation of phages carrying compounds, such as antibodies, with high affinity and specificity to a target.

B. Detailed Description

Techniques for performing the methods of the present invention are well known in the art and described in standard laboratory textbooks, including, for example, Ausubel et al., Current Protocols of Molecular Biology, John Wiley and Sons (1997); Molecular Cloning: A Laboratory Manual, Third Edition, J. Sambrook and D. W. Russell, eds., Cold Spring Harbor, N.Y., USA, Cold Spring Harbor Laboratory Press, 2001; O'Brian et al., Analytical Chemistry of *Bacillus Thuringiensis*, Hickle and Fitch, eds., Am. Chem. Soc., 1990; *Bacillus thuringiensis*: biology, ecology and safety, T. R. Glare and M. O'Callaghan, eds., John Wiley, 2000; Antibody Phage Display, Methods and Protocols, Humana Press, 2001; and Antibodies, G. Subramanian, ed., Kluwer Academic, 2004. Mutagenesis can, for example, be performed using site-directed mutagenesis (Kunkel et al., Proc. Natl. Acad. Sci USA 82:488-492 (1985)). PCR amplification methods are described in U.S. Pat. Nos. 4,683,192, 4,683,202, 4,800,159, and 4,965,188, and in several textbooks including "PCR Technology: Principles and Applications for DNA Amplification", H. Erlich, ed., Stockton Press, New York (1989); and PCR Protocols: A Guide to Methods and Applications, Innis et al., eds., Academic Press, San Diego, Calif. (1990).

The present invention concerns constructs and libraries comprising antibody surrogate light chain sequences.

Surrogate Light Chain Sequences

As discussed above, pre-B cells have been identified in the bone marrow as lymphocytes that produce µ heavy chains but instead of the fully developed light chains express a set of B lineage-specific genes called VpreB(1-3) and λ5, respectively. The VpreB and λ5 polypeptides together form a non-covalently associated, Ig light chain-like structure, which is called the surrogate light chain. The surrogate light chain, although not an antibody chain, naturally associates with all antibody heavy chains, and surrogate light chain-antibody heavy chain complexes have been shown to bind self-antigens.

In one aspect, the present invention provides polypeptides comprising VpreB and/or λ5 sequences and having the ability to bind a target. The target can be any peptide or polypeptide that is a binding partner for the VpreB and/or λ5 sequence-containing polypeptides of the present invention. Targets specifically include all types of targets generally referred to as "antigens" in the context of antibody binding.

Thus, the polypeptides of the present invention include, without limitation, conjugates of VpreB sequences to heterogeneous amino acid sequences, provided that they retain the ability to bind a desired target. The binding of the VpreB sequence to the heterogeneous amino acid sequence can be either covalent or non-covalent, and may occur directly, or through a linker, including peptide linkers.

Specific examples of the polypeptide constructs herein include polypeptides in which a VpreB sequence, such as a VpreB1, VpreB2, or VpreB3 sequence, including fragments and variants of the native sequences, is conjugated to a λ5 sequence, including fragments and variants of the native sequence. Representative fusions of this type are illustrated in FIGS. 2 and 11 and described in the Examples.

In a direct fusion, typically the C-terminus of a VpreB sequence (e.g. a VpreB1, VpreB2 or VpreB3 sequence) is fused to the N-terminus of a λ5 sequence. While it is possible to fuse the entire length of a native VpreB sequence to a full-length λ5 sequence (see, e.g. the first diagram in FIG. 3), typically the fusion takes place at or around a CDR3 analogous site in each of the two polypeptides. Such CDR3 analogous sites for VpreB1 and λ5 are illustrated in FIG. 1, and a representative fusion construct is illustrated in FIG. 2. In this embodiment, the fusion may take place within, or at a location within about 10 amino acid residues at either side of the CDR3 analogous region. In a preferred embodiment, the fusion takes place between about amino acid residues 116-126 of the native human VpreB1 sequence (SEQ ID NO: 1) and between about amino acid residues 82 and 93 of the native human λ5 sequence (SEQ ID NO: 5).

It is also possible to fuse the VpreB sequence to the CDR3 region of an antibody λ light chain, as shown in FIG. 2. Further constructs, in which only one of VpreB and λ5 is truncated are shown in FIG. 3. Similar constructs can be prepared using antibody κ light chain sequences.

Figure 11:
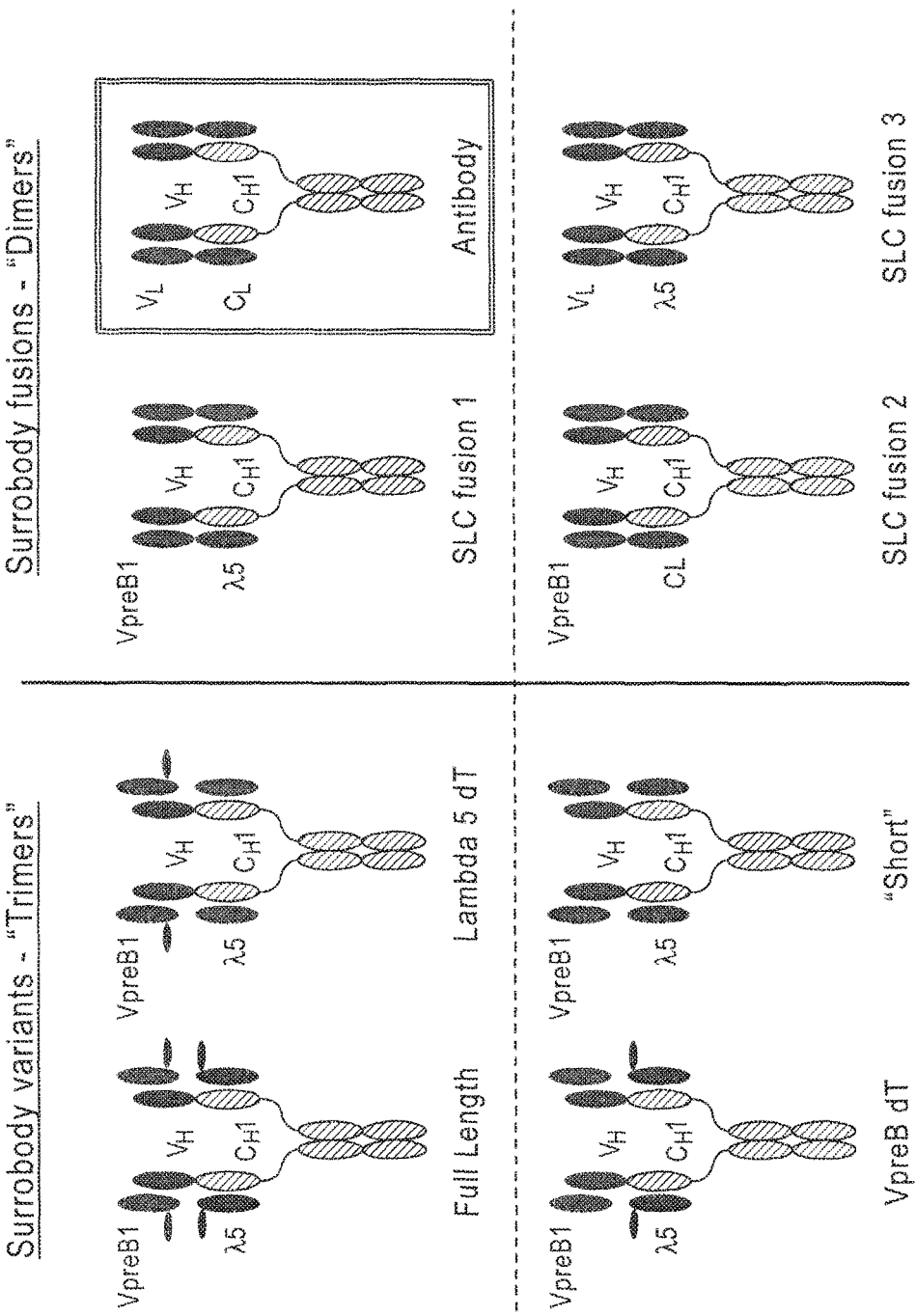
FIG. 11 illustrates various trimeric and dimeric surrogate light chain constructs of the invention.
Figure 12:
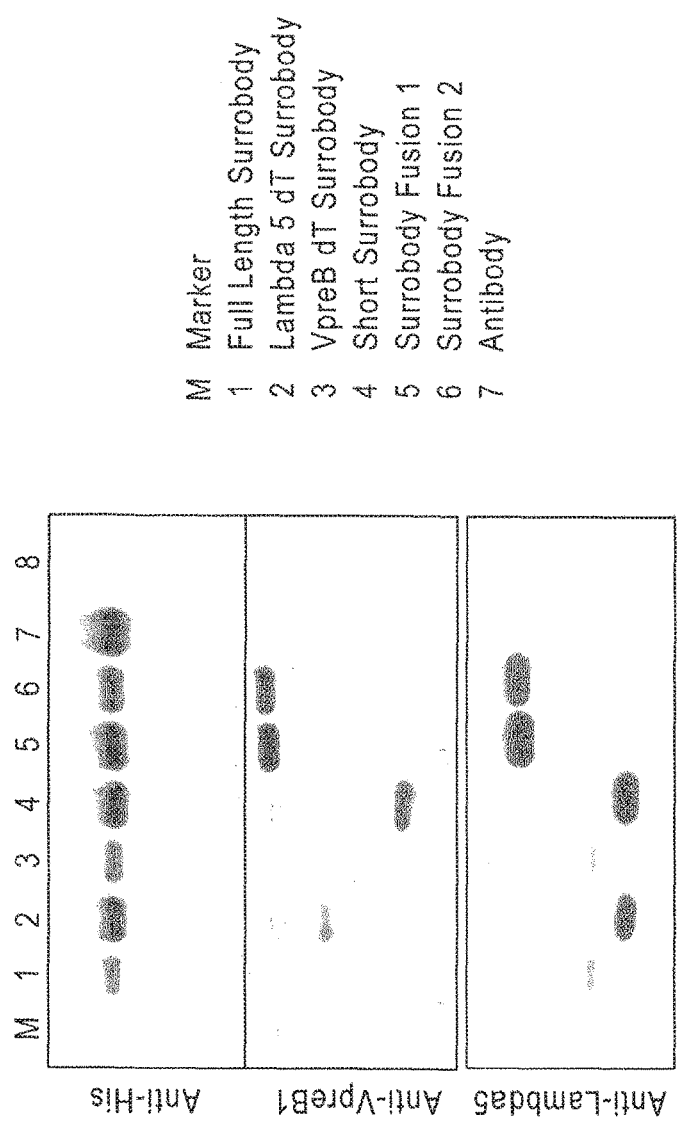
FIG. 12: Detection of surrogate light chains and conjugated heavy chains. Lane 1: Full Length; Lane 2: Lambda 5 dT; Lane 3: VpreB dt; Lane 4: Short; Lane 5: SCL fusion 1; Lane 6: SLC fusion 2; Lane 7: Antibody.

Further direct fusion structures are illustrated on the right side of FIG. 11 The structure designated "SLC fusion 1" is a tetramer, composed of two dimers, in which the fusion of a truncated V-preB1 sequence (lacking the characteristic "tail" at the C-terminus of native VpreB1) to a similarly truncated λ5 sequence is non-covalently associated with an antibody heavy chain. The structure designated "SLC fusion 2" is a tetramer, composed of two dimers, in which the fusion of a truncated VpreB1 sequence (lacking the characteristic "tail" at the C-terminus of native VpreB1) to an antibody light chain constant region is non-covalently associated with an antibody heavy chain. The structure designated "SLC fusion 3" is a tetramer, composed of two dimers, in which the fusion of an antibody light chain variable region to a truncated λ5 sequence (lacking the characteristic "tail" at the N-terminus of native λ5) is non-covalently associated with an antibody heavy chain.

As noted above, in addition to direct fusions, the polypeptide constructs of the present invention include non-covalent associations of a VpreB sequence (including fragments and variants of a native sequence) with a heterogeneous sequence, such as a λ5 sequence (including fragments and variants of the native sequence), and/or an antibody sequence. Thus, for example, a full-length VpreB sequence may be non-covalently associated with a truncated λ5 sequence. Alternatively, a truncated VpreB sequence may be non-covalently associated with a full-length λ5 sequence.

Surrogate light chain constructs comprising non-covalently associated VpreB1 and λ5 sequences, in non-covalent association with an antibody heavy chain, are shown on the left side of FIG. 11. As the various illustrations show, the structures may include, for example, full-length VpreB1 and λ5 sequences, a full-length VpreB1 sequence associated with a truncated λ5 sequence ("Lambda 5dT"), a truncated V-reB1 sequence associated with a full-length λ5 sequence (VpreB dT") and a truncated VpreB1 sequence associated with a truncated λ5 sequence ("Short").

Although FIG. 11 illustrates certain specific constructs, one of ordinary skill will appreciate that a variety of other constructs can be made and used in a similar fashion. For example, the structures can be asymmetrical, comprising different surrogate light chain sequences in each arm, and/or having trimeric or pentameric structures, as opposed to the structures illustrated in FIG. 11. It is also possible to include different functionalities in various portions of the surrogate light chain constructs of the present invention, thereby producing multi-specific and/or multivalent constructs.

If desired, the constructs of the present invention can be engineered, for example, by incorporating or appending known sequences or sequence motifs from the CDR1, CDR2 and/or CDR3 regions of antibodies, including known therapeutic antibodies into the CDR1, CDR2 and/or CDR3 analogous regions of the surrogate light chain sequences. This allows the creation of molecules that are not antibodies, but will exhibit binding specificities and affinities very similar to those of a known therapeutic antibody.

All surrogate light chain constructs herein may be associated with antibody sequences. For example, as shown in FIG. 5, a VpreB-λ5 fusion can be linked to an antibody heavy chain variable region sequence by a peptide linker. In another embodiment, a VpreB-λ5 fusion is non-covalently associated with an antibody heavy chain, or a fragment thereof including a variable region sequence to form a dimeric complex. In yet another embodiment, the VpreB and λ5 sequences are non-covalently associated with each other and an antibody heavy chain, or a fragment thereof including a variable region sequence, thereby forming a trimeric complex. Exemplary constructs comprising an antibody heavy chain are illustrated in FIG. 11.

While the constructs of the present invention are illustrated by reference to certain embodiments, one of ordinary skill will understand that numerous further embodiments obtained by various permutations of surrogate light chain and antibody sequences are possible, and are within the scope of the present invention. The present invention includes all constructs that comprise surrogate light chain sequences and have the ability to bind a desired target. In certain embodiment, the constructs also have the ability to associate with antibody heavy chain variable region sequences.

The constructs of the present invention may be used to build libraries of surrogate light chain sequences, which can be used for various purposes, similarly to antibody libraries, including selection of constructs with the desired binding specificities and affinities.

When the VpreB and λ5 surrogate light chain sequences are non-covalently associated with each other, the free ends of one or both components (i.e. the C-terminal end of the VpreB sequence and/or the N-terminal end of the λ5 sequence) are available for incorporating an additional diversity into the library of such sequences. For instance, a random peptide library can be appended or substituted to one of these free ends and panned for specific binding to a particular target. By combining the surrogate light chain identified to have the desired binding specificity with a heavy chain or heavy chain fragment from an antibody to the same target, a molecule can be created that has the ability to bind to the cognate target on two distinct places. This tandem binding, or "chelating" effect, strongly reinforces the binding to a single target, similarly to the avidity effects seen in dimeric immunoglobulins. It is also possible to use components binding to different targets. Thus, for example, the surrogate light chain component with the desired binding specificity can be combined with an antibody heavy chain or heavy fragment binding to a different target. For instance, the surrogate light chain component may bind a tumor antigen while the antibody heavy chain or heavy chain fragment may bind to effector cells. This way, a single entity with targeting and anti-tumor activity can be created. In a particular embodiment, the appendage or the polypeptide that connects the VpreB and λ5 sequences can be an antibody or antibody fragments, such as a Fab or a scFv fragment. The incorporation of an antibody sequence will not only create a "chelating" effect but can also generate bispecificity in a single molecule, without the need of a second independent arm, such as that found in bispecific antibodies. The two specificities may be to different parts of the same target, to disparate targets, or to a target antibody complex. Similarly, multi-specific constructs can be made with any type of molecule, other than antibodies or antibody fragments, including peptides, proteins, enzymes, and the like. For example, the surrogate light chain component with the desired specificity can be combined with any therapeutic peptide or protein.

Preparation of Surrogate Light Chain Constructs

The surrogate light chain constructs of the present invention can be prepared by methods known in the art, including well known techniques of recombinant DNA technology.

Nucleic acid encoding surrogate light chain, e.g. VpreB and λ5 polypeptides, can be isolated from natural sources, e.g. developing B cells and/or obtained by synthetic or semi-synthetic methods. Once this DNA has been identified and isolated or otherwise produced, it can be ligated into a replicable vector for further cloning or for expression.

Cloning and expression vectors that can be used expressing the coding sequences of the polypeptides herein are well known in the art and are commercially available. The vector components generally include, but are not limited to, one or more of the following: a signal sequence, an origin of replication, one or more marker genes, an enhancer element, a promoter, and, a transcription termination sequence. Suitable host cells for cloning or expressing the DNA encoding the surrogate light chain constructs in the vectors herein are prokaryote, yeast, or higher eukaryote (mammalian) cells, mammalian cells are being preferred.

Examples of suitable mammalian host cell lines include, without limitation, monkey kidney CV1 line transformed by SV40 (COS-7, ATCC CRL 1651); human embryonic kidney line 293 (293 cells) subcloned for growth in suspension culture, Graham et al, J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W 138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a humn hepatoma line (Hep G2).

For use in mammalian cells, the control functions on the expression vectors are often provided by viral material. Thus, commonly used promoters can be derived from the genomes of polyoma, Adenovirus2, retroviruses, cytomegalovirus, and Simian Virus 40 (SV40). Other promoters, such as the β-actin protomer, originate from heterologous sources. Examples of suitable promoters include, without limitation, the early and late promoters of SV40 virus (Fiers et al., Nature, 273: 113 (1978)), the immediate early promoter of the human cytomegalovirus (Greenaway et al., Gene, 18: 355-360 (1982)), and promoter and/or control sequences normally associated with the desired gene sequence, provided such control sequences are compatible with the host cell system.

Transcription of a DNA encoding a desired heterologous polypeptide by higher eukaryotes is increased by inserting an enhancer sequence into the vector. The enhancer is a cis-acting element of DNA, usually about from 10 to 300 bp, that acts on a promoter to enhance its transcription-initiation activity. Enhancers are relatively orientation and position independent, but preferably are located upstream of the promoter sequence present in the expression vector. The enhancer might originate from the same source as the promoter, such as, for example, from a eukaryotic cell virus, e.g. the SV40 enhancer on the late side of the replication origin (bp 100-270), the cytomegalovirus early promoter enhancer, the polyoma enhancer on the late side of the replication origin, and adenovirus enhancers.

Expression vectors used in mammalian host cells also contain polyadenylation sites, such as those derived from viruses such as, e.g., the SV40 (early and late) or HBV.

An origin of replication may be provided either by construction of the vector to include an exogenous origin, such as may be derived from SV40 or other viral (e.g., Polyoma, Adeno, VSV, BPV) source, or may be provided by the host cell.

The expression vectors usually contain a selectable marker that encodes a protein necessary for the survival or growth of a host cell transformed with the vector. Examples of suitable selectable markers for mammalian cells include dihydrofolate reductase thymidine kinase (TK), and neomycin.

Suitable mammalian expression vectors are well known in the art and commercially available. Thus, for example, the surrogate light chain constructs of the present invention can be produced in mammalian host cells using a pCI expression vector (Promega), carrying the human cytomegalovirus (CMV) immediate-early enhancer/promoter region to promote constitutive expression of a DNA insert. The vector can contain a neomycin phosphotransferase gene as a selectable marker.

The surrogate light chain constructs of the present invention can also be produced in bacterial host cells. Control elements for use in bacterial systems include promoters, optionally containing operator sequences, and ribosome binding sites. Suitable promoters include, without limitation, galactose (gal), lactose (lac), maltose, tryptophan (trp), β-lactamase promoters, bacteriophage λ and T7 promoters. In addition, synthetic promoters can be used, such as the tac promoter. Promoters for use in bacterial systems also generally contain a Shine-Dalgarno (SD) sequence operably linked to the DNA encoding the Fab molecule. The origin of replication from the plasmid pBR322 is suitable for most Gram-negative bacteria.

The coding sequences of the individual chains within a multi-chain construct comprising antibody surrogate light chain sequences can be present in the same expression vector, under control of separate regulatory sequences, or in separate expression vectors, used to cotransfect a desired host cells, including eukaryotic and prokaryotic hosts. Thus, multiple genes can be coexpressed using the Duet™ vectors commercially available from Novagen.

The transformed host cells may be cultured in a variety of media. Commercially available media for culturing mammalian host cells include Ham's F10 (Sigma), Minimal Essential Medium ((MEM), (Sigma), RPM1-1640 (Sigma), and Dulbecco's Modified Eagle's Medium ((DMEM), Sigma). In addition, any of the media described in Ham et al., Meth. Enz. 58:44 (1979) and Barnes et al., Anal. Biochem. 102:255 (1980) may be used as culture media for the host cells. The culture conditions, such as temperature, pH, and the like, are those previously used with the host cell selected for expression, and are included in the manufacturer's instructions or will otherwise be apparent to the ordinarily skilled artisan.

Further suitable media for culturing mammalian, bacterial (e.g. *E. coli*) or other host cells are also described in standard textbooks, such as, for example, Sambrook et al., supra, or Ausubel et al., supra.

Purification can be performed by methods known in the art. In a preferred embodiment, the surrogate antibody molecules are purified in a 6.times.His-tagged form, using the Ni-NTA purification system (Invitrogen).

Libraries Comprise Surrogate Light Chain Sequences

The present invention further concerns various libraries of surrogate light chain sequences and constructs comprising such sequences. Thus, such libraries may comprise, consist essentially of, or consist of, displays of surrogate light chain sequences, such as the VpreB- and/or λ5-containing constructs of the present invention, including, without limitation, those specifically described above, illustrated in the figures and/or described in the Examples.

The libraries of the present invention are preferably in the form of a display. Systems for displaying heterologous proteins, including antibodies and other polypeptides, are well known in the art. Antibody fragments have been displayed on the surface of filamentous phage that encode the antibody genes (Hoogenboom and Winter J. Mol. Biol., 222:381 388 (1992); McCafferty et al., Nature 348(6301): 552 554 (1990); Griffiths et al. EMBO J., 13(14):3245-3260 (1994)). For a review of techniques for selecting and screening antibody libraries see, e.g., Hoogenboom, Nature Biotechnol. 23(9):1105-1116 (2005). In addition, there are systems known in the art for display of heterologous proteins and fragments thereof on the surface of *Escherichia coli* (Agterberg et al., Gene 88:37-45 (1990); Charbit et al., Gene 70:181-189 (1988); Francisco et al., Proc. Natl. Acad. Sci. USA 89:2713-2717 (1992)), and yeast, such as *Saccharomyces cerevisiae* (Boder and Wittrup, Nat. Biotechnol. 15:553-557 (1997); Kieke et al., Protein Eng. 10:1303-1310 (1997)). Other known display techniques include ribosome or mRNA display (Mattheakis et al., Proc. Natl. Acad. Sci. USA 91:9022-9026 (1994); Hanes and Pluckthun, Proc. Natl. Acad. Sci. USA 94:4937-4942 (1997)), DNA display (Yonezawa et al., Nucl. Acid Res. 31(19):e118 (2003)); microbial cell display, such as bacterial display (Georgiou et al., Nature Biotech. 15:29-34 (1997)), display on mammalian cells, spore display (Isticato et al., J. Bacterial. 183: 6294-6301 (2001); Cheng et al., Appl. Environ. Microbiol. 71:3337-3341 (2005) and co-pending provisional application Ser. No. 60/865,574, filed Nov. 13, 2006), viral display, such as retroviral display (Urban et al., Nucleic Acids Res. 33:e35 (2005), display based on protein-DNA linkage (Odegrip et al., Proc. Acad. Natl. Sci. USA 101:2806-2810 (2004); Reiersen et al., Nucleic Acids Res. 33:e10 (2005)), and microbead display (Sepp et al., FEBS Lett. 532:455-458 (2002)).

For the purpose of the present invention, the surrogate light chain-containing libraries may be advantageously displayed using any display technique, including phage display and spore display.

In phage display, the heterologous protein, such as a surrogate light chain polypeptide, is linked to a coat protein of a phage particle, while the DNA sequence from which it was expressed is packaged within the phage coat. Details of the phage display methods can be found, for example, McCafferty et al., Nature 348, 552-553 (1990)), describing the production of human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell.

Phage display can be performed in a variety of formats; for their review see, e.g. Johnson, Kevin S. and Chiswell, David J., Current Opinion in Structural Biology 3, 564-571 (1993). Several sources of heavy chain V-gene segments can be discovered through phage display. Clarkson et al., Nature 352, 624-628 (1991) isolated a diverse array of anti-oxazolone heavy chains and light chains from a small random combinatorial library of V genes derived from the spleens of immunized mice. A repertoire of heavy and light chain V genes from unimmunized human donors can be constructed and recovered specific to a diverse array of antigens (including self-antigens) essentially following the techniques described by Marks et al., J. Mol. Biol. 222, 581-597 (1991), or Griffith et al., EMBO J. 12, 725-734 (1993). These, and other techniques known in the art, can be adapted to the display of any polypeptide, including polypeptides and other constructs comprising surrogate light chain sequences. Thus, for example, the surrogate light chain can be supplemented with a collection of heavy chains from either a naturally diverse source, such as lymphocytes, or a synthetically generated collection created entirely through techniques of molecular biology. These collections can be cloned, expressed and selected, by methods known in the art. The selected resulting surrogate light chain construct (or SURROBODY™) can be used directly, expressed as multimeric a molecule, or further optimized through heavy chain optimization, or surrogate light chain optimization, for example, using random or nonrandom site specific or regional mutagenesis.

Spore display systems are based on attaching the sequences to be displayed to a coat protein, such as a *Bacillus subtilis* spore coat protein. The spore protoplast (core) is surrounded by the cell wall, the cortex, and the spore coat. Depending on the species, an exosporium may also be present. The core wall is composed of the same type of peptidoglycan as the vegetative cell wall. Spore display, including surface display system using a component of the *Bacillus subtilis* spore coat (CorB) and *Bacillus thuringiensis* (Bt) spore display, is described in Isticato et al., J. Bacteriol. 183:6294-6301 (2001); Cheng et al., Appl. Environ. Microbiol. 71:3337-3341 (2005), the entire disclosures of which is hereby expressly incorporated by reference. Various spore display techniques are also disclosed in U.S. Patent Application Publication Nos. 20020150594; 20030165538; 20040180348; 20040171065; and 20040254364, the entire disclosures are hereby expressly incorporated by reference herein.

An advantage of spore display systems is the homogenous particle surface and particle size of non-eukaryotic nature, which is expected to provide an ideal non-reactive background. In addition, the particle size of spores is sufficient to enable selection by flow cytometry that permits selectable clonal isolation, based upon interactions.

Leveraging on the stability of spores, it is possible to perform various post-sporulation chemical, enzymatic and/or environmental treatments and modification. Thus, it is possible to stabilize structural helical structures with chemical treatment using trifluoroethanol (TFE), when such structures are displayed. In addition, oxidative stress treatments, such as treatments with Reactive Oxygen Species (e.g. peroxide) or reactive Nitrogen Species (e.g. nitrous acid) are possible. It is also possible to expose defined or crude populations of spore-displayed polypeptides to enzymatic treatments, such as proteolytic exposure, other enzymatic processes, phosphorylation, etc. Other possible treatments include, without limitation, nitrosylation by peroxynitrite treatment, proteolysis by recombinant, purified, or serum protease treatment, irradiation, coincubation with known chaperones, such as heat shock proteins (both bacterial and mammalian), treatment with folding proteins, such as protein disulfide isomerase, prolyl isomerase, etc., lyophilization, and preservative-like treatments, such as treatment with thimerosol. These treatments can be performed by methods well known in the art.

Similar techniques can be used in all spore display systems, including displays where the attachment is to a spore coat protein, including, for example, the spore display systems disclosed in Uses of Surrogate Light Chain Sequences, Constructs, and Libraries Containing the Same The libraries of the present invention can be used to identify surrogate light chain sequences and surrogate light chain constructs, such as fusions comprising surrogate light chain sequences, with desired properties. For example, in vitro or in vivo screening of the libraries herein can yield polypeptides comprising surrogate light chain sequences binding to desired targets with high binding specificity and affinity. Thus, the libraries herein can be used to identify molecules for therapeutic and diagnostic purposes, such as polypeptides comprising surrogate light chain sequences that bind to tumor markers or other molecular targets of therapeutic intervention. In addition, by the techniques described above, highly diverse libraries of surrogate light chain polypeptides can be engineered, including libraries comprising a collection of polypeptides binding to the same target, libraries of polypeptides binding to different targets, libraries of polypeptides with multiple specificities, and the like.

As a result of their ability to bind to any desired target, the antibody surrogate light chain constructs of the present invention can be used in analytical and diagnostic assays, to detect the presence of a desired target molecule, such as a tumor antigen or any polypeptide associated with a disease state or condition. In addition, the surrogate light chain constructs of the present invention can be used as therapeutic agents, such as, for example, in cancer therapy, to target tumor antigens that have been determined to associate with the development and/or spread of cancer.

Further details of the invention are provided in the following non-limiting Examples.

EXAMPLE 1

VpreB as a Binding Domain Protein and Fusions Containing It

To make a VpreB binding domain a single protein shown in FIG. 5 is created recombinantly. The SLC binding domain protein construct is comprised of the amino acids 20 to 121 from VpreB1 and the amino acids 87 to 105 from λ5. If desired, to create novel and specific binding capabilities, the molecule is reengineered according to structural or sequence evidence. Additionally, or alternatively, a collection of variants is created either randomly, for example by error-prone PCR, or directly by single or multi-site specific mutagenesis with a collection of amino acids. The resulting clones or collections are then cloned in frame with pIII for use in phage or phagemid display. This phagemid construct is transformed into TG1 cells. Next a single colony is propagated in Luria Broth (LB) supplemented with 50 μg/ml Ampicillin and 2% glucose until it reached OD600~0.3, and infected with MK307 helper phage at 37° C. for 30 minutes without shaking. The cells are then pelleted and then resuspended in LB containing 50 μg/ml ampicillin and 75 μg/ml kanamycin and allowed to grow overnight with vigorous aeration at 30° C. The next day the supernatant containing phagemid expressed SLC-HC fusion protein is used in Phage ELISA to determine targeted binding. Briefly the ELISA entails coating and blocking of an ELISA plate with human TNF-α, followed by incubation of the SLC-HC phage for 2 hours at 4° C., washing with PBS-polyethylene glycol sorbitan monolaurate-20 (PBS-TWEEN™-20) (0.05%) and direct detection with anti-m13-HRP antibody. Alternatively binding is assessed by directly amplifying or eluting the bound phage and determining phage titers using XL-1 Blue cells. This example describes a SLC binding domain fusion as a single clone, but this SLC can be recombinantly recombined with other heterologous sequences that recognize a common target and screened as a library. Furthermore, this SLC binding protein can be combined with a previously selected collection of heavy chains and screened directly on the same target of interest or a second target of interest to create a bispecific molecule. Alternatively this reinforced binding or bispecific binding can be discovered by screening in conjunction with unselected collections of heavy chains. In addition, while this example refers to antibody heavy chains, it should be understood that a complete heavy chain is not needed. Single-chain fusions comprising heavy chain variable region sequences, in the absence of a heavy chain constant region, or a complete heavy chain constant region, can be made in an analogous manner and are within the scope of this example.

EXAMPLE 2

VpreB Fusions as a Variable Heavy Chain (VH) Partner

A functional VpreB-λ5 fusion protein shown in the second diagram of FIG. 5 (designated "VpreB protein fusion—dimeric complex") is recombinantly created. The VpreB-λ5 fusion protein is comprised of an m13 gene III signal sequence, the amino acids 20 to 115 from VpreB1, and the amino acids 83 to 209 from λ5. This construct is coexpressed with a variable heavy chain-CH1 fusion in frame with pIII for use in phage phagemid display. As a VH coding sequence the VH coding sequence from the anti-TNF-α antibody, D2E7, is used, and CH1 is the CH1 region of human IgG1. This phagemid construct is transformed into TG1 cells. Next, a single colony is propagated in Luria Broth (LB) supplemented with 50 μg/ml Ampicillin and 2% glucose until it reached OD600~0.3, and infected with MK307 helper phage at 37 degrees for 30 minutes, without shaking. The cells are then pelleted and then resuspended in LB Briefly the ELISA entails coating and blocking of an ELISA plate with human TNF-α, followed by incubation of the SLC-HC phage for 2 hours at 4 degrees, washing with PBS-TWEEN™-20 (0.05%) and direct detection with anti-m13-HRP antibody. Alternatively binding can be assessed by directly amplifying or eluting the bound phage and determining phage titers using XL-1 Blue cells. This example describes a SLC partnered with a heavy chain variable-CH1 fusion as a single clone, but this SLC can be combined with a focused collection of heavy chain variable regions that recognize a common target and screened as a library. Furthermore, this SLC fusion can be combined with an unselected collection of heavy chains and screened directly on a target of interest.

EXAMPLE 3

VpreB and Lambda5 as an Associated Variable Heavy Chain (VH) Partner

The VpreB-λ5 coexpressed protein shown in the third diagram of FIG. 5 (designated "VpreB and lambda 5-trimeric complex") is made of an m13 gene III signal sequence and the corresponding amino acids of the predicted mature, processed VpreB1 (amino acids 20 to 146) and lambda 5 (amino acids 31 to 209). These are coexpressed with a variable heavy chain-CH1 fusion in frame with pIII for use in phage or phagemid display. As a VH coding sequence the VH coding sequence from the anti-TNF-αantibody, D2E7, is used, and CH1 is the CH1 region from human IgG1. This phagemid construct is transformed into TG1 cells. Next a single colony is propagated in Luria Broth (LB) supplemented with 50 μg/ml Ampicillin and 2% glucose until it reached OD600~0.3, and is then infected with MK307 helper phage at 37 degrees for 30 minutes, without shaking. The cells are then pelleted and then resuspended in LB containing 50 μg/ml ampicillin and 75 μ/ml kanamycin and allowed to grow overnight with vigorous aeration at 30 degrees. The next day the supernatant containing phagemid expressed SLC HC trimeric protein complexes is used in Phage ELISA to determine targeted binding. Briefly the ELISA entails coating and blocking of an ELISA plate with human TNF-α, followed by incubation of the SLC-HC phage for 2 hours at 4 degrees, washing with PBS-TWEEN™-20 (0.05%) and direct detection with anti-m13-HRP antibody. Alternatively binding can be assessed by directly amplifying or eluting the bound phage and determining phage titers using XL-1Blue cells. This example describes a SLC partnered with a heavy chain variable-CH1 fusion as a single clone, but this SLC can be combined with a focused collection of heavy chain variable regions that recognize a common target and screened as a library. Furthermore, this SLC fusion can be combined with an unselected collection of heavy chains and screened directly on a target of interest.

EXAMPLE 4

Engineering Diversity into VpreB1 CDR3 Analogous Regions

As the CDR analogous regions of the surrogate light chain (SLC) will have similar functions to the CDR's of an antibody light chain, it is important to determine the fusion points between the VpreB and λ5. According to one approach the most suitable fusion point for a particular purpose is determined starting with the CDR3 analogous site containing all VpreB amino acids and incrementally substituting amino acids position by position from λ5 encoded in clonable oligonucleotides. This incremental substitution continues until the CDR analogous site is entirely composed of a λ5 source sequence. At some point during this process, it might be desirable to add a complementary heavy chain and allow/facilitate its antigen binding and recognition. To further enhance or enable this complementation random diversity can be used in any of the CDR analogous sites, as well as diversity based upon matched CDR length analysis. Alternatively, or in addition, antibody Vλ5 sequences can be used to add diversity, as their CDR lengths match well with VpreB CDR analogous site lengths.

EXAMPLE 5

Adding Functionalities to SLC Components

As the SLC is comprised of two independent polypeptides this creates natural opportunities to append or embed secondary functionalities. In the present Example, in the first instance an anti-VEGF scFv is inserted to create a fusion protein linking VpreB and λ5 (FIG. 9A). This resulting engineered SLC-constrained scFv is paired with the heavy chain of an anti-TNF-αantibody. The resulting construct is coexpressed with the heavy chain cloned in frame with pIII for use in phage or phagemid display. This phagemid construct is transformed into TG1 cells and a single colony is propagated in Luria Broth (LB) supplemented with 50 μg/ml Ampicillin and 2% glucose until it reached OD600~03, and infected with MK307 helper phage at 37° C. for 30 minutes without shaking. The cells are then be pelleted and then resuspended in LB containing 50 μg/ml ampicillin and 75 μg/ml kanamycin and allowed to grow overnight with vigorous aeration at 30° C. The next day the supernatant containing phagemid expressed SLC-HC fusion protein is used in Phage ELISA to determine targeted binding. Briefly the ELISA entails coating and blocking of an ELISA plate with human TNF-α or human VEGF, followed by incubation of the SLC-HC phage for 2 hours at 4° C., washing with PBS-TWEEN™-20 (0.05%) and direct detection with anti-m13-HRP antibody.

Next a fusion of the anti-VEGF scFv to the C-terminus of VpreB is created, and the resulting tripartite protein complex construct assessed similarly to the phagemid ELISA described above.

Alternatively the an anti-ovalbumin scFv is fused to the amino terminus of λ5 and the tripartite protein complex tested for binding to both TNF-α and ovalbumin.

Finally, these two fusion constructs (VpreB-antiVEGF scFv and the λ5-anti-ovalbumin) are combined with the heavy chain of the anti-TNF-αantibody to create a trispecific molecule, which is then confirmed in phagemid ELISA as described above.

In the description scFv against disparate targets are incorporated, however one can combine functional binders to the same target to create tandem "super-binders." These tandem binders can either provide reinforced binding or even in some instances cross-linking function. Fab cross-linking will be beneficial in instances where whole antibodies provide undesirable and prolonged cross-linking. For instance, it may be undesirable for whole immunoglobulin insulin receptor antibodies that act as insulin substitutes to require 3-4 weeks for serum clearance. As insulin usually has a half-life of minutes, a Fab would be more in tune with this scale of half-life and the tandem functionality could appropriately address this application.

The above descriptions describe only antibodies as secondary functional groups, but one can also similarly incorporate relevant peptides (e.g., erythropoietin (EPO) mimetics), receptors (e.g., TNF-RI), binding proteins (e.g., IL-Ira), and any therapeutic protein, such as interferons, to the appended and constrained constructs to create molecules of similar functions.

Also one might utilize the two sites to incorporate heterodimeric proteins, such as heavy and light chains to create a secondary Fab-like molecule.

Finally, we have described only singular instances, but the incorporation of combinatorially diverse phage antibody libraries and peptide diversity libraries is also included herein, to screen with SLC candidate antibodies against their directed and desired targets.

EXAMPLE 6

Expression of Surrogate Light Chain Constructs (SURROBODY™) in Mammalian Cells Coding sequences of the surrogate light chain components of the structures designated in FIG. 11 as "trimers" (also referred to as variant surrogate light chain constructs "SURROBODY™ variants") were cotransfected with a full-length IgG1 antibody heavy chain into CHO-K1 cells (ATCC CCL-61) to transiently produce surrogate light chain constructs for biochemical analysis. Specifically, full length human VpreB1 and λ5 were cloned into the mammalian expression vector pCI (Promega, Madison Wis.). These constructs contained their native predicted secretion signals. In the case of VpreB1 the predicted signal peptide is amino acids 1-20 of SEQ ID NO: 1, for λ5 the predicted signal sequence is amino acids 1-30 of SEQ ID NO: 5. For both of these proteins portions of their predicted nonstructural tails were deleted. For VpreB1 this included the C-terminal amino acids 122-146 of SEQ ID NO: 1 and for lambda 5 this included the N-terminal amino acids 30-86 of SEQ ID NO: 5.

The sequence of the truncated λ5 sequence in the "trimer" designated in FIG. 11 as "Lambda 5 dT" is shown as SEQ ID NO: 7. The sequence of the truncated VpreB1 sequence in the "trimer" designated in FIG. 11 as "VpreB dT" is shown as SEQ ID NO: 8.

Each of the four combinatorial surrogate light chain possibilities were cotransfected with a known human anti-influenza heavy chain, containing a C-terminal hexahistidine (His6) tag (SEQ ID NO: 9), and expressed according to manufacturer's suggestions (Invitrogen, Carlsbad Calif.) in low serum media. After 3 days the supernatants were collected, filtered, and purified by nickel chelate chromatography (Qiagen, Germany). The purified proteins were then examined by western blot analysis with either anti-peptide rabbit serum (VpreB and λ5) or anti-histidine antibodies (Scrotec, Raleigh N.C.). Detection of proteins was visualized following anti-rabbit HRP (VpreB and λ5) or anti-mouse HRP (heavy chain) and colorimetric development with TMB substrate. (FIG. 12, lanes 1-4)

Additionally, surrogate light chain fusions (see FIG. 11) were created by engineering a chimeric protein composed of the VpreB1 gene and either the λ5 gene or the light chain constant lambda domain. Specifically a recombinantly fused protein was produced that contained amino acids 1-87 from VpreB (SEQ ID NO: 1) to λ5 protein amino acids 121-209 (SEQ ID NO: 5) (SEQ ID NO: 10). Additionally, a second fusion was made that contained amino acids 1-87 from VpreB (SEQ ID NO: 1) to the C-terminal 121 amino acid of the antibody λ light chain constant (SEQ ID NO: 11). Each surrogate light chain fusion was transiently expressed, harvested, purified, and examined by western blot analysis, essentially as described above. Notably, as both fusions contained the epitope to the anti-VpreB1 anti-peptide serum, it was used for western blot analysis. (FIG. 12, lanes 5-6).

EXAMPLE 7

Expression of Surrogate Light Chain Constructs (SURRORODY™) in *E. coli*

As recombinant proteins are often beneficially expressed in bacteria the ability of producing soluble surrogate light chain constructs in prokaryotic systems was tested. To address this, the surrogate light chain fusions designated as "dimers" in FIG. 11 were clones into *E. coli* expression/secretion systems. A plac repressible expression system was used, where the mature mammalian proteins were expressed and secreted into the periplasm by recombinant fusion to prokaryotic leader sequences. Specifically, the surrogate light chain fusions were directed to the periplasm by fusing the coding sequence of the mature protein to the C-terminus of the m13 gIII leader coding sequence (SEQ ID NOs: 12 and 13). The heavy chain was expressed by fusing the IgG1 heavy chain variable region and heavy chain constant region domain of an anti-influenza antibody to the C-terminus of the pelB leader sequence (SEQ ID NO: 14). The plasmids expressing both proteins were transformed into HB2151 *E. coli* cells (Stratagene) and expressed overnight in LB media containing 100 mcg/ml ampicillin, and 200 micromolar IPTG at 30 degrees. The cells were harvested and periplasmic lysates were prepared, following methods known in the art. The periplasmic lysates were tested directly by western blot analysis or purified as described above (FIG. 13, panel A).

As the surrogate light chain is traditionally a component of the membrane bound preB cell receptor, it is normally found paired with an IgM class heavy chain. For our utilitarian purposes we wished to compare the ability to pair a surrogate light chain fusion with an IgM versus a IgG based constant heavy domain 1 region. To examine this we substituted a μ constant heavy domain 1 (SEQ ID NO: 15) for the gamma constant heavy domain region of the anti-influenza antibody described above. We found, trom western blot analysis of the periplasmic lysates that the IgG (γ)-based constant heavy domain expressed better and purified to greater levels than a µ-based constant heavy domain based system (FIG. 13, panel B).

EXAMPLE 8

Expression of Surrogate Light Chain Constructs (SURROBODY™) m13 Phagemid

As recombinant proteins are not only usefully expressed in bacteria but also individually and in diverse library collections on the surface of bacterial virus particles we wished to produce soluble surrogate light chain constructs on the surface of m13 phagemids. To address this, surrogate light chain fusions ("dimers" in FIG. 11) were clones into *E. coli* expression/secretion systems. For all systems a pLac repressible expression system described above was used. However, in this case we appended an E-tag epitope (GAPVPYPDPLEPR) (SEQ ID NO: 16) to the surrogate light chain fusions, as well as to a light chain control protein. The sequences of the geneIII VpreB1-lambda5-E tag fusion (Fusion 1) and the geneIII VpreB1-C1-E tag fusion (Fusion 2) are shown as SEQ ID NOs: 12 and 13, respectively. To anchor the heavy chain constructs to the in 13 phagemid the heavy chain constructs were recombinantly cloned the variable heavy chains and gamma constant heavy domain 1 regions in frame with the m13 gene III product. Specifically the recombinant proteins contained an intervening, a hexahistidine peptide, the peptide epitope for the anti-c-myc antibody (GEQKLISLEEDL) (SEQ ID NO: 17), and amber stop codon. We examined the fidelity of protein expression and complex formation respectively by anti-histidine and anti-E capture ELISA.

Figure 14A:
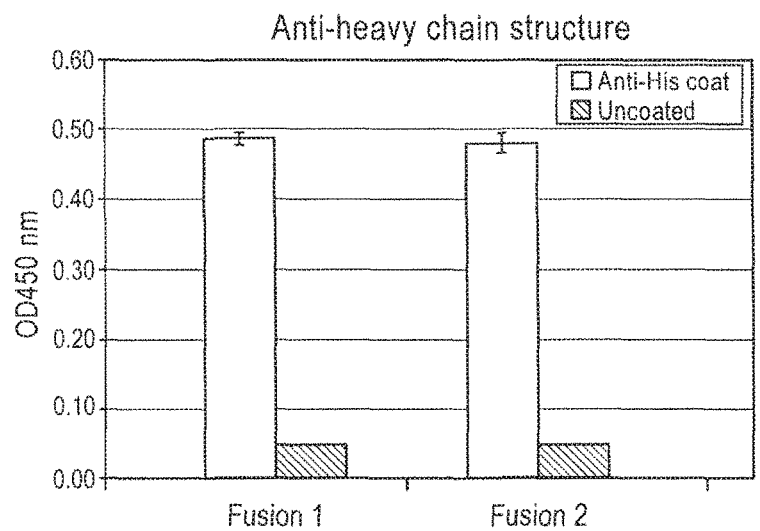
FIG. 14A-FIG. 14B: Phage surrogate light chain construct capture ELISA via anti-phage detection.
Figure 14B:
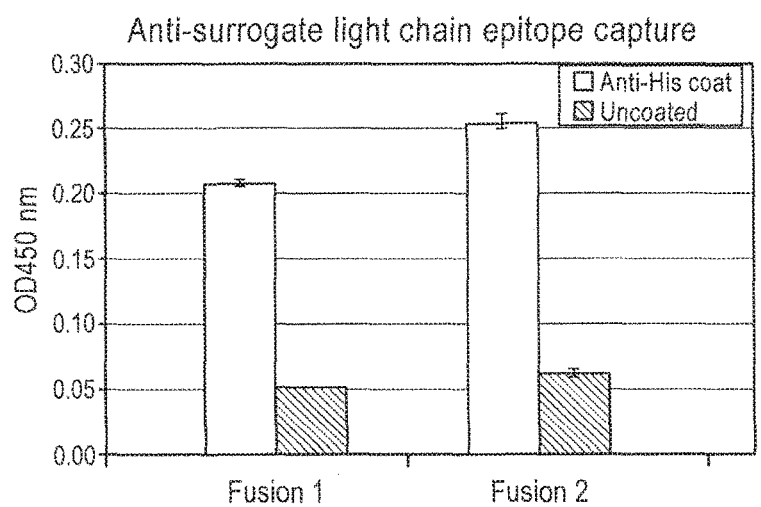
Figure 15:
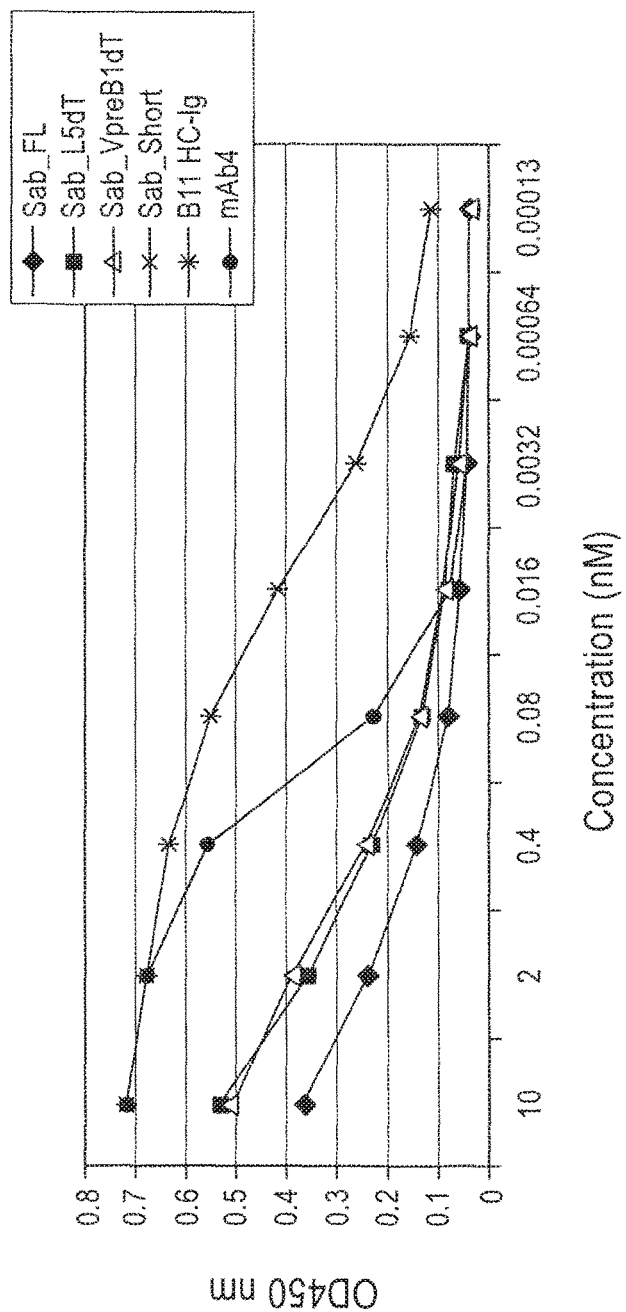
FIG. 15: Purified surrogate light chain constructs expressed in mammalian cells bind viral target.
Figure 22A:
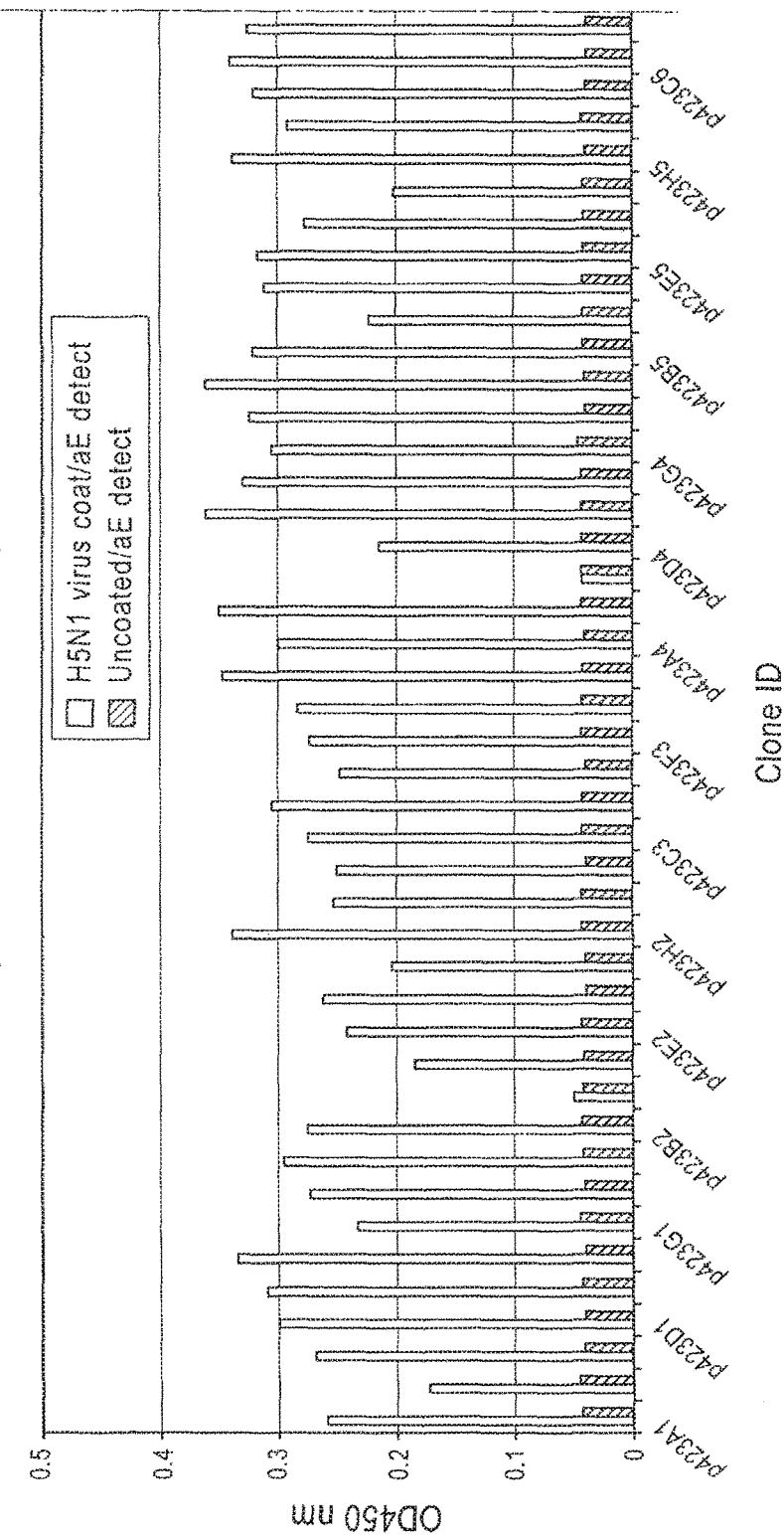
Figure 22C:
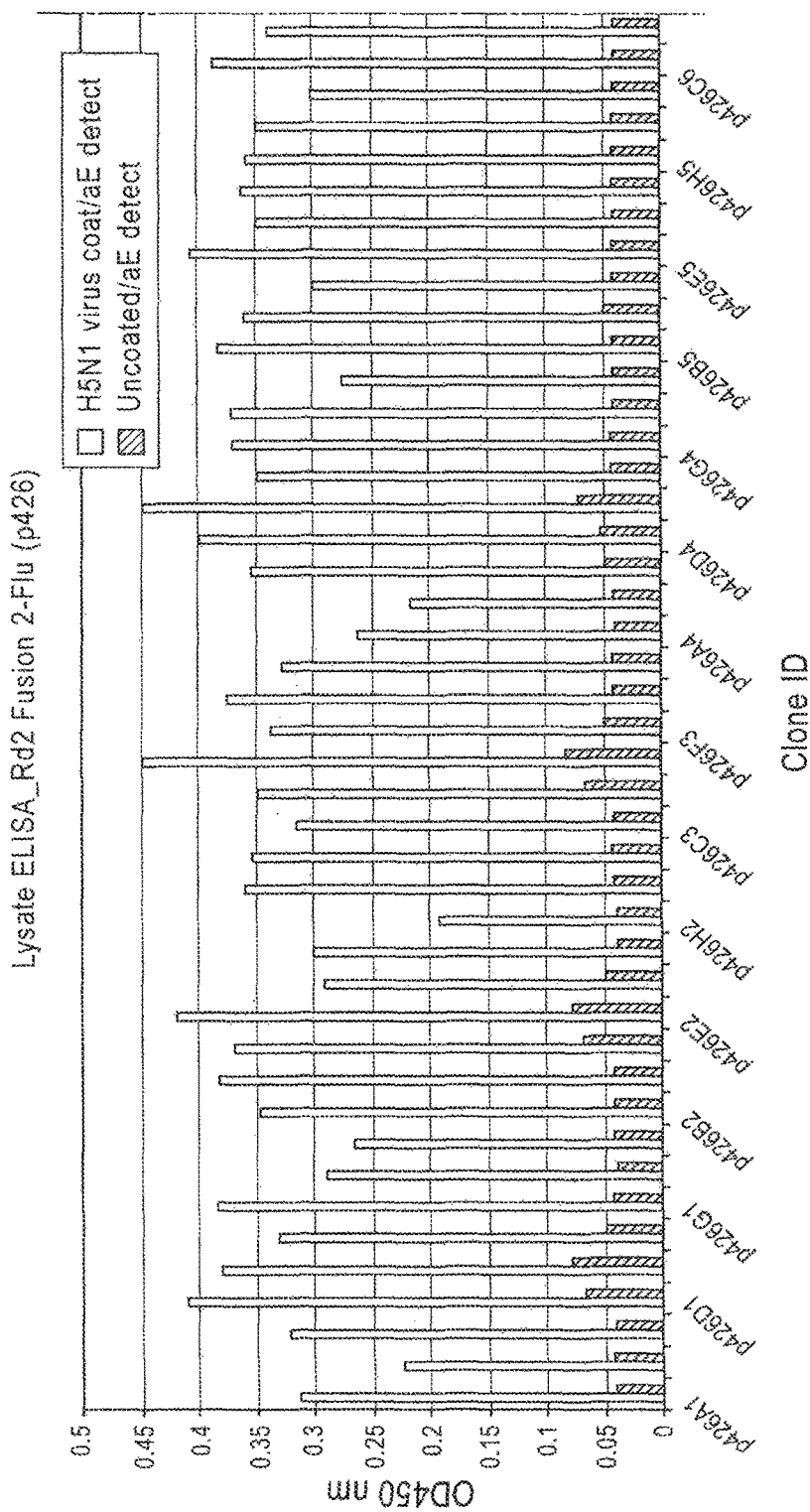
Figure 22D:
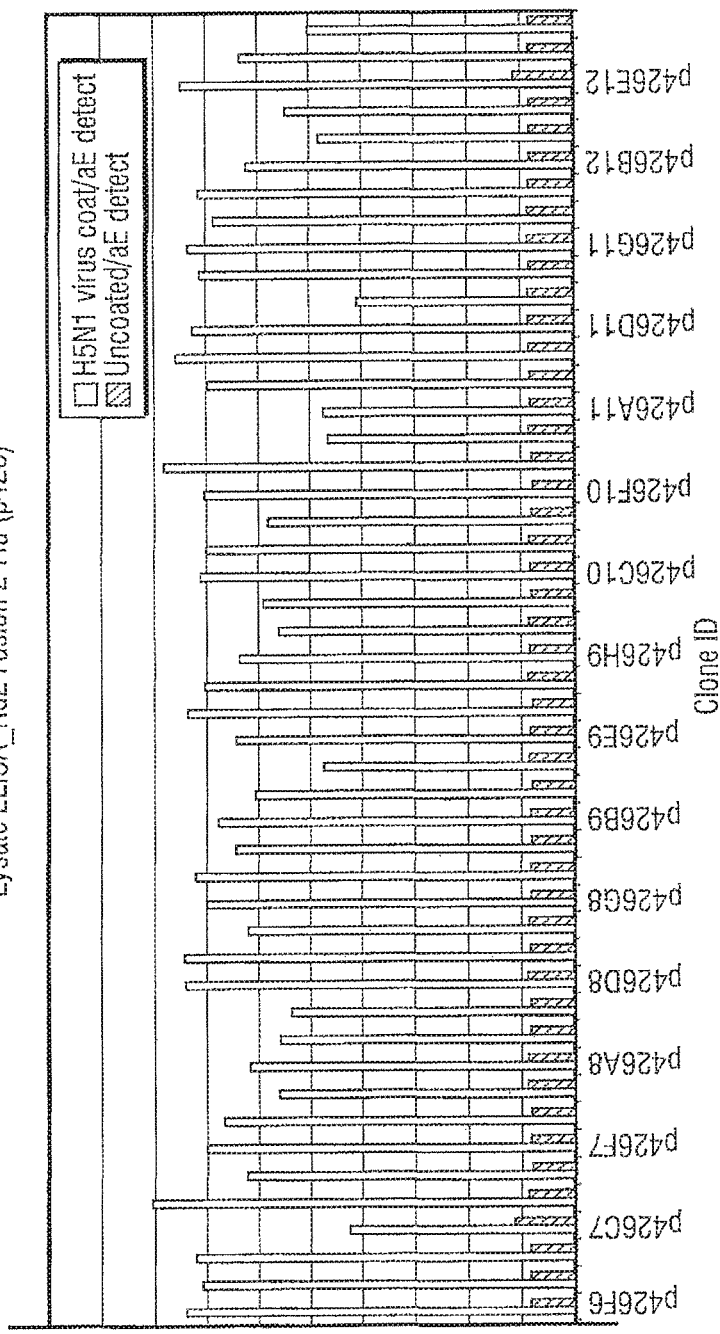

Phagemid expression of antibodies and surrogate light chain constructs (e.g., SURROBODIES™) were accomplished by standard methods well known in the art. Essentially, TG-1 cells transformed with expression plasmids were grown to mid log (OD 600~0.3) in 2-YT media supplemented with 100 mcg/ml ampicillin and 2% glucose repression and then infected with m13K07 helper phage and then grown overnight in 2-YT media supplemented with 100 mcg ampicillin, 70 mcg/ml kanamycin, and 200 micromolar IPTG. Phage containing supernatants or precipitated and PBS resuspended phage were used for phage capture ELISA. The phage capture ELISA was accomplished by coating microtiter plates with either anti-histidine (Serotec) or anti-E antibodies (Abcam) and then detecting binding with anti-m13 peroxidase antibodies (Pharmacia), followed by colorimetric visualization with TMB substrate. In these instances we found specific capture of the phage by both methods, supporting high fidelity protein expression fusion to phage by the heavy chains and stable surrogate light chain association. The results are shown in FIG. 14.

EXAMPLE 9

Antigen Binding of Surrogate Light Chain Constructs Expressed in Mammalian Cells As it appeared that the surrogate light chain variants formed readily detectable complexes following nickel chelate chromatography, their ability to bind the parent antigen of cognate heavy chain partner was tested. Transient expression and purification were performed as described above. Antigen binding was tested by ELISA. Briefly, microtiter wells were coated with inactivated H5N1 Vietnam 12-3/04 virus preparations (USFDA-CBER, antigen standard), blocked and then incubated with quantified serially diluted purified proteins. After washing, the complexes were detected with anti-human Fc peroxidase conjugated antibodies. Finally, binding was colorimetrially visualized and quantitated with TMB substrate development (see FIG. 15).

Additionally, supernatants from transient transfections were similarly tested undiluted for antigen binding and shown in FIG. 16. After washing, the surrogate light chain complexes were detected with either anti-VpreB1 anti-peptide sera and anti-rabbit peroxidase conjugated secondary or anti-human Fc peroxidase conjugated antibodies and then colorimetrically visualized and quantitated with TMB substrate development.

EXAMPLE 10

Antigen Binding of Surrogate Light Chain Constructs Expressed in *E. coli*

Because the surrogate light chain fusions appeared to form stable complexes we wanted to establish whether such fusions paired with a heavy chain from and anti-influenza antibody would bind the antibody's cognate virus. To test for binding periplasmic lysates were prepared as described above. The lysates were then subjected to ELISA antigen binding, essentially as described above, except binding was detected with either a monoclonal antibody to an appended hexahistidine epitope at the C-terminus of the heavy chain or to an appended E-tag at the C-terminus of the surrogate light chain fusion via polyclonal affinity purified antibodies. Epitope detection was accomplished by either anti-mouse or anti-rabbit peroxidase conjugated antibodies. Finally, binding was colorimetrically visualized and quantitated with TMB substrate development. The results are shown in FIG. 17.

EXAMPLE 11

Antigen Binding of Phage Displayed Surrogate Light Chain Constructs

Because it was possible to make surrogate light chain variants in heterologous systems, and as phage displayed collections are desirable to future protein discovery and engineering, we wanted to determine whether the surrogate light chain variants and/or fusions were readily displayed on the surface of m13 phage as gene III-associated complexes. The variants (SEQ ID NOs: 18-22) and previously described fusions (SEQ ID NOs: 12 and 13) were coexpressed with either of two anti-influenza antibody heavy chains (SEQ ID NOs: 19 and 14) as described above and binding followed essentially the conditions also described above. Briefly, microliter wells were coated with H5N1 Vietnam 1203/04 virus and phagemid were allowed to bind and then washed and detected directly through anti-m13 peroxidase conjugated antibodies. Binding was quantitatively determined following colorimetric substrate product formation with TMB. The results are shown in FIGS. 18 and 19.

EXAMPLE 12

Phage Surrogate Light Chain Construct Library Constructions, Selection, and Clonal ELISA An iterative approach using combinatorial antibody libraries was employed to generate and test surrogate light chain constructs that bound antigen. Briefly, combinatorial antibody libraries prepared from the bone marrow of H5N1 avian influenza survivors were created. These libraries were screened against H5N1 viral hemagglutinin protein for two rounds of selection. Next the phagemid plasmid was amplified and purified. Heavy chain variable regions isolated by restriction digest from this plasmid preparation and cloned in frame with the constant heavy domain 1 to form a recombinant fusion to the m13 gene III coat protein for phagemid display. Importantly, we used two recipient plasmids that either coexpressed a surrogate light chain fusion comprised of VpreB1 and lambda 5 (SLC fusion 1) (SEQ ID NO: 10) or VpreB1 and a constant lambda domain (SEQ ID NO: 11) from the classical lambda light chain (SLC fusion 2). The fusion 1 library produced $3.84 \times 10^7$ independent transformants, while the fusion 2 library produced $7.8 \times 10^7$ transformants. Both libraries were screened independently through two rounds and both showed significant enrichment over background (Fusion 1=5×, Fusion 2=20×) that increased in a second round of panning (Fusion 1=97×, Fusion 2=48×).

To test by ELISA for clonal antigen binding phage from both rounds and both libraries were transferred into the HB2151 *E. coli* strain to produce soluble surrogate light chain construct fusion proteins (e.g., SURROBODY™ fusion proteins). Briefly, HB2151 clones were grown and induced to produce soluble surrogate light chain constructs (e.g., soluble SURROBODIES™). Specifically, colonies were cultured overnight in 2-YT media supplemented with 100 mcg/ml ampicillin and 200 micromolar IPTG overnight at 30 degrees the periplasmic lysates, as described above. The resulting periplasmic lysates were tested by ELISA, essentially as outlined above.

The number of transformants and percent positive clones for the two fusions, at rounds 1 and 2 of panning are shown in FIG. 20, and the clonal analysis data for Rounds 1 and 2 of Fusion 1 and Fusion 2 library clones are shown in FIGS. 21A-21D and FIGS. 22A-22D.

EXAMPLE 13

Surrogate Light Chain Fusions to Increase Serum Half-Life

The half-life of an antibody fragment in vivo is extended considerably when it is part of a fusion to an intact and complete heavy chain that includes all heavy chain constant domains, not just those necessary to form a stable antigen binding fragment. In the case of IgG this means the inclusion of domains CH1, CH2, and CH3. In particular it is well established that CH2 and CH3 confer the majority of this effect in vivo. In fact fusion of these CH2 and CH3 domains to heterologous proteins is typically sufficient to improve the potencies and PK/PD of these chimeric molecules compared to the parent molecules. Similarly functional fusions to the either or both VpreB and λ5 benefit by this association with the constant domains of the heavy chain.

For the treatment of type II diabetes administration of glucagon-like peptide 1 (or GLP-1) benefits individuals by inducing glucose-dependent insulin secretion in the pancreas, thereby improving glucose management in those patients. However, a long-lived GLP-1 peptide is a desirable goal. As the tails of the surrogate light chains are distinct and accessible, we could accomplish this goal by either recombinantly fusing the active GLP-1 moiety to either the C-terminus of the VpreB1 tail (SEQ ID NOs: 23 and 24) or the N-terminal tail of λ5 (SEQ ID NOs: 25 and 26). In the case of a λ5 fusion we may express this in the presence or absence of vpreB1 and even in the presence or absence of the Variable heavy domain, as depicted in FIG. 11. Fusions to VpreB1 can similarly be made in the presence or absence of λ5, and possibly with or without the CH1 domain of the heavy chain. Similarly, other beneficial growth factor, cytokine, receptor, and enzyme fusions may be created. In all of these cases binding is not requisite of the surrogate light chain, or surrogate light chain construct components (e.g., SURROBODY™ components), but rather may be conferred either entirely or in large part by the heterologous surrogate light chain fused element.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

EXAMPLE 14

Affinity Determination of Hemagglutinin-Binding Surrogate Light Chain Constructs To determine the affinities of fusion surrogate light chain constructs (SURROBODIES™, see, FIG. 11) we overexpressed and purified various surrogate light chain constructs (e.g., SURROBODIES™) in *E. coli* and compared them to the parental Fabs from which the heavy chains were first identified. Affinities were determined by Bio-Layer interferometry on a BioForte Octet essentially as follows. First 100 μg of purified hemagglutinin protein was biotinlyated at a 20:1 molar excess using Pierce No-Weigh PEO4 biotin (cat#21329) according to manufacturer's instructions, incubated at room temperature for 1-3 hours with intermittent mixing and then incubated overnight at 4C. The excess biotin was removed by size exclusion spin column and exchanged into PBS. Next, HA binding surrogate light chain constructs and Fabs were purified by FPLC using $Ni^{2+}$ affinity chromatography, desalted to remove excess imidazole, concentrated, and quantitated by quantitative light chain ELISAs (Bethel Labs, cat#E80-115-κ, and E80-116-λ) are performed according to the manufacturer's instructions. Finally affinities were determined by analyzing a range of sample concentrations that are typically 15 nM-500 nM in serial 2 fold dilutions. The samples were incubated with biosensors coated with HA protein for up to 15 minutes, then incubated in sample diluent for up to 1 hour. All of these steps were done with sample plate rotation at 1500 RPM. Association was measured during the Fab incubation with the HA-coated biosensors and dissociation is measured in the sample diluent incubation following binding. Affinities are shown in the following Table.

| Clone | Fusion 1 VpreB1-Lambda5 | Fusion 1 VpreB1-constant lambda | Fab |
|---|---|---|---|
| F5 | 250-400 pM | 150-270 pM | 1 pM |
| B11 | 31-180 pM | Not determined | 13 pM |

All references cited throughout the specification, and the references cited therein, are hereby expressly incorporated by reference in their entirety.

The invention claimed is:

1. A tetrameric construct comprising:
   (a) a first and a second surrogate light chain fusion polypeptide, each comprising the amino acid sequence of SEQ ID NO: 10, and;
   (b) a first and a second antibody heavy chain polypeptide comprising, from N-terminus to C-terminus, a heavy chain variable region (VH), a heavy chain first constant region (CH1), a hinge region, a heavy chain second constant region (CH2), and a heavy chain third constant region (CH3), wherein each antibody heavy chain polypeptide comprises the amino acid sequence of SEQ ID NO: 9,
   wherein the first surrogate light chain fusion polypeptide is non-covalently conjugated to the first antibody heavy chain polypeptide, wherein the second surrogate light chain fusion polypeptide is non-covalently conjugated to the second antibody heavy chain polypeptide, and wherein the construct is capable of specifically binding to a target, wherein the target is an influenza A virus.

2. A tetrameric construct comprising:
   (a) a first and a second surrogate light chain fusion polypeptide, each comprising the amino acid sequence of SEQ ID NO: 10, and;
   (b) a first and a second antibody heavy chain polypeptide comprising, from N-terminus to C-terminus, a heavy chain variable region (VH), a heavy chain first constant region (CH1), a hinge region, a heavy chain second constant region (CH2), and a heavy chain third constant region (CH3), wherein each antibody heavy chain polypeptide comprises the amino acid sequence of SEQ ID NO: 14,
   wherein the first surrogate light chain fusion polypeptide is non-covalently conjugated to the first antibody heavy chain polypeptide, wherein the second surrogate light chain fusion polypeptide is non-covalently conjugated to the second antibody heavy chain polypeptide, and wherein the construct is capable of specifically binding to a target, wherein the target is an influenza A virus.

* * * * *

SEQUENCE LISTING

<160> NUMBER OF SEQ ID NOS: 35

<210> SEQ ID NO 1
<211> LENGTH: 145
<212> TYPE: PRT
<213> ORGANISM: Homo sapiens

<400> SEQUENCE: 1

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
        115                 120                 125

Arg Glu Trp Glu Glu Glu Met Glu Pro Thr Ala Ala Arg Thr Arg Val
    130                 135                 140

Pro
145

<210> SEQ ID NO 2
<211> LENGTH: 142
<212> TYPE: PRT
<213> ORGANISM: Mus sp.

<400> SEQUENCE: 2

Met Ala Trp Thr Ser Val Leu Leu Met Leu Leu Ala His Leu Thr Gly
1               5                   10                  15

Cys Gly Pro Gln Pro Met Val His Gln Pro Pro Ser Ala Ser Ser Ser
            20                  25                  30

Leu Gly Ala Thr Ile Arg Leu Ser Cys Thr Leu Ser Asn Asp His Asn
        35                  40                  45

Ile Gly Ile Tyr Ser Ile Tyr Trp Tyr Gln Gln Arg Pro Gly His Pro
    50                  55                  60

Pro Arg Phe Leu Leu Arg Tyr Phe Ser His Ser Asp Lys His Gln Gly
65                  70                  75                  80

Pro Asp Ile Pro Pro Arg Phe Ser Gly Ser Lys Asp Thr Ala Arg Asn
                85                  90                  95

Leu Gly Tyr Leu Ser Ile Ser Glu Leu Gln Pro Glu Asp Glu Ala Val
            100                 105                 110

Tyr Tyr Cys Ala Val Gly Leu Arg Ser His Glu Lys Lys Arg Met Glu
        115                 120                 125

Arg Glu Trp Glu Gly Glu Lys Ser Tyr Thr Asp Leu Gly Ser
    130                 135                 140

<210> SEQ ID NO 3
<211> LENGTH: 171
<212> TYPE: PRT

<213> ORGANISM: Mus sp.

<400> SEQUENCE: 3

Met Ala Trp Thr Ser Val Leu Leu Met Leu Leu Ala His Leu Thr Gly
1               5                   10                  15

Lys Gly Thr Leu Gly Val Gln Gly Phe Leu Ala Pro Pro Val Ala Leu
            20                  25                  30

Leu Cys Pro Ser Asp Gly His Ala Ser Ile Phe Ser Gly Cys Gly Pro
        35                  40                  45

Gln Pro Met Val His Gln Pro Pro Ser Ala Ser Ser Ser Leu Gly Ala
    50                  55                  60

Thr Ile Arg Leu Ser Cys Thr Leu Ser Asn Asp His Asn Ile Gly Ile
65                  70                  75                  80

Tyr Ser Ile Tyr Trp Tyr Gln Gln Arg Pro Gly His Pro Pro Arg Phe
                85                  90                  95

Leu Leu Arg Tyr Phe Ser His Ser Asp Lys His Gln Gly Pro Asp Ile
            100                 105                 110

Pro Pro Arg Phe Ser Gly Ser Lys Asp Thr Ala Arg Asn Leu Gly Tyr
        115                 120                 125

Leu Ser Ile Ser Glu Leu Gln Pro Glu Asp Ala Val Tyr Tyr Cys
    130                 135                 140

Ala Val Gly Leu Arg Ser His Glu Lys Lys Arg Met Glu Arg Glu Trp
145                 150                 155                 160

Glu Gly Glu Lys Ser Tyr Thr Asp Leu Gly Ser
                165                 170

<210> SEQ ID NO 4
<211> LENGTH: 123
<212> TYPE: PRT
<213> ORGANISM: Homo sapiens

<400> SEQUENCE: 4

Met Ala Cys Arg Cys Leu Ser Phe Leu Leu Met Gly Thr Phe Leu Ser
1               5                   10                  15

Val Ser Gln Thr Val Leu Ala Gln Leu Asp Ala Leu Leu Val Phe Pro
            20                  25                  30

Gly Gln Val Ala Gln Leu Ser Cys Thr Leu Ser Pro Gln His Val Thr
        35                  40                  45

Ile Arg Asp Tyr Gly Val Ser Trp Tyr Gln Gln Arg Ala Gly Ser Ala
    50                  55                  60

Pro Arg Tyr Leu Leu Tyr Tyr Arg Ser Glu Glu Asp His His Arg Pro
65                  70                  75                  80

Ala Asp Ile Pro Asp Arg Phe Ser Ala Ala Lys Asp Glu Ala His Asn
                85                  90                  95

Ala Cys Val Leu Thr Ile Ser Pro Val Gln Pro Glu Asp Asp Ala Asp
            100                 105                 110

Tyr Tyr Cys Ser Val Gly Tyr Gly Phe Ser Pro
        115                 120

<210> SEQ ID NO 5
<211> LENGTH: 209
<212> TYPE: PRT
<213> ORGANISM: Homo sapiens

<400> SEQUENCE: 5

Met Lys Leu Arg Val Gly Gln Thr Leu Gly Thr Ile Pro Arg Gln Cys
1               5                   10                  15

```
Glu Val Leu Leu Leu Leu Leu Gly Leu Val Asp Gly Val His
             20                  25                  30

His Ile Leu Ser Pro Ser Ser Ala Glu Arg Ser Arg Ala Val Gly Pro
             35                  40                  45

Gly Ala Ser Val Gly Ser Asn Arg Pro Ser Leu Trp Ala Leu Pro Gly
 50                  55                  60

Arg Leu Leu Phe Gln Ile Ile Pro Arg Gly Ala Gly Pro Arg Cys Ser
 65                  70                  75                  80

Pro His Arg Leu Pro Ser Lys Pro Gln Phe Trp Tyr Val Phe Gly Gly
                 85                  90                  95

Gly Thr Gln Leu Thr Ile Leu Gly Gln Pro Lys Ser Asp Pro Leu Val
                100                 105                 110

Thr Leu Phe Leu Pro Ser Leu Lys Asn Leu Gln Pro Thr Arg Pro His
            115                 120                 125

Val Val Cys Leu Val Ser Glu Phe Tyr Pro Gly Thr Leu Val Val Asp
130                 135                 140

Trp Lys Val Asp Gly Val Pro Val Thr Gln Gly Val Glu Thr Thr Gln
145                 150                 155                 160

Pro Ser Lys Gln Thr Asn Asn Lys Tyr Met Val Ser Ser Tyr Leu Thr
                165                 170                 175

Leu Ile Ser Asp Gln Trp Met Pro His Ser Arg Tyr Ser Cys Arg Val
            180                 185                 190

Thr His Glu Gly Asn Thr Val Glu Lys Ser Val Ser Pro Ala Glu Cys
            195                 200                 205

Ser

<210> SEQ ID NO 6
<211> LENGTH: 213
<212> TYPE: PRT
<213> ORGANISM: Homo sapiens

<400> SEQUENCE: 6

Met Arg Pro Gly Thr Gly Gln Gly Gly Leu Glu Ala Pro Gly Glu Pro
  1               5                  10                  15

Gly Pro Asn Leu Arg Gln Arg Trp Pro Leu Leu Leu Gly Leu Ala
             20                  25                  30

Val Val Thr His Gly Leu Leu Arg Pro Thr Ala Ala Ser Gln Ser Arg
             35                  40                  45

Ala Leu Gly Pro Gly Ala Pro Gly Gly Ser Ser Arg Ser Ser Leu Arg
 50                  55                  60

Ser Arg Trp Gly Arg Phe Leu Leu Gln Arg Gly Ser Trp Thr Gly Pro
 65                  70                  75                  80

Arg Cys Trp Pro Arg Gly Phe Gln Ser Lys His Asn Ser Val Thr His
                 85                  90                  95

Val Phe Gly Ser Gly Thr Gln Leu Thr Val Leu Ser Gln Pro Lys Ala
                100                 105                 110

Thr Pro Ser Val Thr Leu Phe Pro Pro Ser Ser Glu Glu Leu Gln Ala
            115                 120                 125

Asn Lys Ala Thr Leu Val Cys Leu Met Asn Asp Phe Tyr Pro Gly Ile
130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175
```

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
        210

<210> SEQ ID NO 7
<211> LENGTH: 158
<212> TYPE: PRT
<213> ORGANISM: Artificial Sequence
<220> FEATURE:
<223> OTHER INFORMATION: Synthetic construct

<400> SEQUENCE: 7

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly Leu Ala
            20                  25                  30

Val Val Thr His Gly Ser Val Thr His Val Phe Gly Ser Gly Thr Gln
        35                  40                  45

Leu Thr Val Leu Ser Gln Pro Lys Ala Thr Pro Ser Val Thr Leu Phe
    50                  55                  60

Pro Pro Ser Ser Glu Glu Leu Gln Ala Asn Lys Ala Thr Leu Val Cys
65                  70                  75                  80

Leu Met Asn Asp Phe Tyr Pro Gly Ile Leu Thr Val Thr Trp Lys Ala
                85                  90                  95

Asp Gly Thr Pro Ile Thr Gln Gly Val Glu Met Thr Thr Pro Ser Lys
            100                 105                 110

Gln Ser Asn Asn Lys Tyr Ala Ala Ser Ser Tyr Leu Ser Leu Thr Pro
        115                 120                 125

Glu Gln Trp Arg Ser Arg Arg Ser Tyr Ser Cys Gln Val Met His Glu
    130                 135                 140

Gly Ser Thr Val Glu Lys Thr Val Ala Pro Ala Glu Cys Ser
145                 150                 155

<210> SEQ ID NO 8
<211> LENGTH: 119
<212> TYPE: PRT
<213> ORGANISM: Artificial Sequence
<220> FEATURE:
<223> OTHER INFORMATION: Synthetic construct

<400> SEQUENCE: 8

Met Ser Trp Ala Pro Val Leu Leu Met Leu Phe Val Tyr Cys Thr Gly
1               5                   10                  15

Cys Gly Pro Gln Pro Val Leu His Gln Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met

Tyr Tyr Cys Ala Met Gly Ala
            115

<210> SEQ ID NO 9
<211> LENGTH: 480
<212> TYPE: PRT
<213> ORGANISM: Artificial Sequence
<220> FEATURE:
<223> OTHER INFORMATION: Synthetic construct

<400> SEQUENCE: 9

Met Glu Thr Asp Thr Leu Leu Leu Trp Val Leu Leu Leu Trp Val Pro
  1               5                  10                  15

Gly Ser Thr Gly Asp Ala Gln Met Gln Leu Gln Glu Ser Gly Pro Gly
             20                  25                  30

Leu Val Lys Pro Ser Glu Thr Leu Ser Leu Thr Cys Thr Val Ser Gly
         35                  40                  45

Tyr Ser Phe Asp Ser Gly Tyr Tyr Trp Gly Trp Leu Arg Gln Pro Pro
     50                  55                  60

Gly Lys Gly Leu Glu Trp Ile Gly Ser Ile Tyr His Ser Arg Asn Thr
 65                  70                  75                  80

Tyr Tyr Asn Pro Ser Leu Lys Ser Arg Val Thr Ile Ser Val Asp Thr
                 85                  90                  95

Ser Lys Asn Gln Phe Ser Leu Gln Leu Ser Ser Val Thr Ala Ala Asp
            100                 105                 110

Thr Ala Val Tyr Tyr Cys Ala Arg Gly Thr Trp Tyr Ser Ser Asn Leu
        115                 120                 125

Arg Tyr Trp Phe Asp Pro Trp Gly Lys Gly Thr Leu Val Arg Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser

```
                    340                 345                 350
Asn Lys Ala Leu Pro Ala Pro Ile Glu Lys Thr Ile Ser Lys Ala Lys
                355                 360                 365
Gly Gln Pro Arg Glu Pro Gln Val Tyr Thr Leu Pro Pro Ser Arg Glu
            370                 375                 380
Glu Met Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
            435                 440                 445
Asn Val Phe Ser Cys Ser Val Met His Glu Ala Leu His Asn His Tyr
            450                 455                 460
Thr Gln Lys Ser Leu Ser Leu Ser Pro Gly His His His His His His
465                 470                 475                 480

<210> SEQ ID NO 10
<211> LENGTH: 242
<212> TYPE: PRT
<213> ORGANISM: Artificial Sequence
<220> FEATURE:
<223> OTHER INFORMATION: Synthetic construct

<400> SEQUENCE: 10

Met Ser Trp Ala Pro Val Leu Leu Met Leu Phe Val Tyr Cys Thr Gly
1               5                   10                  15
Cys Gly Pro Gln Pro Val Leu His Gln Pro Pro Ala Met Ser Ser Ala
                20                  25                  30
Leu Gly Thr Thr Ile Arg Leu Thr Cys Thr Leu Arg Asn Asp His Asp
            35                  40                  45
Ile Gly Val Tyr Ser Val Tyr Trp Tyr Gln Gln Arg Pro Gly His Pro
        50                  55                  60
Pro Arg Phe Leu Leu Arg Tyr Phe Ser Gln Ser Asp Lys Ser Gln Gly
65                  70                  75                  80
Pro Gln Val Pro Pro Arg Phe Ser Gly Ser Lys Asp Val Ala Arg Asn
                85                  90                  95
Arg Gly Tyr Leu Ser Ile Ser Glu Leu Gln Pro Glu Asp Glu Ala Met
            100                 105                 110
Tyr Tyr Cys Ala Met Gly Ala Arg Ser Ser Val Thr His Val Phe Gly
            115                 120                 125
Ser Gly Thr Gln Leu Thr Val Leu Ser Gln Pro Lys Ala Thr Pro Ser
        130                 135                 140
Val Thr Leu Phe Pro Pro Ser Ser Glu Glu Leu Gln Ala Asn Lys Ala
145                 150                 155                 160
Thr Leu Val Cys Leu Met Asn Asp Phe Tyr Pro Gly Ile Leu Thr Val
                165                 170                 175
Thr Trp Lys Ala Asp Gly Thr Pro Ile Thr Gln Gly Val Glu Met Thr
            180                 185                 190
Thr Pro Ser Lys Gln Ser Asn Asn Lys Tyr Ala Ala Ser Ser Tyr Leu
        195                 200                 205
Ser Leu Thr Pro Glu Gln Trp Arg Ser Arg Arg Ser Tyr Ser Cys Gln
    210                 215                 220
Val Met His Glu Gly Ser Thr Val Glu Lys Thr Val Ala Pro Ala Glu
```

<210> SEQ ID NO 11
<211> LENGTH: 242
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (153)..(153)
<223> OTHER INFORMATION: Any amino acid

<400> SEQUENCE: 11

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Val Thr His Val Phe Gly
        115                 120                 125

Ser Gly Thr Gln Leu Thr Val Leu Gly Gln Pro Lys Ala Ala Pro Ser
130                 135                 140

Val Thr Leu Phe Pro Pro Ser Ser Xaa Glu Leu Gln Ala Asn Lys Ala
145                 150                 155                 160

Thr Leu Val Cys Leu Ile Ser Asp Phe Tyr Pro Gly Ala Val Thr Val
                165                 170                 175

Ala Trp Lys Ala Asp Ser Ser Pro Val Lys Ala Gly Val Glu Thr Thr
            180                 185                 190

Thr Pro Ser Lys Gln Ser Asn Asn Lys Tyr Ala Ala Ser Ser Tyr Leu
        195                 200                 205

Ser Leu Thr Pro Glu Gln Trp Lys Ser His Arg Ser Tyr Ser Cys Gln
    210                 215                 220

Val Thr His Glu Gly Ser Thr Val Glu Lys Thr Val Ala Pro Ala Glu
225                 230                 235                 240

Cys Ser

<210> SEQ ID NO 12
<211> LENGTH: 256
<212> TYPE: PRT
<213> ORGANISM: Artificial Sequence
<220> FEATURE:
<223> OTHER INFORMATION: Synthetic construct

<400> SEQUENCE: 12

Val Lys Lys Leu Leu Phe Ala Ile Pro Leu Val Val Pro Phe Tyr
1               5                   10                  15

Ser His Ser Ala Gln Pro Val Leu His Gln Pro Pro Ala Met Ser Ser

```
            20                  25                  30
Ala Leu Gly Thr Thr Ile Arg Leu Thr Cys Thr Leu Arg Asn Asp His
            35                  40                  45

Asp Ile Gly Val Tyr Ser Val Tyr Trp Tyr Gln Gln Arg Pro Gly His
        50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Val Thr His Val Phe
        115                 120                 125

Gly Ser Gly Thr Gln Leu Thr Val Leu Ser Gln Pro Lys Ala Thr Pro
    130                 135                 140

Ser Val Thr Leu Phe Pro Pro Ser Ser Glu Glu Leu Gln Ala Asn Lys
145                 150                 155                 160

Ala Thr Leu Val Cys Leu Met Asn Asp Phe Tyr Pro Gly Ile Leu Thr
                165                 170                 175

Val Thr Trp Lys Ala Asp Gly Thr Pro Ile Thr Gln Gly Val Glu Met
            180                 185                 190

Thr Thr Pro Ser Lys Gln Ser Asn Asn Lys Tyr Ala Ala Ser Ser Tyr
        195                 200                 205

Leu Ser Leu Thr Pro Glu Gln Trp Arg Ser Arg Ser Tyr Ser Cys
    210                 215                 220

Gln Val Met His Glu Gly Ser Thr Val Glu Lys Thr Val Ala Pro Ala
225                 230                 235                 240

Glu Cys Ser Gly Ala Pro Val Pro Tyr Pro Asp Pro Leu Glu Pro Arg
                245                 250                 255
```

<210> SEQ ID NO 13
<211> LENGTH: 256
<212> TYPE: PRT
<213> ORGANISM: Artificial Sequence
<220> FEATURE:
<223> OTHER INFORMATION: Synthetic construct

<400> SEQUENCE: 13

```
Val Lys Lys Leu Leu Leu Phe Ala Ile Pro Leu Val Val Pro Phe Tyr
1               5                   10                  15

Ser His Ser Ala Gln Pro Val Leu His Gln Pro Pro Ala Met Ser Ser
            20                  25                  30

Ala Leu Gly Thr Thr Ile Arg Leu Thr Cys Thr Leu Arg Asn Asp His
            35                  40                  45

Asp Ile Gly Val Tyr Ser Val Tyr Trp Tyr Gln Gln Arg Pro Gly His
        50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Val Thr His Val Phe
        115                 120                 125

Gly Ser Gly Thr Gln Leu Thr Val Leu Arg Gln Pro Lys Ala Ala Pro
```

```
              130                 135                 140
Ser Val Thr Leu Phe Pro Ser Ser Glu Glu Leu Gln Ala Asn Lys
145                 150                 155                 160

Ala Thr Leu Val Cys Leu Ile Ser Asp Phe Tyr Pro Gly Ala Val Thr
                165                 170                 175

Val Ala Trp Lys Ala Asp Gly Ser Pro Val Lys Ala Gly Val Glu Thr
                180                 185                 190

Thr Thr Pro Ser Lys Gln Ser Asn Asn Lys Tyr Ala Ala Ser Ser Tyr
                195                 200                 205

Leu Ser Leu Thr Pro Glu Gln Trp Lys Ser His Lys Ser Tyr Ser Cys
                210                 215                 220

Gln Val Thr His Glu Gly Ser Thr Val Glu Lys Thr Val Ala Pro Thr
225                 230                 235                 240

Glu Cys Ser Gly Ala Pro Val Pro Tyr Pro Asp Pro Leu Glu Pro Arg
                245                 250                 255

<210> SEQ ID NO 14
<211> LENGTH: 269
<212> TYPE: PRT
<213> ORGANISM: Artificial Sequence
<220> FEATURE:
<223> OTHER INFORMATION: Synthetic construct

<400> SEQUENCE: 14

Met Lys Tyr Leu Leu Pro Thr Ala Ala Ala Gly Leu Leu Leu Leu Ala
 1                5                  10                 15

Ala Gln Pro Ala Met Ala Gln Val Gln Leu Gln Glu Ser Gly Gly Gly
                20                  25                  30

Leu Val Gln Pro Gly Gly Ser Leu Arg Leu Ser Cys Ala Ala Ser Gly
                35                  40                  45

Phe Pro Phe Ser Ser Tyr Val Met Ile Trp Val Arg Gln Val Pro Gly
             50                  55                  60

Lys Gly Leu Glu Trp Val Ser Ala Ile Gly Gly Ser Gly Gly Ser Thr
 65                 70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Asp Asp
                100                 105                 110

Thr Ala Val Tyr Tyr Cys Val Leu Ser Pro Lys Ser Tyr Tyr Asp Asn
                115                 120                 125

Ser Gly Ile Tyr Phe Asp Phe Trp Gly Lys Gly Thr Leu Val Arg Val
                130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
                180                 185                 190

Thr Ser Gly Val His Thr Phe Pro Ala Val Leu Gln Ser Ser Gly Leu
                195                 200                 205

Tyr Ser Leu Ser Ser Val Val Thr Val Pro Ser Ser Ser Leu Gly Thr
                210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Ala Ala Ala His His His His
```

His His Gly Glu Gln Lys Leu Ile Ser Glu Glu Asp Leu
                245                 250                 255

<210> SEQ ID NO 15
<211> LENGTH: 271
<212> TYPE: PRT
<213> ORGANISM: Artificial Sequence
<220> FEATURE:
<223> OTHER INFORMATION: Synthetic construct

<400> SEQUENCE: 15

Met Lys Tyr Leu Leu Pro Thr Ala Ala Gly Leu Leu Leu Leu Ala Ala
 1               5                  10                  15

Ala Gln Pro Ala Met Ala Gln Val Gln Leu Gln Glu Ser Gly Gly Gly
            20                  25                  30

Leu Val Gln Pro Gly Gly Ser Leu Arg Leu Ser Cys Ala Ala Ser Gly
        35                  40                  45

Phe Pro Phe Ser Ser Tyr Val Met Ile Trp Val Arg Gln Val Pro Gly
    50                  55                  60

Lys Gly Leu Glu Trp Val Ser Ala Ile Gly Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Asp Asp
            100                 105                 110

Thr Ala Val Tyr Tyr Cys Val Leu Ser Pro Lys Ser Tyr Tyr Asp Asn
        115                 120                 125

Ser Gly Ile Tyr Phe Asp Phe Trp Gly Lys Gly Thr Leu Val Arg Val
    130                 135                 140

Ser Ser Gly Ser Ala Ser Ala Pro Thr Leu Phe Pro Leu Val Ser Cys
145                 150                 155                 160

Glu Asn Ser Pro Ser Asp Thr Ser Ser Val Ala Val Gly Cys Leu Ala
                165                 170                 175

Gln Asp Phe Leu Pro Asp Ser Ile Thr Phe Ser Trp Lys Tyr Lys Asn
            180                 185                 190

Asn Ser Asp Ile Ser Ser Thr Arg Gly Phe Pro Ser Val Leu Arg Gly
        195                 200                 205

Gly Lys Tyr Ala Ala Thr Ser Gln Val Leu Leu Pro Ser Lys Asp Val
    210                 215                 220

Met Gln Gly Thr Asp Glu His Val Val Cys Lys Val Gln His Pro Asn
225                 230                 235                 240

Gly Asn Lys Glu Lys Asn Val Pro Leu Pro Val Ala Ala His His
                245                 250                 255

His His His His Gly Glu Gln Lys Leu Ile Ser Glu Glu Asp Leu
            260                 265                 270

<210> SEQ ID NO 16
<211> LENGTH: 13
<212> TYPE: PRT
<213> ORGANISM: Artificial Sequence
<220> FEATURE:
<223> OTHER INFORMATION: Synthetic peptide

<400> SEQUENCE: 16

Gly Ala Pro Val Pro Tyr Pro Asp Pro Leu Glu Pro Arg
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide

<400> SEQUENCE: 17

Gly Glu Gln Lys Leu Ile Ser Leu Glu Glu Asp Leu
1               5                   10

<210> SEQ ID NO 18
<211> LENGTH: 159
<212> TYPE: PRT
<213> ORGANISM: Artificial Sequence
<220> FEATURE:
<223> OTHER INFORMATION: Synthetic construct

<400> SEQUENCE: 18

Val Lys Lys Leu Leu Phe Ala Ile Pro Leu Val Val Pro Phe Tyr
1               5                   10                  15

Ser His Ser Ala Gln Pro Val Leu His Gln Pro Pro Ala Met Ser Ser
                20                  25                  30

Ala Leu Gly Thr Thr Ile Arg Leu Thr Cys Thr Leu Arg Asn Asp His
            35                  40                  45

Asp Ile Gly Val Tyr Ser Val Tyr Trp Tyr Gln Gln Arg Pro Gly His
        50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Glu Lys Glu Glu Arg
        115                 120                 125

Glu Arg Glu Trp Glu Glu Glu Met Glu Pro Thr Ala Ala Arg Thr Arg
    130                 135                 140

Val Pro Gly Ala Pro Val Pro Tyr Pro Asp Pro Leu Glu Pro Arg
145                 150                 155

<210> SEQ ID NO 19
<211> LENGTH: 120
<212> TYPE: PRT
<213> ORGANISM: Artificial Sequence
<220> FEATURE:
<223> OTHER INFORMATION: Synthetic construct

<400> SEQUENCE: 19

Val Lys Lys Leu Leu Phe Ala Ile Pro Leu Val Val Pro Phe Tyr
1               5                   10                  15

Ser His Ser Ala Gln Pro Val Leu His Gln Pro Pro Ala Met Ser Ser
                20                  25                  30

Ala Leu Gly Thr Thr Ile Arg Leu Thr Cys Thr Leu Arg Asn Asp His
            35                  40                  45

Asp Ile Gly Val Tyr Ser Val Tyr Trp Tyr Gln Gln Arg Pro Gly His
        50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg

Asn Arg Gly Tyr Leu Ser Ile Ser Glu Leu Gln Pro Glu Asp Glu Ala
            100                 105                 110

Met Tyr Tyr Cys Ala Met Gly Ala
            115                 120

<210> SEQ ID NO 20
<211> LENGTH: 133
<212> TYPE: PRT
<213> ORGANISM: Artificial Sequence
<220> FEATURE:
<223> OTHER INFORMATION: Synthetic construct

<400> SEQUENCE: 20

Val Lys Lys Leu Leu Phe Ala Ile Pro Leu Val Val Pro Phe Tyr
  1               5                  10                  15

Ser His Ser Ala Gln Pro Val Leu His Gln Pro Pro Ala Met Ser Ser
                 20                  25                  30

Ala Leu Gly Thr Thr Ile Arg Leu Thr Cys Thr Leu Arg Asn Asp His
             35                  40                  45

Asp Ile Gly Val Tyr Ser Val Tyr Trp Tyr Gln Gln Arg Pro Gly His
         50                  55                  60

Pro Pro Arg Phe Leu Leu Arg Tyr Phe Ser Gln Ser Asp Lys Ser Gln
 65                  70                  75                  80

Gly Pro Gln Val Pro Pro Arg Phe Ser Gly Ser Lys Asp Val Ala Arg
                 85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Gly Ala Pro Val Pro Tyr Pro Asp
            115                 120                 125

Pro Leu Glu Pro Arg
            130

<210> SEQ ID NO 21
<211> LENGTH: 198
<212> TYPE: PRT
<213> ORGANISM: Artificial Sequence
<220> FEATURE:
<223> OTHER INFORMATION: Synthetic construct

<400> SEQUENCE: 21

Met Lys Lys Thr Ala Ile Ala Ile Ala Val Ala Leu Ala Gly Phe Ala
  1               5                  10                  15

Thr Val Ala Gln Ala Ala Leu Leu Arg Pro Thr Ala Ala Ser Gln Ser
                 20                  25                  30

Arg Ala Leu Gly Pro Gly Ala Pro Gly Gly Ser Ser Arg Ser Ser Leu
             35                  40                  45

Arg Ser Arg Trp Gly Arg Phe Leu Leu Gln Arg Gly Ser Trp Thr Gly
         50                  55                  60

Pro Arg Cys Trp Pro Arg Gly Phe Gln Ser Lys His Asn Ser Val Thr
 65                  70                  75                  80

His Val Phe Gly Ser Gly Thr Gln Leu Thr Val Leu Ser Gln Pro Lys
                 85                  90                  95

Ala Thr Pro Ser Val Thr Leu Phe Pro Pro Ser Ser Glu Glu Leu Gln
            100                 105                 110

Ala Asn Lys Ala Thr Leu Val Cys Leu Met Asn Asp Phe Tyr Pro Gly
            115                 120                 125

```
Ile Leu Thr Val Thr Trp Lys Ala Asp Gly Thr Pro Ile Thr Gln Gly
    130                 135                 140

Val Glu Met Thr Thr Pro Ser Lys Gln Ser Asn Asn Lys Tyr Ala Ala
145                 150                 155                 160

Ser Ser Tyr Leu Ser Leu Thr Pro Glu Gln Trp Arg Ser Arg Arg Ser
                165                 170                 175

Tyr Ser Cys Gln Val Met His Glu Gly Ser Thr Val Glu Lys Thr Val
            180                 185                 190

Ala Pro Ala Glu Cys Ser
        195
```

<210> SEQ ID NO 22
<211> LENGTH: 143
<212> TYPE: PRT
<213> ORGANISM: Artificial Sequence
<220> FEATURE:
<223> OTHER INFORMATION: Synthetic construct

<400> SEQUENCE: 22

```
Met Lys Lys Thr Ala Ile Ala Ile Ala Val Ala Leu Ala Gly Phe Ala
  1               5                  10                  15

Thr Val Ala Gln Ala Ala Ser Val Thr His Val Phe Gly Ser Gly Thr
                20                  25                  30

Gln Leu Thr Val Leu Ser Gln Pro Lys Ala Thr Pro Ser Val Thr Leu
            35                  40                  45

Phe Pro Pro Ser Ser Glu Glu Leu Gln Ala Asn Lys Ala Thr Leu Val
        50                  55                  60

Cys Leu Met Asn Asp Phe Tyr Pro Gly Ile Leu Thr Val Thr Trp Lys
 65                  70                  75                  80

Ala Asp Gly Thr Pro Ile Thr Gln Gly Val Glu Met Thr Thr Pro Ser
                85                  90                  95

Lys Gln Ser Asn Asn Lys Tyr Ala Ala Ser Ser Tyr Leu Ser Leu Thr
            100                 105                 110

Pro Glu Gln Trp Arg Ser Arg Arg Ser Tyr Ser Cys Gln Val Met His
        115                 120                 125

Glu Gly Ser Thr Val Glu Lys Thr Val Ala Pro Ala Glu Cys Ser
    130                 135                 140
```

<210> SEQ ID NO 23
<211> LENGTH: 175
<212> TYPE: PRT
<213> ORGANISM: Artificial Sequence
<220> FEATURE:
<223> OTHER INFORMATION: Synthetic construct

<400> SEQUENCE: 23

```
Met Ser Trp Ala Pro Val Leu Leu Met Leu Phe Val Tyr Cys Thr Gly
  1               5                  10                  15

Cys Gly Pro Gln Pro Val Leu His Gln Pro Ala Met Ser Ser Ala
                20                  25                  30

Leu Gly Thr Thr Ile Arg Leu Thr Cys Thr Leu Arg Asn Asp His Asp
            35                  40                  45

Ile Gly Val Tyr Ser Val Tyr Trp Tyr Gln Gln Arg Pro Gly His Pro
        50                  55                  60

Pro Arg Phe Leu Leu Arg Tyr Phe Ser Gln Ser Asp Lys Ser Gln Gly
 65                  70                  75                  80

Pro Gln Val Pro Pro Arg Phe Ser Gly Ser Lys Asp Val Ala Arg Asn
                85                  90                  95
```

```
Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
        115                 120                 125

Arg Glu Trp Glu Glu Met Glu Pro Thr Ala Ala Arg Thr Arg Val
130                 135                 140

Pro His Ala Glu Gly Thr Phe Thr Ser Asp Val Ser Ser Tyr Leu Glu
145                 150                 155                 160

Gly Gln Ala Ala Lys Glu Phe Ile Ala Trp Leu Val Lys Gly Arg
                165                 170                 175

<210> SEQ ID NO 24
<211> LENGTH: 149
<212> TYPE: PRT
<213> ORGANISM: Artificial Sequence
<220> FEATURE:
<223> OTHER INFORMATION: Synthetic construct

<400> SEQUENCE: 24

Met Ser Trp Ala Pro Val Leu Leu Met Leu Phe Val Tyr Cys Thr Gly
  1               5                  10                  15

Cys Gly Pro Gln Pro Val Leu His Gln Pro Ala Met Ser Ser Ala
                 20                  25                  30

Leu Gly Thr Thr Ile Arg Leu Thr Cys Thr Leu Arg Asn Asp His Asp
            35                  40                  45

Ile Gly Val Tyr Ser Val Tyr Trp Tyr Gln Gln Arg Pro Gly His Pro
        50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala His Ala Glu Gly Thr Phe Thr Ser Asp
        115                 120                 125

Val Ser Ser Tyr Leu Glu Gly Gln Ala Ala Lys Glu Phe Ile Ala Trp
    130                 135                 140

Leu Val Lys Gly Arg
145

<210> SEQ ID NO 25
<211> LENGTH: 243
<212> TYPE: PRT
<213> ORGANISM: Artificial Sequence
<220> FEATURE:
<223> OTHER INFORMATION: Synthetic construct

<400> SEQUENCE: 25

Met Arg Pro Gly Thr Gly Gln Gly Gly Leu Glu Ala Pro Gly Glu Pro
  1               5                  10                  15

Gly Pro Asn Leu Arg Gln Arg Trp Pro Leu Leu Leu His Ala Glu
                 20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Lys Gly Arg Gly Leu Ala Val Val
        50                  55                  60

Thr His Gly Leu Leu Arg Pro Thr Ala Ala Ser Gln Ser Arg Ala Leu
```

```
            65                  70                  75                  80
Gly Pro Gly Ala Pro Gly Gly Ser Ser Arg Ser Ser Leu Arg Ser Arg
                85                  90                  95

Trp Gly Arg Phe Leu Leu Gln Arg Gly Ser Trp Thr Gly Pro Arg Cys
               100                 105                 110

Trp Pro Arg Gly Phe Gln Ser Lys His Asn Ser Val Thr His Val Phe
               115                 120                 125

Gly Ser Gly Thr Gln Leu Thr Val Leu Ser Gln Pro Lys Ala Thr Pro
           130                 135                 140

Ser Val Thr Leu Phe Pro Pro Ser Ser Glu Glu Leu Gln Ala Asn Lys
145                 150                 155                 160

Ala Thr Leu Val Cys Leu Met Asn Asp Phe Tyr Pro Gly Ile Leu Thr
                165                 170                 175

Val Thr Trp Lys Ala Asp Gly Thr Pro Ile Thr Gln Gly Val Glu Met
                180                 185                 190

Thr Thr Pro Ser Lys Gln Ser Asn Asn Lys Tyr Ala Ala Ser Ser Tyr
            195                 200                 205

Leu Ser Leu Thr Pro Glu Gln Trp Arg Ser Arg Ser Tyr Ser Cys
        210                 215                 220

Gln Val Met His Glu Gly Ser Thr Val Glu Lys Thr Val Ala Pro Ala
225                 230                 235                 240

Glu Cys Ser

<210> SEQ ID NO 26
<211> LENGTH: 188
<212> TYPE: PRT
<213> ORGANISM: Artificial Sequence
<220> FEATURE:
<223> OTHER INFORMATION: Synthetic construct

<400> SEQUENCE: 26

Met Arg Pro Gly Thr Gly Gln Gly Gly Leu Glu Ala Pro Gly Glu Pro
  1               5                  10                  15

Gly Pro Asn Leu Arg Gln Arg Trp Pro Leu Leu Leu Gly His Ala
                20                  25                  30

Glu Gly Thr Phe Thr Ser Asp Val Ser Ser Tyr Leu Glu Gly Gln Ala
            35                  40                  45

Ala Lys Glu Phe Ile Ala Trp Leu Val Lys Gly Arg Leu Ala Val Val
        50                  55                  60

Thr His Gly Ser Val Thr His Val Phe Gly Ser Gly Thr Gln Leu Thr
65                  70                  75                  80

Val Leu Ser Gln Pro Lys Ala Thr Pro Ser Val Thr Leu Phe Pro Pro
                85                  90                  95

Ser Ser Glu Glu Leu Gln Ala Asn Lys Ala Thr Leu Val Cys Leu Met
               100                 105                 110

Asn Asp Phe Tyr Pro Gly Ile Leu Thr Val Thr Trp Lys Ala Asp Gly
            115                 120                 125

Thr Pro Ile Thr Gln Gly Val Glu Met Thr Thr Pro Ser Lys Gln Ser
        130                 135                 140

Asn Asn Lys Tyr Ala Ala Ser Ser Tyr Leu Ser Leu Thr Pro Glu Gln
145                 150                 155                 160

Trp Arg Ser Arg Ser Tyr Ser Cys Gln Val Met His Glu Gly Ser
                165                 170                 175

Thr Val Glu Lys Thr Val Ala Pro Ala Glu Cys Ser
            180                 185
```

<210> SEQ ID NO 27
<211> LENGTH: 105
<212> TYPE: PRT
<213> ORGANISM: Homo sapiens

<400> SEQUENCE: 27

```
Gly Ser Gln Ser Val Leu Thr Gln Pro Pro Ser Val Ser Ala Ala Pro
 1               5                  10                  15
Gly Gln Lys Val Thr Ile Ser Cys Ser Gly Ser Ser Ser Asn Ile Gly
            20                  25                  30
Asn Asn Tyr Val Ser Trp Tyr Gln Gln Leu Pro Gly Thr Ala Pro Lys
        35                  40                  45
Leu Leu Ile Tyr Asp Asn Asn Lys Arg Pro Ser Gly Ile Pro Asp Arg
    50                  55                  60
Phe Ser Gly Ser Lys Ser Gly Thr Ser Ala Thr Leu Gly Ile Thr Gly
 65                 70                  75                  80
Leu Gln Thr Gly Asp Glu Ala Asp Tyr Tyr Cys Gly Thr Trp Asp Ser
                85                  90                  95
Ser Leu Ser Ala Val Val Phe Gly Gly
            100                 105
```

<210> SEQ ID NO 28
<211> LENGTH: 114
<212> TYPE: PRT
<213> ORGANISM: Homo sapiens

<400> SEQUENCE: 28

```
Gly Gly Thr Lys Leu Thr Val Leu Arg Gln Pro Lys Ala Ala Pro Ser
 1               5                  10                  15
Val Thr Leu Phe Pro Pro Ser Ser Glu Glu Leu Gln Ala Asn Lys Ala
            20                  25                  30
Thr Leu Val Cys Leu Ile Ser Asp Phe Tyr Pro Gly Ala Val Thr Val
        35                  40                  45
Ala Trp Lys Ala Asp Gly Ser Pro Val Lys Ala Gly Val Glu Thr Thr
    50                  55                  60
Thr Pro Ser Lys Gln Ser Asn Asn Lys Tyr Ala Ala Ser Ser Tyr Leu
 65                 70                  75                  80
Ser Leu Thr Pro Glu Gln Trp Lys Ser His Lys Ser Tyr Ser Cys Gln
                85                  90                  95
Val Thr His Glu Gly Ser Thr Val Glu Lys Thr Val Ala Pro Thr Glu
            100                 105                 110
Cys Ser
```

<210> SEQ ID NO 29
<211> LENGTH: 105
<212> TYPE: PRT
<213> ORGANISM: Homo sapiens

<400> SEQUENCE: 29

```
Gln Pro Val Leu Thr Gln Pro Ser Ser His Ser Ala Ser Ser Gly Ala
 1               5                  10                  15
Ser Val Arg Leu Thr Cys Met Leu Ser Ser Gly Phe Ser Val Gly Asp
            20                  25                  30
Phe Trp Ile Arg Trp Tyr Gln Gln Lys Pro Gly Asn Pro Pro Arg Tyr
        35                  40                  45
Leu Leu Tyr Tyr His Ser Asp Ser Asn Lys Gly Gln Gly Ser Gly Val
```

```
                    50                  55                  60
Pro Ser Arg Phe Ser Gly Ser Asn Asp Ala Ser Ala Asn Ala Gly Ile
 65                  70                  75                  80

Leu Arg Ile Ser Gly Leu Gln Pro Glu Asp Glu Ala Asp Tyr Tyr Cys
                 85                  90                  95

Gly Thr Trp His Ser Asn Ser Lys Thr
            100                 105
```

<210> SEQ ID NO 30
<211> LENGTH: 104
<212> TYPE: PRT
<213> ORGANISM: Homo sapiens

<400> SEQUENCE: 30

```
Gln Ala Val Leu Thr Gln Pro Ala Ser Leu Ser Ala Ser Pro Gly Ala
  1               5                  10                  15

Ser Ala Ser Leu Thr Cys Thr Leu Arg Ser Gly Ile Asn Val Gly Thr
                 20                  25                  30

Tyr Arg Ile Tyr Trp Tyr Gln Gln Lys Pro Gly Ser Pro Pro Gln Tyr
             35                  40                  45

Leu Leu Arg Tyr Lys Ser Asp Ser Asp Lys Gln Gly Ser Gly Val
 50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp His Ser Ser Ala Ser
            100
```

<210> SEQ ID NO 31
<211> LENGTH: 104
<212> TYPE: PRT
<213> ORGANISM: Homo sapiens

<400> SEQUENCE: 31

```
Gln Pro Val Leu Thr Gln Pro Pro Ser Ser Ala Ser Pro Gly Glu
  1               5                  10                  15

Ser Ala Arg Leu Thr Cys Thr Leu Pro Ser Asp Ile Asn Val Gly Ser
                 20                  25                  30

Tyr Asn Ile Tyr Trp Tyr Gln Gln Lys Pro Gly Ser Pro Pro Arg Tyr
             35                  40                  45

Leu Leu Tyr Tyr Tyr Ser Asp Ser Asp Lys Gly Gln Gly Ser Gly Val
 50                  55                  60

Pro Ser Arg Phe Ser Gly Ser Lys Asp Ala Ser Ala Asn Thr Gly Ile
 65                  70                  75                  80

Leu Leu Ile Ser Gly Leu Gln Ser Glu Asp Glu Ala Asp Tyr Tyr Cys
                 85                  90                  95

Met Ile Trp Pro Ser Asn Ala Ser
            100
```

<210> SEQ ID NO 32
<211> LENGTH: 113
<212> TYPE: PRT
<213> ORGANISM: Homo sapiens

<400> SEQUENCE: 32

```
Gly Thr Lys Leu Thr Val Leu Arg Gln Pro Lys Ala Ala Pro Ser Val
  1               5                  10                  15
```

```
Thr Leu Phe Pro Pro Ser Ser Glu Glu Leu Gln Ala Asn Lys Ala Thr
            20                  25                  30

Leu Val Cys Leu Ile Ser Asp Phe Tyr Pro Gly Ala Val Thr Val Ala
        35                  40                  45

Trp Lys Ala Asp Gly Ser Pro Val Lys Ala Gly Val Glu Thr Thr Thr
    50                  55                  60

Pro Ser Lys Gln Ser Asn Asn Lys Tyr Ala Ala Ser Ser Tyr Leu Ser
65                  70                  75                  80

Leu Thr Pro Glu Gln Trp Lys Ser His Lys Ser Tyr Ser Cys Gln Val
                85                  90                  95

Thr His Glu Gly Ser Thr Val Glu Lys Thr Val Ala Pro Thr Glu Cys
                100                 105                 110

Ser

<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 34
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 34

His His His His His His
1               5

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Gly Gly Gly Ser Gly Gly Gly Gly Ser Gly Gly Gly Gly Ser
1               5                   10                  15
```